United States Patent
Yano et al.

(10) Patent No.: US 11,193,066 B2
(45) Date of Patent: *Dec. 7, 2021

(54) POLYMERIZABLE COMPOUND AND COMPOSITION, LIQUID CRYSTAL COMPOSITE, OPTICAL ANISOTROPIC BODY, LIQUID CRYSTAL DISPLAY DEVICE AND USE THEREOF

(71) Applicants: JNC CORPORATION, Tokyo (JP); JNC PETROCHEMICAL CORPORATION, Tokyo (JP)

(72) Inventors: Tomohiro Yano, Chiba (JP); Fumitaka Kondo, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/098,133

(22) PCT Filed: May 8, 2017

(86) PCT No.: PCT/JP2017/017383
§ 371 (c)(1),
(2) Date: Nov. 1, 2018

(87) PCT Pub. No.: WO2017/199778
PCT Pub. Date: Nov. 23, 2017

(65) Prior Publication Data
US 2019/0136135 A1    May 9, 2019

(30) Foreign Application Priority Data
May 19, 2016 (JP) .............................. JP2016-100573

(51) Int. Cl.
*G02F 1/1333* (2006.01)
*C09K 19/54* (2006.01)
(Continued)

(52) U.S. Cl.
CPC ........ *C09K 19/542* (2013.01); *C07D 207/448* (2013.01); *C07D 207/452* (2013.01); *C09K 19/3001* (2013.01); *C09K 19/3003* (2013.01); *C09K 19/3068* (2013.01); *C09K 19/3402* (2013.01); *C09K 19/3458* (2013.01); *C09K 19/38* (2013.01); *C09K 19/54* (2013.01); *G02F 1/13* (2013.01); *C09K 2019/301* (2013.01); *C09K 2019/3009* (2013.01); *C09K 2019/3016* (2013.01); *C09K 2019/3077* (2013.01); *C09K 2019/3083* (2013.01);
(Continued)

(58) Field of Classification Search
CPC .............. C09K 19/542; C09K 19/3001; C09K 19/3003; C09K 19/3068; C09K 19/3402; C09K 19/3458; C09K 19/38; C09K 19/54; C09K 2019/3009; C09K 2019/301; C09K 2019/3016; C09K 2019/3077; C09K 2019/3083; C09K 2019/3422; C09K 2019/548; G02F 1/13; G02F 1/1333; G02F 1/137; G02F 2001/13775; C07D 207/448; C07D 207/452
USPC ...................................................... 252/299.5
See application file for complete search history.

(56) References Cited

U.S. PATENT DOCUMENTS 5,077,156 A      12/1991  Finter et al.
7,070,838 B2 *    7/2006  Sasada ............... C09K 19/0403
                                                              252/299.01
(Continued)

FOREIGN PATENT DOCUMENTS

CN    101671252    3/2010
EP      1889894    2/2008
(Continued)

OTHER PUBLICATIONS

Murai, H., et al. ,"Liquid crystal photoalignment layers made from aromatic bismaleimides", Liquid Crystals, vol. 29, No. 5, May 2002, pp. 669-673.
(Continued)

*Primary Examiner* — Geraldina Visconti
(74) *Attorney, Agent, or Firm* — JCIPRNET

(57) ABSTRACT

Provided are a polymerizable compound having at least one monovalent group (A), a polymerizable composition containing the polymerizable compound, a liquid crystal composite prepared from the polymerizable composition, and a liquid crystal device having the polymerizable composition.

(A)

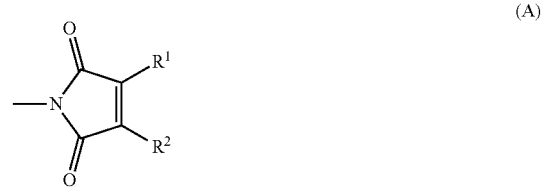

In monovalent group (A), $R^1$ and $R^2$ are independently hydrogen, halogen or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen.

13 Claims, No Drawings

(51) Int. Cl.
*C07D 207/448* (2006.01)
*C07D 207/452* (2006.01)
*C09K 19/38* (2006.01)
*G02F 1/13* (2006.01)
*C09K 19/30* (2006.01)
*C09K 19/34* (2006.01)
*G02F 1/137* (2006.01)

(52) U.S. Cl.
CPC .......... *C09K 2019/3422* (2013.01); *C09K 2019/548* (2013.01); *G02F 1/137* (2013.01); *G02F 1/13775* (2021.01)

(56) References Cited

U.S. PATENT DOCUMENTS

| | | | | |
|---|---|---|---|---|
| 7,834,070 | B2 * | 11/2010 | Tseng | C08G 59/4042 428/209 |
| 8,512,596 | B2 * | 8/2013 | Kim | C09K 19/322 252/299.01 |
| 8,961,823 | B2 * | 2/2015 | Gotoh | C09K 19/12 252/299.62 |
| 10,581,022 | B2 * | 3/2020 | Ootsuki | C09K 19/3486 |
| 2001/0006410 | A1 | 7/2001 | Yamada et al. | |
| 2004/0011996 | A1 | 1/2004 | Klasen-Memmer et al. | |
| 2005/0007541 | A1 | 1/2005 | Sasada et al. | |
| 2005/0116200 | A1 | 6/2005 | Nakanishi et al. | |
| 2007/0152311 | A1 * | 7/2007 | Jayaraman | H01L 21/563 257/678 |
| 2010/0309423 | A1 | 12/2010 | Bernatz et al. | |
| 2013/0134354 | A1 | 5/2013 | Gotoh et al. | |
| 2014/0008572 | A1 | 1/2014 | Gotoh et al. | |

FOREIGN PATENT DOCUMENTS

| | | | |
|---|---|---|---|
| JP | S63227568 | 9/1988 | |
| JP | H10186330 | 7/1998 | |
| JP | 2001122981 | 5/2001 | |
| JP | 2002194169 | 7/2002 | |
| JP | 2003-307720 | 10/2003 | |
| JP | 2004-131704 | 4/2004 | |
| JP | 2004204190 | 7/2004 | |
| JP | 2005035985 | 2/2005 | |
| JP | 2005-179557 | * 7/2005 | ............ C08F 20/22 |
| JP | 2005179557 | 7/2005 | |
| JP | 2006-133619 | 5/2006 | |
| JP | 2010107618 | 5/2010 | |
| JP | 2010-537256 | 12/2010 | |
| JP | 2011043807 | 3/2011 | |
| JP | 2012-180484 | * 9/2012 | ........... G02F 1/1337 |
| JP | 2012180482 | 9/2012 | |
| JP | 2012180484 | 9/2012 | |
| JP | 2012523486 | 10/2012 | |
| WO | 2010118755 | 10/2010 | |
| WO | 2013077343 | 5/2013 | |
| WO | 2014006962 | 1/2014 | |

OTHER PUBLICATIONS

Database Registry, Oct. 31, 2010, RN 1249078-99-6,retrieved from STN international [onine]; retrieved on May 24, 2017, 1-(4-propylcyclohexyl)-1 H-Pyrrole-2,5-dione.
"International Search Report (Form PCT/ISA/210)"of PCT/JP2017/0173833, dated Aug. 8, 2017, with English translation thereof, pp. 1-12.
Richard J. Hooley et al., "A deep cavitand catalyzes the Diels-Alder reaction of bound maleimides". Organic & Biomolecular Chemistry, Jan. 1, 2007, pp. 3631-3636.
"Search Report of Europe Counterpart Application", dated Mar. 5, 2020, p. 1-p. 8.
"Office Action of Taiwan Counterpart Application", dated Jan. 8, 2021, with English translation thereof, p. 1-p. 15.
William J. Leigh, et al., "Organic Reactions in Liquid-Crystalline Solvents. Regiochemical Control of Bimolecular Pericyclic Reactions by Cholesteric and Smectic Liquid-Crystalline Solvents," J. Am. Chem. Soc., Jun. 1992, pp. 5005-5010.
"Office Action of Taiwan Counterpart Application" with English translation thereof, dated Jul. 12, 2021, p. 1-p. 15.

* cited by examiner

POLYMERIZABLE COMPOUND AND COMPOSITION, LIQUID CRYSTAL COMPOSITE, OPTICAL ANISOTROPIC BODY, LIQUID CRYSTAL DISPLAY DEVICE AND USE THEREOF

CROSS-REFERENCE TO RELATED APPLICATION

This application is a 371 application of the international PCT application serial no. PCT/JP2017/017383, filed on May 8, 2017, which claims the priority benefit of Japan application no. 2016-100573, filed on May 19, 2016. The entirety of each of the abovementioned patent applications is hereby incorporated by reference herein and made a part of this specification.

TECHNICAL FIELD

The invention relates to a polymerizable compound, a polymerizable composition containing the polymerizable compound and a liquid crystal composition, a liquid crystal composite prepared from the polymerizable composition, and a liquid crystal display device.

BACKGROUND ART

A liquid crystal display device utilizes optical anisotropy, dielectric anisotropy and so forth of liquid crystal molecules in a liquid crystal composition. Classification based on an operating mode of the liquid crystal molecules includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a fringe field switching (FFS) mode and a vertical alignment (VA) mode.

In such a liquid crystal display device, initial alignment thereof is achieved by a polyimide alignment film. On the other hand, in the liquid crystal display device having no alignment film, a liquid crystal composition containing a polar compound and a polymer or a polymerizable polar compound is used. First, a composition to which a small amount of the polar compound and a small amount of the polymerizable compound or a small amount of the polymerizable polar compound are added is injected into a device. Here, the liquid crystal molecules may be occasionally aligned by action of the polar compound. Next, the composition is irradiated with ultraviolet light. Here, the polymerizable compound or the polymerizable polar compound is polymerized. Accordingly, the liquid crystal molecules are aligned, and stabilized. Alternatively, alignment after injection is stabilized. In the composition, the alignment of the liquid crystal molecules can be controlled by the polar compound and the polymer or the polymerizable polar compound, and therefore a response time of the device is shortened and also image persistence is improved. Further, the device having no alignment film does not require a step of forming the alignment film. The device has no alignment film, and therefore reduction of electric resistance of the device by interaction between the alignment film and the composition is not caused. Such an effect by a combination of the polar compound and the polymer can be expected in the device having the mode such as the TN mode, the ECB mode, the OCB mode, the IPS mode, the VA mode, the FFS mode and the FPA mode.

A method of combining the polymer with the liquid crystal composition can be applied to the liquid crystal display devices having various operating modes, and modes such as a PS-TN mode, a PS-IPS mode, a PS-FFS mode, a PSA-VA mode and a PSA-OCB mode are known. For the polymerizable compound used in the device having such a mode, characteristics such as excellent capability of aligning the liquid crystal molecules, suitable polymerization reactivity, high conversion and high solubility in the liquid crystal composition are required. Various polymerizable compounds have been developed so far, but development of a compound in which the characteristics described above are further improved is desired.

CITATION LIST

Patent Literature

Patent literature No. 1: JP 2003-307720 A.
Patent literature No. 2: JP 2004-131704 A.
Patent literature No. 3: JP 2006-133619 A.
Patent literature No. 4: JP 2010-537256 A.
Patent literature No. 5: JP H10-186330 A.
Patent literature No. 6: EP 1889894 A.
Patent literature No. 7: CN 101671252 A.
Patent literature No. 8: WO 2013/77343 A.
Patent literature No. 9: WO 2014/6962 A.

SUMMARY OF INVENTION

Technical Problem

A first object of the invention is to provide a polymerizable compound having excellent capability of aligning liquid crystal molecules, suitable polymerization reactivity, high conversion and high solubility in a liquid crystal composition. A second object is to provide a liquid crystal composite satisfying at least one of physical properties such as a high maximum temperature of a nematic phase, a low minimum temperature of the nematic phase, small viscosity, suitable optical anisotropy, large dielectric anisotropy, a suitable elastic constant, large specific resistance and a suitable pretilt. The object is to provide a liquid crystal composite having a suitable balance regarding at least two of the physical properties. A third object is to provide a liquid crystal display device having a wide temperature range in which the device can be used, a short response time, a large voltage holding ratio, a low threshold voltage, a large contrast ratio and a long service life.

Solution to Problem

The invention concerns a polymerizable compound having at least one monovalent group represented by formula (A).

(A)

In formula (A), $R^1$ and $R^2$ are independently hydrogen, halogen or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen.

Advantageous Effects of Invention

A first advantage of the invention is to provide a polymerizable compound having excellent capability of aligning liquid crystal molecules, suitable polymerization reactivity, high conversion and high solubility in a liquid crystal composition. A second advantage is to provide a liquid crystal composite satisfying at least one of physical properties such as a high maximum temperature of a nematic phase, a low minimum temperature of the nematic phase, small viscosity, suitable optical anisotropy, large dielectric anisotropy, a suitable elastic constant, large specific resistance and a suitable pretilt. The advantage is to provide a liquid crystal composite having a suitable balance regarding at least two of the physical properties. A third advantage is to provide a liquid crystal display device having a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a non-polymerizable compound having a liquid crystal phase such as a nematic phase and a smectic phase, and a non-polymerizable compound having no liquid crystal phase but being mixed for the purpose of adjusting physical properties of a liquid crystal composition, such as a maximum temperature, a minimum temperature, viscosity and dielectric anisotropy. The compound has a six-membered ring such as 1,4-cyclohexylene and 1,4-phenylene, and a rod-like molecular structure. The liquid crystal composition is a mixture of the liquid crystal compounds. A polymerizable compound is a compound added for the purpose of forming a polymer. A polymerizable composition is a mixture of the polymerizable compound, the liquid crystal composition, an additive and so forth. A liquid crystal composite is a composite formed by polymerization of the polymerizable composition. A liquid crystal display device is a generic term for a liquid crystal display panel and a liquid crystal display module. A maximum temperature of the nematic phase is a phase transition temperature between a nematic phase and an isotropic phase in the liquid crystal composition, the polymerizable composition or the liquid crystal composite, and may be occasionally abbreviated as the maximum temperature. A minimum temperature of the nematic phase may be occasionally abbreviated as the minimum temperature. Polymerization reactivity means a degree of ease when a reactant is polymerized. Conversion is expressed in terms of a weight ratio of the reactant consumed by a chemical reaction relative to an original reactant.

The liquid crystal composition is prepared by mixing the liquid crystal compounds. A proportion (content) of the liquid crystal compounds is expressed in terms of weight percent (% by weight) based on the weight of the liquid crystal composition. The additive such as an optically active compound, an antioxidant, an ultraviolet light absorber, a light stabilizer, a heat stabilizer, an antifoaming agent, the polymerizable compound, a polymerization initiator and a polymerization inhibitor is added to the composition, when necessary. A proportion (amount of addition) of the additive is expressed in terms of weight percent (% by weight) based on the weight of the liquid crystal composition in a manner similar to the proportion of the liquid crystal compound. Weight parts per million (ppm) may be occasionally used. A proportion of the polymerization initiator and the polymerization inhibitor is exceptionally expressed based on the weight of the polymerizable compound.

A compound represented by formula (1) may be occasionally abbreviated as compound (1). At least one compound selected from the group of compounds represented by formula (1) may be occasionally abbreviated as "compound (1)." "Compound (1)" means one compound, a mixture of two compounds or a mixture of three or more compounds represented by formula (1). A same rule applies also to any other compound represented by any other formula. In ring $A^1$ of compound (1), a line crossing a circle means that a bonding position on a ring such as a six-membered ring and a condensed ring can be arbitrarily selected for a $P^1$—$S^1$ group. A same rule applies also to a symbol such as a $P^2$—$S^2$ group. In formulas (2) to (8), a symbol such as $B^1$, $C^1$, $D^1$ surrounded by a hexagonal shape corresponds to a ring such as ring $B^1$, ring $C^1$ and ring $D^1$. A symbol of $R^{11}$ is used for a plurality of formulas such as formula (2) and formula (3). In the compounds, two terminal groups represented by two of arbitrary $R^{11}$ may be identical or different. In formula (8), when i is 2, two of $D^1$ exists in one formula. In the compound, two rings represented by two of $D^1$ may be identical or different. A same rule applies also to $D^1$ when j is larger than 2. A same rule applies also to any other symbol such as a $P^1$—$S^1$ group.

An expression "at least one piece of 'A' may be replaced by 'B'" means that, when the number of 'A' is 1, a position of 'A' is arbitrary, and also when the number of 'A' is 2 or more, positions thereof can be freely selected without restriction. An expression "at least one piece of A may be replaced by B, C or D" means inclusion of a case where at least one piece of A is replaced by B, a case where at least one piece of A is replaced by C, and a case where at least one piece of A is replaced by D, and also a case where a plurality of A are replaced by at least two of B, C or D. For example, alkyl in which at least one piece of —$CH_2$— (or —$CH_2CH_2$—) may be replaced by —O— (or —CH=CH—) includes alkyl, alkenyl, alkoxy, alkoxyalkyl, alkoxyalkenyl and alkenyloxyalkyl. In addition, a case where two pieces of consecutive —$CH_2$— are replaced by —O— to form —O—O— is not preferred. In alkyl or the like, a case where —$CH_2$— of a methyl part (—$CH_2$—H) is replaced by —O— to form —O—H is not preferred, either.

Then, 2-fluoro-1,4-phenylene means two divalent groups described below. In a chemical formula, fluorine may be leftward (L) or rightward (R). A same rule applies also to a left-right asymmetrical divalent group derived from a ring such as tetrahydropyran-2,5-diyl.

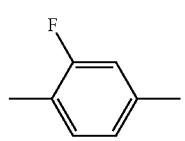

(L)

-continued

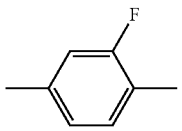
(R)

Halogen means fluorine, chlorine, bromine and iodine. Preferred halogen is fluorine or chlorine, and further preferred halogen is fluorine.

The invention includes items described below.

Item 1. A polymerizable compound, having at least one monovalent group represented by formula (A):

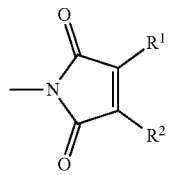
(A)

wherein, in formula (A), $R^1$ and $R^2$ are independently hydrogen, halogen or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen.

Item 2. The polymerizable compound according to item 1, represented by formula (1):

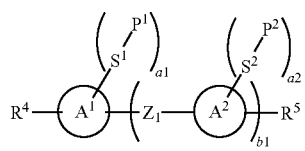
(1)

wherein, in formula (1), $P^1$ and $P^2$ are independently a polymerizable group;

$S^1$ and $S^2$ are independently a single bond or alkylene having 1 to 10 carbons, and in the alkylene, at least one piece of —$CH_2$— may be replaced by —O—, —CO—, —COO— or —OCO—, and at least one piece of —$CH_2$—$CH_2$— may be replaced by —CH=CH— or —C≡C—, and in the divalent groups, at least one hydrogen may be replaced by halogen or alkyl having 1 to 3 carbons;

$R^4$ and $R^5$ are independently hydrogen, halogen, —$S^1$—$P^1$, —$S^2$—$P^2$ or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen;

a1 and a2 are independently 0, 1, 2, 3 or 4;

the total number of —$S^1$—$P^1$ and —$S^2$—$P^2$ is 1 to 8, and at least one of all of —$S^1$—$P^1$ and all of —$S^2$—$P^2$ is a monovalent group represented by formula (A):

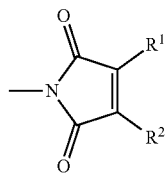
(A)

wherein, in formula (A), $R^1$ and $R^2$ are independently hydrogen, halogen or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen; and in formula (1), ring $A^1$ and ring $A^2$ are independently a divalent group derived from alicyclic hydrocarbon having 3 to 18 carbons, aromatic hydrocarbon having 6 to 18 carbons or heteroaromatic hydrocarbon having 3 to 18 carbons, and in the divalent groups, at least one hydrogen may be replaced by halogen, alkyl having 1 to 12 carbons, alkoxy having 1 to 12 carbons, alkenyl having 1 to 12 carbons or alkenyloxy having 2 to 12 carbons, and in the monovalent hydrocarbon groups, at least one hydrogen may be replaced by halogen;

$Z^1$ is a single bond or alkylene having 1 to 10 carbons, and in the alkylene, at least one piece of —$CH_2$— may be replaced by —O—, —CO—, —COO— or —OCO—, and at least one piece of —$CH_2$—$CH_2$— may be replaced by —CH=CH—, —C($CH_3$)=CH—, —CH=C($CH_3$)—, —C($CH_3$)=C($CH_3$)— or —CH≡CH—, and in divalent groups, at least one hydrogen may be replaced by halogen; and b1 is 0, 1, 2 or 3.

Item 3. The polymerizable compound according to item 1, represented by any one of formula (1-1-1) to formula (1-1-3):

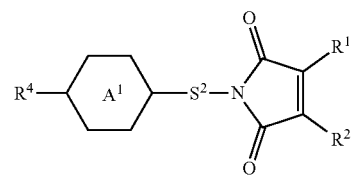
(1-1-1)

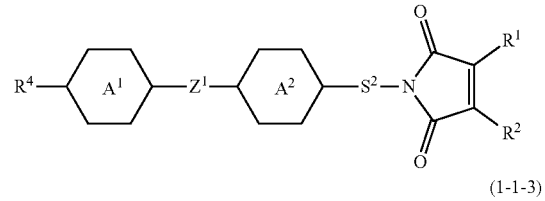
(1-1-2)

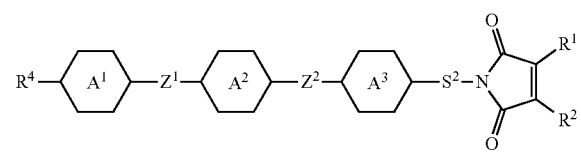
(1-1-3)

wherein, in formula (1-1-1) to formula (1-1-3), $R^1$ and $R^2$ are independently hydrogen, halogen or alkyl having 1 to 20 carbons, and in the alkyl, at least one piece of —CH$_2$— may be replaced by —O— or —S—, and at least one piece of —(CH$_2$)$_2$— may be replaced by —CH═CH—, and in the groups, at least one hydrogen may be replaced by halogen;

R$^4$ is hydrogen, halogen, —S$^1$—P$^1$ or alkyl having 1 to 20 carbons, and in the alkyl, at least one piece of —CH$_2$— may be replaced by —O— or —S—, and at least one piece of —(CH$_2$)$_2$— may be replaced by —CH═CH—, and in the groups, at least one hydrogen may be replaced by halogen;

S$^1$ and S$^2$ are independently a single bond or alkylene having 1 to 10 carbons, and in the alkylene, at least one piece of —CH$_2$— may be replaced by —O—, —CO—, —COO— or —OCO—, and at least one piece of —CH$_2$—CH$_2$— may be replaced by —CH═CH— or —C≡C—, and in the divalent groups, at least one hydrogen may be replaced by halogen or alkyl having 1 to 3 carbons;

P$^1$ is a polymerizable group;

ring A$^1$, ring A$^2$ and ring A$^3$ are independently a divalent group derived from alicyclic hydrocarbon having 3 to 18 carbons, aromatic hydrocarbon having 6 to 18 carbons or heteroaromatic hydrocarbon having 3 to 18 carbons, and in the divalent groups, at least one hydrogen may be replaced by halogen, alkyl having 1 to 12 carbons, alkoxy having 1 to 12 carbons, alkenyl having 1 to 12 carbons or alkenyloxy having 2 to 12 carbons, and in the monovalent hydrocarbon groups, at least one hydrogen may be replaced by halogen; and Z$^1$ and Z$^2$ are independently a single bond or alkylene having 1 to 10 carbons, and in the alkylene, at least one piece of —CH$_2$— may be replaced by —O—, —CO—, —COO— or —OCO—, and at least one piece of —CH$_2$—CH$_2$— may be replaced by —CH═CH—, —C(CH$_3$)═CH—, —CH═C(CH$_3$)—, —C(CH$_3$)═C(CH$_3$)— or —CH≡CH—, and in the divalent groups, at least one hydrogen may be replaced by halogen.

Item 4. The polymerizable compound according to item 1, represented by any one of formula (1-1-4) to formula (1-1-6):

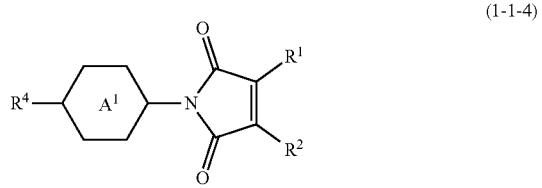

(1-1-4)

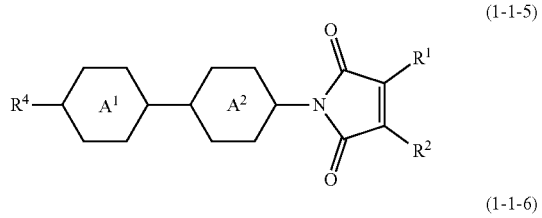

(1-1-5)

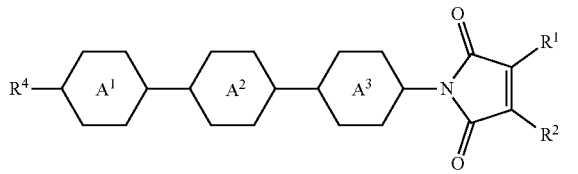

(1-1-6)

wherein, in formula (1-1-4) to formula (1-1-6),

R$^1$ and R$^2$ are independently hydrogen, halogen or alkyl having 1 to 20 carbons, and in the alkyl, at least one piece of —CH$_2$— may be replaced by —O— or —S—, and at least one piece of —(CH$_2$)$_2$— may be replaced by —CH═CH—, and in the groups, at least one hydrogen may be replaced by halogen;

R$^4$ is hydrogen, halogen, —S$^1$—P$^1$ or alkyl having 1 to 20 carbons, and in the alkyl, at least one piece of —CH$_2$— may be replaced by —O— or —S—, and at least one piece of —(CH$_2$)$_2$— may be replaced by —CH═CH—, and in the groups, at least one hydrogen may be replaced by halogen;

S$^1$ is a single bond or alkylene having 1 to 10 carbons, and in the alkylene, at least one piece of —CH$_2$— may be replaced by —O—, —CO—, —COO— or —OCO—, and at least one piece of —CH$_2$—CH$_2$— may be replaced by —CH═CH— or —C≡C—, and in the divalent groups, at least one hydrogen may be replaced by halogen or alkyl having 1 to 3 carbons;

P$^1$ is a polymerizable group; and ring A$^1$, ring A$^2$ and ring A$^3$ are independently a divalent group derived from alicyclic hydrocarbon having 3 to 18 carbons, aromatic hydrocarbon having 6 to 18 carbons or heteroaromatic hydrocarbon having 3 to 18 carbons, and in the divalent groups, at least one hydrogen may be replaced by halogen, alkyl having 1 to 12 carbons, alkoxy having 1 to 12 carbons, alkenyl having 1 to 12 carbons or alkenyloxy having 2 to 12 carbons, and in the monovalent hydrocarbon groups, at least one hydrogen may be replaced by halogen.

Item 5. The polymerizable compound according to item 1, represented by formula (1-1-5):

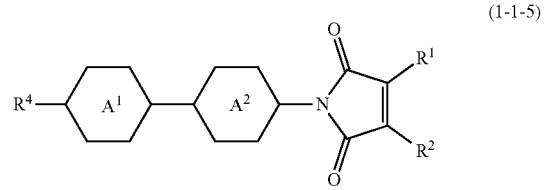

(1-1-5)

wherein, in formula (1-1-5),

R$^1$ and R$^2$ are independently hydrogen, halogen or alkyl having 1 to 20 carbons, and in the alkyl, at least one piece of —CH$_2$— may be replaced by —O— or —S—, and at least one piece of —(CH$_2$)$_2$— may be replaced by —CH═CH—, and in the groups, at least one hydrogen may be replaced by halogen;

R$^4$ is hydrogen, halogen or alkyl having 1 to 20 carbons, and in the alkyl, at least one piece of —CH$_2$— may be replaced by —O— or —S—, and at least one piece of —(CH$_2$)$_2$— may be replaced by —CH═CH—, and in the groups, at least one hydrogen may be replaced by halogen; and ring A$^1$ and ring A$^2$ are independently 1,4-cyclohexylene, 1,4-cyclohexenylene and 1,4-phenylene, and at least one hydrogen on the rings may be replaced by halogen.

Item 6. The polymerizable compound according to item 1, represented by formula (1-1-7):

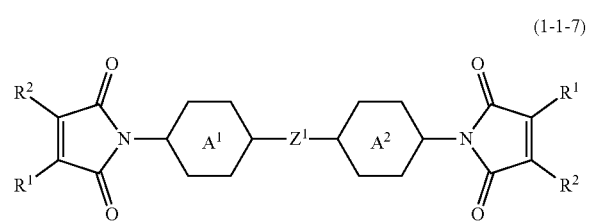

(1-1-7)

wherein, in formula (1-1-7),

R$^1$ and R$^2$ are independently hydrogen, halogen or alkyl having 1 to 20 carbons, and in the alkyl, at least one piece of —CH$_2$— may be replaced by —O— or —S—, and at least one piece of —(CH$_2$)$_2$— may be replaced by —CH=CH—, and in the groups, at least one hydrogen may be replaced by halogen;

ring A$^1$ and ring A$^2$ are independently 1,4-cyclohexylene and 1,4-phenylene, and at least one hydrogen on the rings may be replaced by halogen; and Z$^1$ is a single bond or alkylene having 1 to 10 carbons, and in the alkylene, at least one piece of —CH$_2$— may be replaced by —O—, —CO—, —COO— or —OCO—, and at least one piece of —CH$_2$—CH$_2$— may be replaced by —CH=CH—, —C(CH$_3$)=CH—, —CH=C(CH$_3$)—, —C(CH$_3$)=C(CH$_3$)— or —CH=CH—, and in the divalent groups, at least one hydrogen may be replaced by halogen.

Item 7. A polymerizable composition, containing at least one polymerizable compound according to any one of items 1 to 6.

Item 8. The polymerizable composition according to item 7, further containing at least one compound selected from the group of compounds represented by formulas (2) to (4):

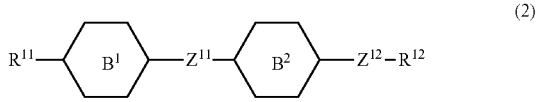

(2)

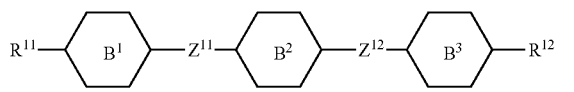

(3)

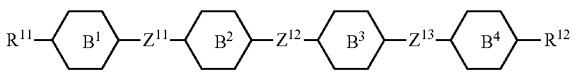

(4)

wherein, in formulas (2) to (4),

R$^{11}$ and R$^{12}$ are independently alkyl having 1 to 10 carbons or alkenyl having 2 to 10 carbons, and in the alkyl or the alkenyl, at least one piece of —CH$_2$— may be replaced by —O—, and at least one hydrogen may be replaced by fluorine;

ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and Z$^{11}$, Z$^{12}$ and Z$^{13}$ are independently a single bond, —CH$_2$CH$_2$—, —CH=CH—, —C≡C— or —COO—.

Item 9. The polymerizable composition according to item 7 or 8, further containing at least one compound selected from the group of compounds represented by formulas (5) to (7):

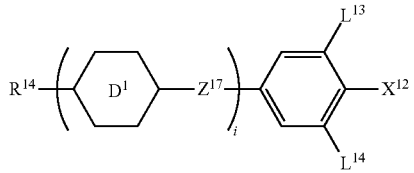

(5)

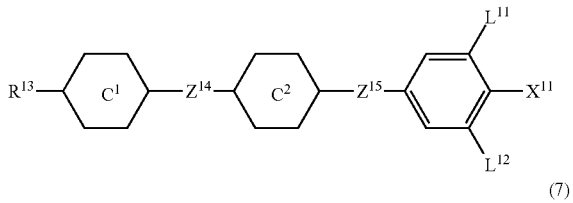

(6)

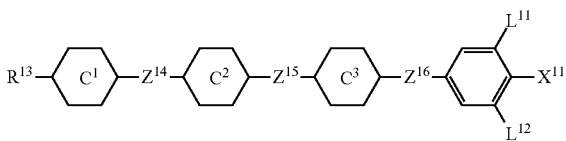

(7)

wherein, in formulas (5) to (7),

R$^{13}$ is alkyl having 1 to 10 carbons or alkenyl having 2 to 10 carbons, and in the alkyl and the alkenyl, at least one piece of —CH$_2$— may be replaced by —O—, and at least one hydrogen may be replaced by fluorine;

X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring C$^1$, ring C$^2$ and ring C$^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

Z$^{14}$, Z$^{15}$ and Z$^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and L$^{11}$ and L$^{12}$ are independently hydrogen or fluorine.

Item 10. The polymerizable composition according to any one of items 7 to 9, further containing at least one compound selected from the group of compounds represented by formula (8):

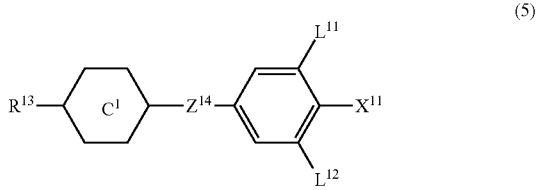

(8)

wherein, in formula (8),

R$^{14}$ is alkyl having 1 to 10 carbons or alkenyl having 2 to 10 carbons, and in the alkyl and the alkenyl, at least one piece of —CH$_2$— may be replaced by —O—, and at least one hydrogen may be replaced by fluorine;

X$^{12}$ is —C≡N or —C≡C—C≡N;

ring D$^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

Z$^{17}$ is a single bond, —CH$_2$CH$_2$—, —C≡C—, —COO—, —CF$_2$O—, —OCF$_2$—, or —CH$_2$O—;

L$^{13}$ and L$^{14}$ are independently hydrogen or fluorine; and i is 1, 2, 3 or 4.

Item 11. A liquid crystal composite, formed by polymerization of the polymerizable composition according to any one of items 7 to 10.

Item 12. An optical anisotropic body, formed by polymerization of the polymerizable composition according to any one of items 7 to 10.

Item 13. A liquid crystal display device, including the polymerizable composition according to any one of items 7 to 10 or the liquid crystal composite according to item 11.

Item 14. Use of at least one selected from the group of the polymerizable compound according to any one of items 1 to 6, the polymerizable composition according to any one of items 7 to 10 and the liquid crystal composite according to item 11 in a liquid crystal device.

The invention further includes the following items: (a) the polymerizable composition further containing at least one of additives such as an optically active compound, an antioxidant, an ultraviolet light absorber, a light stabilizer, a heat stabilizer, an antifoaming agent, a polymerization initiator and a polymerization inhibitor, (b) the polymerizable composition further containing at least one polymerization initiator, (c) the polymerizable composition further containing a polymerizable compound having no monovalent group, represented by formula (A), (d) use of compound (1) in the polymerizable composition suitable for a liquid crystal display device having a PSA mode, (e) use of compound (1) in the liquid crystal display device having the PSA mode, (f) use of at least one compound selected from the group of compounds represented by formula (1) and formulas (1-1-1) to (1-1-7), (g) use of a polymerizable composition containing at least one of the compounds in the liquid crystal display device having the PSA mode, (h) use of a liquid crystal composite formed by polymerization of the polymerizable composition in the liquid crystal display device having the PSA mode, and (i) use of the compound, the polymerizable composition or the liquid crystal composite in a liquid crystal display device having a PS-TN mode, a PS-IPS mode, a PS-FFS mode, a PSA-VA mode or a PSA-OCB mode.

The invention further includes the following items: (j) use of a composition containing a compound represented by formula (1), and at least one compound selected from the group of compounds represented by formulas (2), (3) and (4), (k) use of a composition containing the compound represented by formula (1), and at least one compound selected from the group of compounds represented by formulas (5), (6) and (7) in the liquid crystal display device having the PSA mode, and (1) use of a composition containing the compound represented by formula (1), and at least one compound selected from the group of compounds represented by formulas (8) in the liquid crystal display device having the PSA mode.

First, the polymerizable compound of the invention will be described, and then a synthetic method, the polymerizable composition, the liquid crystal composite and the liquid crystal display will be described in the above order.

1. Polymerizable Compound

The polymerizable compound of the invention has at least one monovalent group (A):

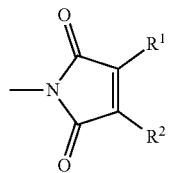

(A)

In formula (A), $R^1$ and $R^2$ are independently hydrogen, halogen, or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen.

First, compound (1) has a rod-like molecular structure similar to the structure of the liquid crystal compound, and therefore has high solubility in the liquid crystal composition. Accordingly, compound (1) is suitable as a polymerizable compound required for the device having the PSA mode. Second, compound (1) has a suitable polymerizable property. Accordingly, compound (1) can be stably stored. Upon polymerization, a photoreaction rate can be easily controlled. Compound (1) can be polymerized by suitable irradiation with ultraviolet light. Excessive ultraviolet light is not required.

In compound (1), each preferred example of polymerizable group P, connecting group S, ring A, and bonding group Z is as described below. The example is applied also to a compound at a lower level of compound (1). In compound (1), physical properties can be arbitrarily adjusted by appropriately combining types of the groups. Compound (1) may contain a larger amount of isotope such as $^2H$ (deuterium) and $^{13}C$ than the amount of natural abundance because no significant difference exists in the physical properties of the compound.

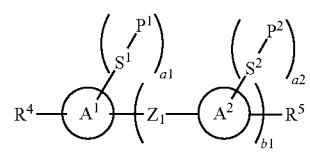

(1)

In formula (1), $P^1$ and $P^2$ are independently a polymerizable group. Specific examples of the polymerizable group include acryloyloxy, methacryloiloxy, acrylamide, methacrylamide, vinyloxy, vinylcarbonyl, oxiranyl, oxetanyl, 3,4-epoxycyclohexyl or maleimide. In the groups, at least one hydrogen may be replaced by fluorine, methyl or trifluoromethyl. Preferred examples of the polymerizable group include acryloyloxy (P-1), vinyloxy (P-2), oxiranyl (P-3) or maleimide (A), in which $M^1$ and $M^2$ are independently hydrogen, fluorine, methyl or trifluoromethyl, and definition of $R^1$ and $R^2$ is identical to the definition in the monovalent group represented by formula (A).

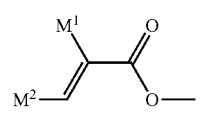

(P-1)

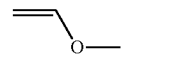

(P-2)

(P-3)

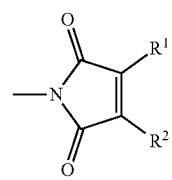

(A)

In formula (1), $S^1$ and $S^2$ are independently a single bond or alkylene having 1 to 10 carbons, and in the alkylene, at least one piece of —$CH_2$— may be replaced by —O—, —CO—, —COO— or —OCO—, and at least one piece of —$CH_2$—$CH_2$— may be replaced by —CH=CH— or —C≡C—, and in the divalent groups, at least one hydrogen may be replaced by halogen or alkyl having 1 to 3 carbons.

Preferred examples of $S^1$ or $S^2$ include a single bond, —$CH_2$—, —$CH_2O$—, —$OCH_2$—, —COO—, —OCO—, —$CH_2CH_2$—, —CH=CH—, —C≡C—, —$(CH_2)_3$—, —$CH_2CH_2O$—, —$OCH_2CH_2$—, —CH=CH—O—, —O—CH=CH—, —C≡C—O—, —O—C≡C—, —$(CH_2)_4$—, —$(CH_2)_3$—O—, —O—$(CH_2)_3$—, —$(CH_2)_4$—, —$(CH_2)_4O$— or —O$(CH_2)_4$—. Further preferred examples include a single bond, —$CH_2$—, —$CH_2O$—, —$OCH_2$—, and —COO— and —OCO— and —CH=CH— and —C≡C—, —$CH_2CH_2O$—, —$OCH_2CH_2$—, —CH=CH—O— or —O—CH=CH—. Particularly preferred examples include a single bond, —$CH_2$—, —CH=CH—, —CH=CH—O—, —O—CH=CH—, —$CH_2CH_2O$— or —$OCH_2CH_2$—. Most preferred examples include a single bond. A configuration of a double bond of —CH=CH— may be a cis form or may be a trans form. The trans form is preferred to the cis form.

In formula (1), $R^4$ and $R^5$ are independently hydrogen, halogen, —$S^1$—$P^1$, —$S^2$—$P^2$ or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen.

In formula (1), a1 and a2 are independently 0, 1, 2, 3 or 4. Then, —$S^1$—$P^1$ or —$S^2$—$P^2$ is a monovalent group involved in polymerization. A total number of —$S^1$—$P^1$ and —$S^2$—$P^2$ is 1 to 8. Preferred examples include 1 to 6, and further preferred examples include 1 to 3. Most preferred examples include 1 or 2.

In formula (1), at least one of all of —$S^1$—$P^1$ and all of —$S^2$—$P^2$ is a monovalent group represented by formula (A).

(A)

In formula (A), $R^1$ and $R^2$ are independently hydrogen, halogen, or alkyl having 1 to 20 carbons, and in the alkyl, at least one piece of —$CH_2$— may be replaced by —O— or —S—, and at least one piece of —$(CH_2)_2$— may be replaced by —CH=CH—, and in the groups, at least one hydrogen may be replaced by halogen. Preferred $R^1$ or $R^2$ is methyl, ethyl or hydrogen. Further preferred $R^1$ or $R^2$ is hydrogen.

In formula (1), ring $A^1$ and ring $A^2$ are independently a divalent group derived by removing two hydrogens from alicyclic hydrocarbon having 3 to 18 carbons, aromatic hydrocarbon having 6 to 18 carbons or heteroaromatic hydrocarbon having 3 to 18 carbons. In the divalent groups, at least one hydrogen may be replaced by halogen, alkyl having 1 to 12 carbons, alkoxy having 1 to 12 carbons, alkenyl having 1 to 12 carbons or alkenyloxy having 2 to 12 carbons, and in the monovalent hydrocarbon groups, at least one hydrogen may be replaced by halogen. Further, in ring $A^1$, a1 hydrogens are replaced by —$S^1$—$P^1$, and in ring $A^2$, a2 hydrogens are replaced by —$S^2$—$P^2$.

Specific examples of the alicyclic hydrocarbon include cyclopropane, cyclobutane, cyclohexane, cycloheptane, cyclooctane, which are represented by $C_nH_{2n}$. Any other examples include decahydronaphthalene. Specific examples of the aromatic hydrocarbon include benzene, naphthalene, anthracene, phenanthrene, fluorene, indan, indene and tetrahydronaphthalene. Specific examples of the heteroaromatic hydrocarbon include pyridine, pyrimidine, furan, pyran, thiophene and benzofuran. The above hydrocarbon may be replaced by a monovalent group such as fluorine, chlorine and alkyl. Preferred examples of ring $A^1$ or ring $A^2$ include benzene, fluorobenzene, naphthalene, fluorene, or phenanthrene. Further preferred examples include benzene or naphthalene.

In formula (1), $Z^1$ is a single bond or alkylene having 1 to 10 carbons, and in the alkylene, at least one piece of —$CH_2$— may be replaced by —O—, —CO—, —COO— or —OCO—, and at least one piece of —$CH_2$—$CH_2$— may be replace by —CH=CH—, —C($CH_3$)=CH—, —CH=C($CH_3$)—, —C($CH_3$)=C($CH_3$)— or —CH≡CH—, and in the divalent groups, at least one hydrogen may be replaced by halogen.

Preferred examples of $Z^1$ include a single bond, alkylene having 1 to 4 carbons, —COO—, —OCO—, —$CH_2O$—, —$OCH_2$—, —$CF_2O$—, —$OCF_2$—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—($CH_3$)C=CH—, —C($CH_3$)=C($CH_3$)—COO—, —OCO—C($CH_3$)=C($CH_3$)—, —CO—CH=CH—, —CH=CH—CO—, —C($CH_3$)=C($CH_3$)—, —CH=CH—$CH_2O$—, —$OCH_2$—CH=CH—, —CH=CH—$OCH_2$—, —$CH_2O$—CH=CH— or —CH≡CH—. Further preferred examples include a single bond, ethylene, —COO—, —OCO—, —CH=CH—, —CH=CH—COO—, —OCO—CH=CH— or —CH≡CH—. Most preferred examples include a single bond.

In formula (1), b1 is 0, 1, 2 or 3. When b1 is 0, the compound has one ring represented by ring $A^1$. In the above case, preferred ring $A^1$ is a divalent group derived by removing two hydrogens from a condensed ring such as naphthalene, anthracene, phenanthrene, and benzene. When b1 is 1, the compound has ring $A^1$ and ring $A^2$. In the above case, preferred ring $A^1$ or ring $A^2$ is a divalent group derived from benzene or benzene substituted by a substituent such as fluorine or methyl. When b1 is 2, the compound has three rings of ring $A^1$, ring $A^2$ and ring $A^2$. Preferred ring $A^1$ or ring $A^2$ is a divalent group derived from benzene or benzene substituted by a substituent such as fluorine.

2. Synthetic Method

A synthetic method of compound (1) will be described. Compound (1) can be prepared by suitably combining methods in synthetic organic chemistry. Methods of introducing an objective terminal group, ring and bonding group to a starting material are described in books such as Houben-Wyle (Methoden der Organische Chemie, Georg-Thieme Verlag, Stuttgart), Organic Syntheses (John Wily & Sons, Inc.), Organic Reactions (John Wily & Sons Inc.), Comprehensive Organic Synthesis (Pergamon Press) and New Experimental Chemistry Course (Shin Jikken Kagaku Koza in Japanese) (Maruzen Co., Ltd.).

2-1. Formation of Bonding Group Z

Specific examples of a method of forming bonding group Z in compound (1) is as described in the following scheme.

In the scheme, MSG$^1$ (or MSG$^2$) is a monovalent organic group having at least one ring. The monovalent organic groups represented by a plurality of MSG$^1$ (or MSG$^2$) may be identical or different. Compounds (1A) to (1I) correspond to compound (1). A synthetic method of a compound having —COO— is shown in formation of ester. A compound having —OCO— can also be prepared according to the above synthetic method. A same rule applies also to any other asymmetrical bonding groups.

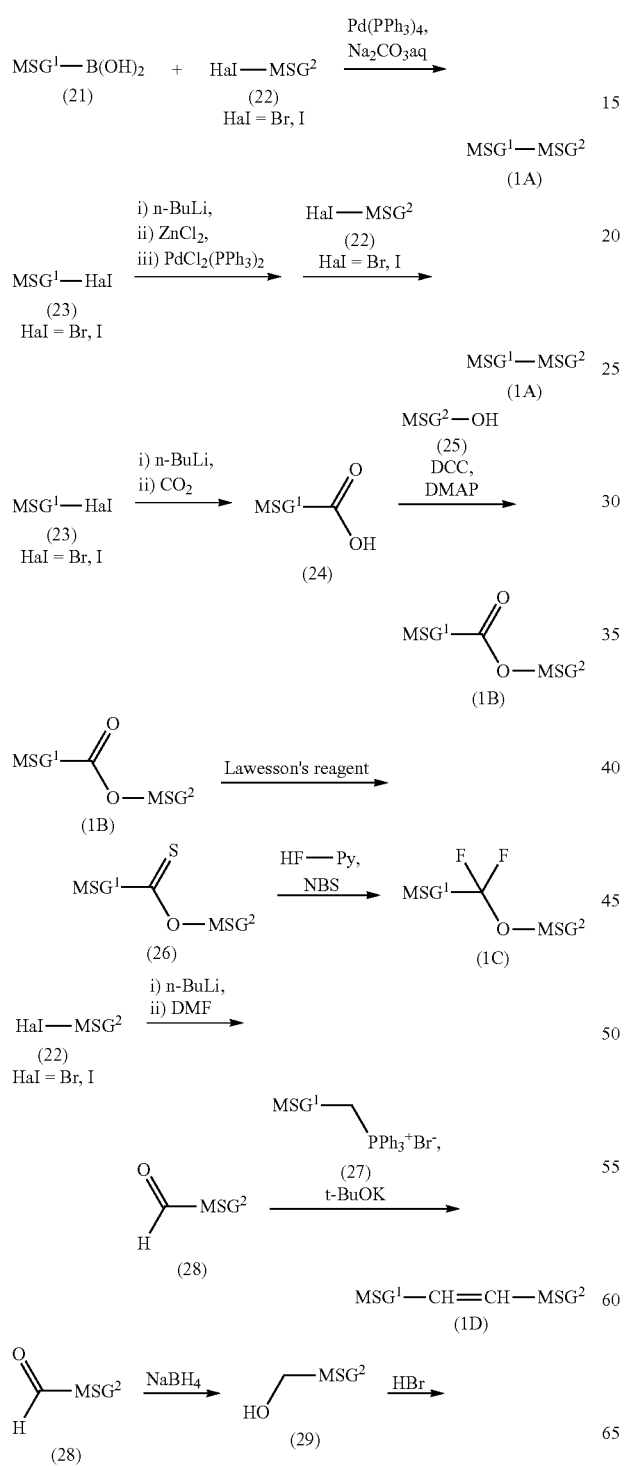

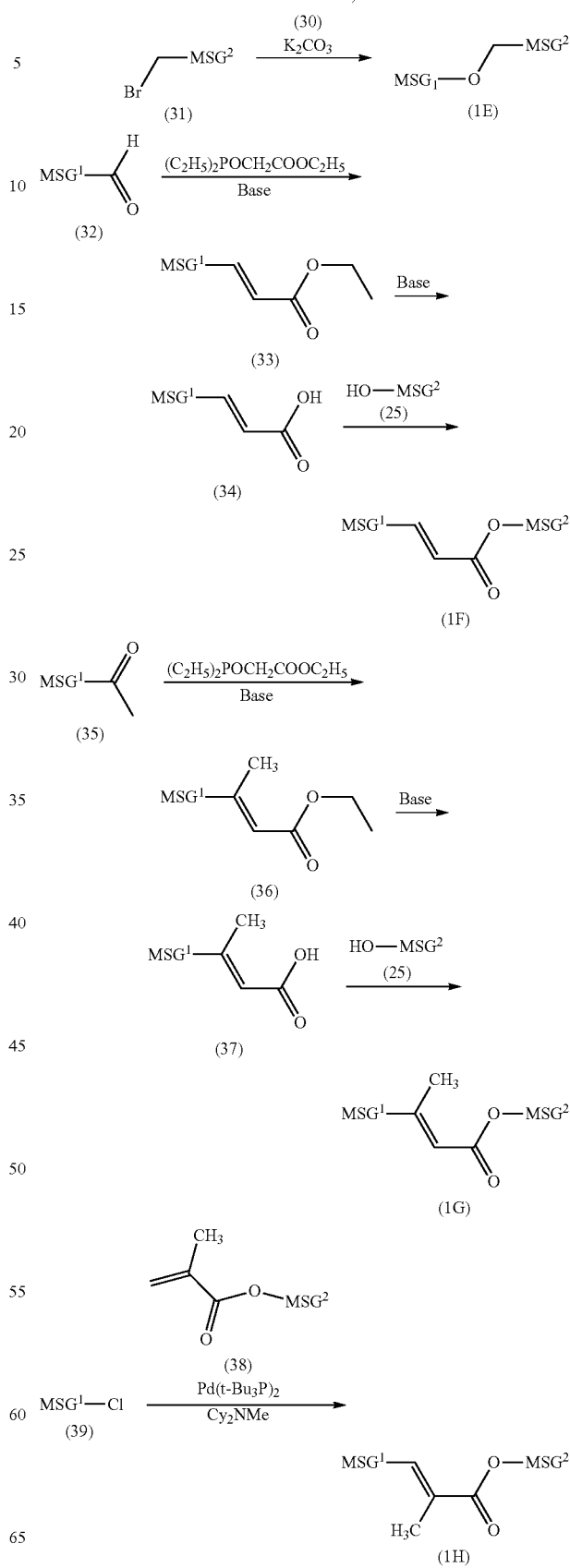

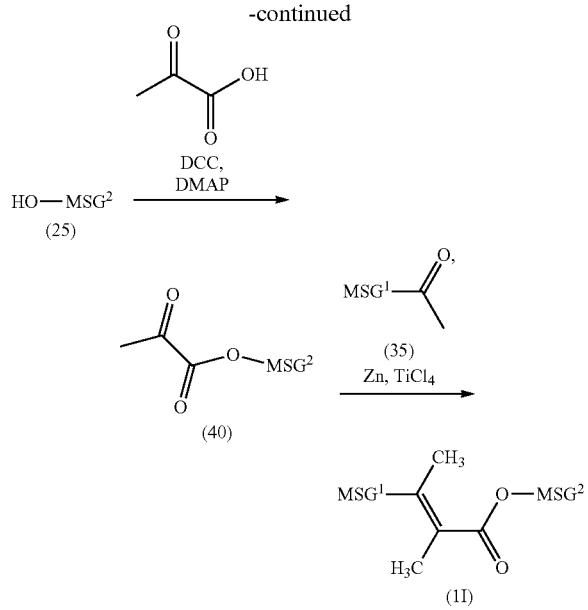

(1) Formation of a Single Bond

Compound (1 A) is prepared by allowing arylboronic acid (21) to react with compound (22) prepared according to a publicly known method in the presence of a catalyst such as tetrakis(triphenylphosphine)palladium in a carbonate aqueous solution. Compound (1A) is also prepared by allowing compound (23) prepared according to a publicly known method to react with n-butyllithium and subsequently with zinc chloride, and further with compound (22) in the presence of a catalyst such as dichlorobis(triphenylphosphine) palladium.

(2) Formation of —COO—

Carboxylic acid (24) is obtained by allowing compound (23) to react with n-butyllithium and subsequently with carbon dioxide. Compound (1B) is prepared by dehydration of compound (24) and phenol (25) prepared according to a publicly known method in the presence of 1,3-dicyclohexylcarbodiimide (DCC) and N,N-dimethyl-4-aminopyridine (DMAP).

(3) Formation of —CF$_2$O—

Compound (26) is obtained by treating compound (1B) with a thiation reagent such as Lawesson's reagent. Compound (1C) is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH=CH—

Aldehyde (28) is obtained by treating compound (22) with n-butyllithium and then allowing the treated compound to react with formamide such as N,N-dimethylformamide (DMF). Compound (1 D) is prepared by allowing phosphorus ylide generated by treating phosphonium salt (27) prepared according to a known method with a base such as potassium tert-butoxide to react with aldehyde (28). A cis isomer may be formed depending on reaction conditions, and therefore the cis isomer is isomerized into a trans isomer according to a publicly known method when necessary.

(5) Formation of —CH$_2$O—

Compound (29) is obtained by reducing compound (28) with a reducing agent such as sodium borohydride. Compound (31) is obtained by halogenating compound (29) with hydrobromic acid or the like. Compound (1E) is prepared by allowing compound (31) to react with compound (30) in the presence of potassium carbonate or the like.

(6) Formation of —CH=CH—COO—

Phosphorus ylide is prepared by allowing a base such as sodium hydride to act on diethylphosphoethyl acetate, and ester (33) is obtained by allowing the phosphorus ylide to react with aldehyde (32). Carboxylic acid (34) is obtained by hydrolyzing ester (33) in the presence of a base such as sodium hydroxide. Compound (1F) is prepared by dehydrating condensation of carboxylic acid (34) and compound (25).

(7) Formation of —C(CH$_3$)=CH—COO—

Phosphorus ylide is prepared by allowing a base such as sodium hydride to act on diethylphosphoethyl acetate, and ester (36) is obtained by allowing the phosphorus ylide to react with methyl ketone (35). Then, carboxylic acid (37) is obtained by hydrolyzing ester (36) in the presence of a base such as sodium hydroxide, and then compound (1 G) is prepared by dehydrating condensation of carboxylic acid (37) and compound (25).

(8) Formation of —CH=C(CH$_3$)—COO—

Compound (1H) is prepared by allowing compound (38) prepared according to a publicly known method to react with compound (39) prepared according to a publicly known method in the presence of a base such as N,N-dicyclohexyl methylamine (Cy$_2$NMe) and a catalyst such as bis(tri-tert-butylphosphine)palladium.

(9) Formation of —C(CH$_3$)=C(CH$_3$)—COO—

Compound (40) is obtained by dehydrating condensation of compound (25) and pyruvic acid. Compound (1I) is prepared by allowing compound (40) to react with compound (35) in the presence of zinc and titanium tetrachloride.

2-2. Formation of Connecting Group S

P$^1$ or P$^2$ is a polymerizable group. Preferred example of the polymerizable group include acryloyloxy (P-1), vinyloxy (P-2), oxiranyl (P-3) or maleimide (A). In formula (P-1), M$^1$ and M$^2$ are independently hydrogen, fluorine, methyl or trifluoromethyl.

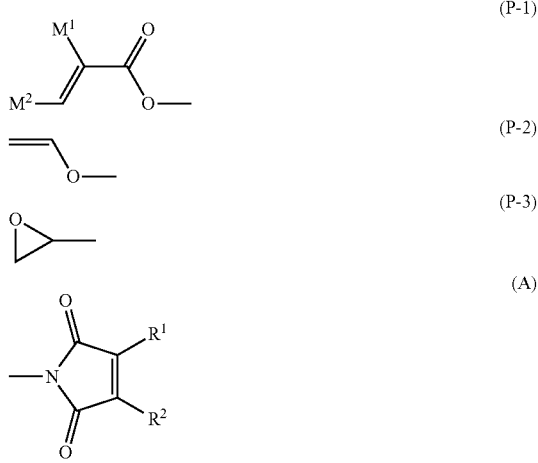

An example of a method of preparing a compound in which the polymerizable groups are connected into a ring by connecting group S is as described below. First, an example that connecting group S is a single bond is shown.

(1) Formation of a Single Bond

A method of forming a single bond is as described in the following scheme. In the scheme, $MSG^1$ (or $MSG^2$) is a monovalent organic group having at least one ring. Compounds (1A) to (1J) correspond to compound (1).

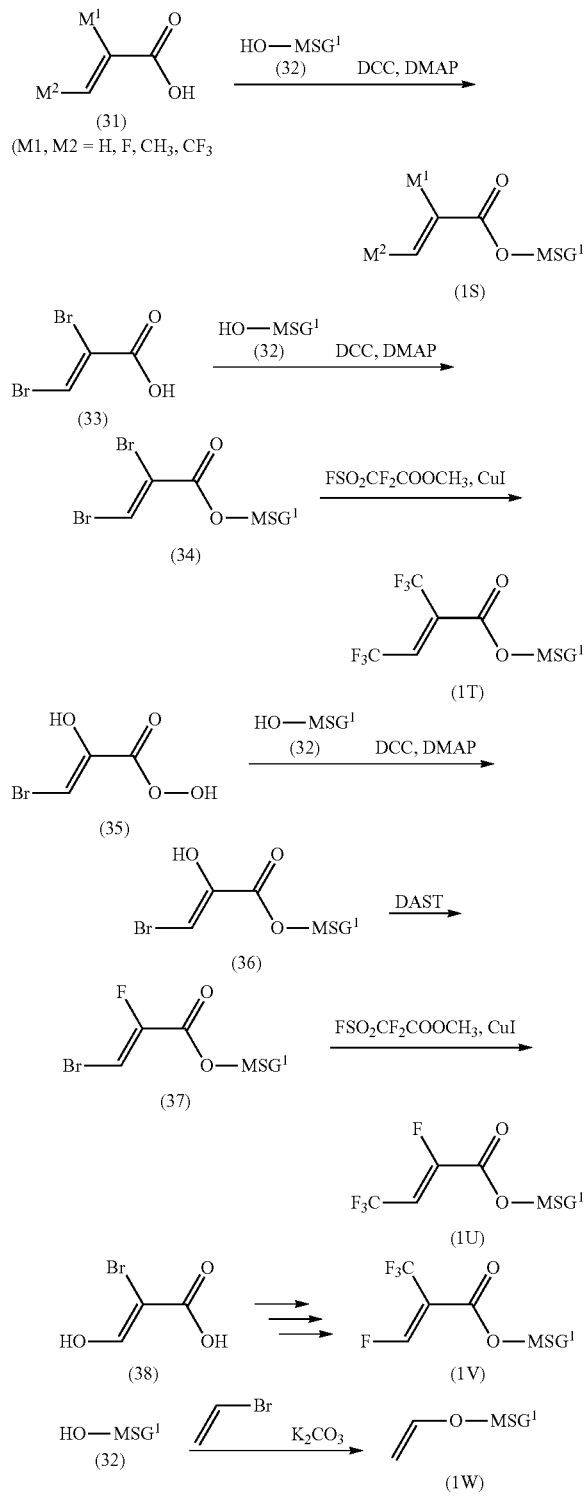

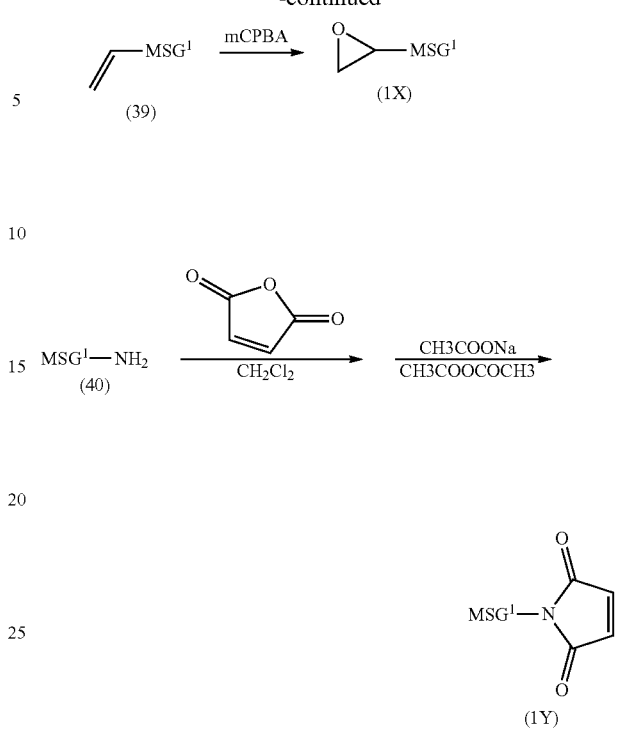

A synthetic method of a compound in which connecting group S is a single bond is described above. A method of preparing any other connecting groups can be prepared referring to the synthetic method of bonding group Z.

Compound (1) has suitable polymerization reactivity, high conversion and high solubility in the liquid crystal composition in comparison with a similar compound. Compound (1) has a suitable balance regarding at least two of the physical properties. Accordingly, compound (1) can be added to the liquid crystal composition for the PSA mode.

3. Polymerizable Composition

The polymerizable composition contains at least one of compounds (1) as a first component. A component of the composition may be only the first component. The composition may also contain any other components such as a second component and a third component. A kind of the second component or the like depends on an application of an objective polymer. The polymerizable composition may further contain any other polymerizable compound different from compound (1) as the second component. Preferred examples of any other polymerizable compound include acrylate, methacrylate, a vinyl compound, a vinyloxy compound, propenyl ether, an epoxy compound (oxirane, oxetane) and vinyl ketone. Further preferred examples include a compound having at least one acryloyloxy, and a compound having at least one methacryloyloxy. Still further preferred examples also include a compound having both acryloyloxy and methacryloyloxy.

Additional examples of any other polymerizable compound include compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer of 1 to 10; and $L^{21}$, $L^{22}$, $L^{23}$, $L^{24}$, $L^{25}$ and $L^{26}$ are independently hydrogen or fluorine.

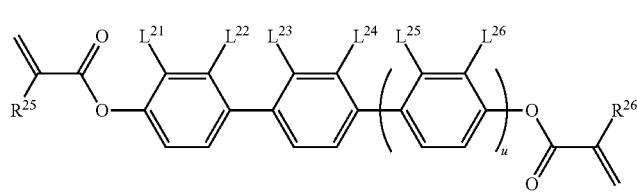
(M-1)
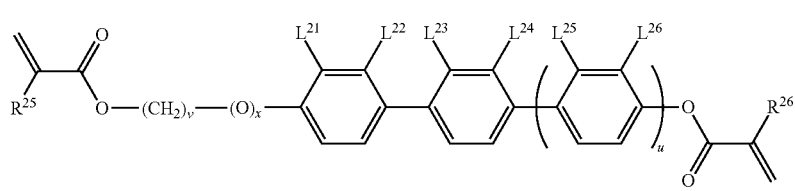
(M-2)
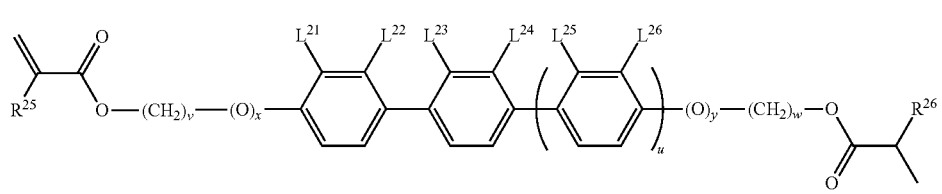
(M-3)
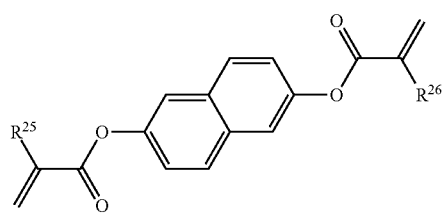
(M-4)
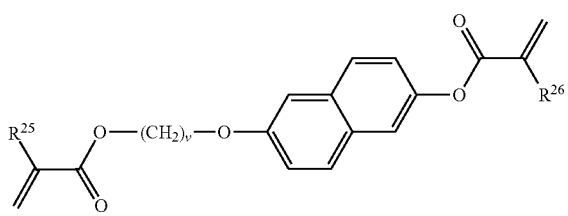
(M-5)
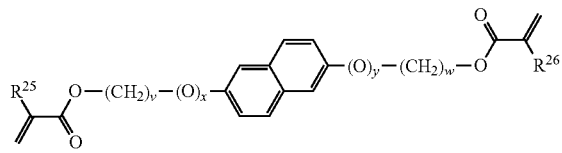
(M-6)
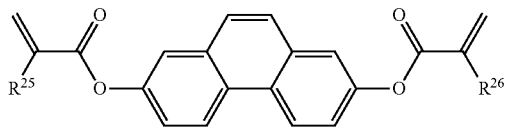
(M-7)
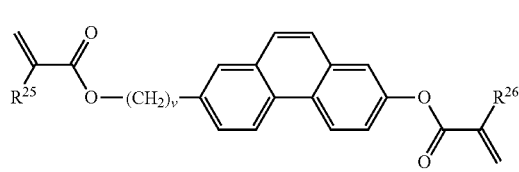
(M-8)
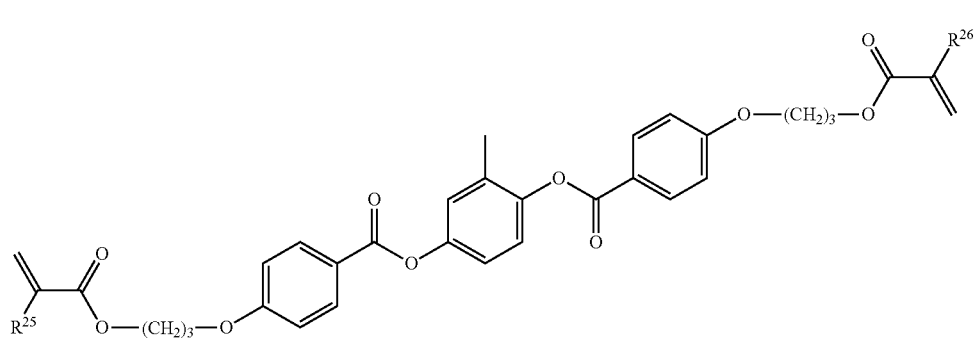
(M-9)

(M-10)

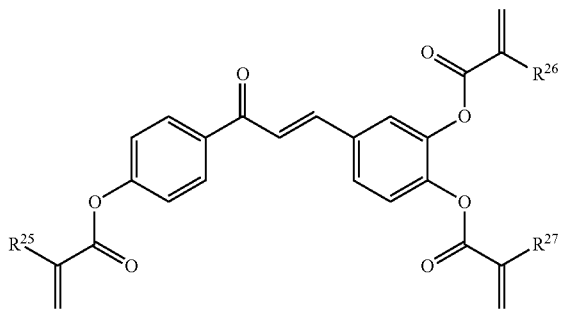

(M-11)

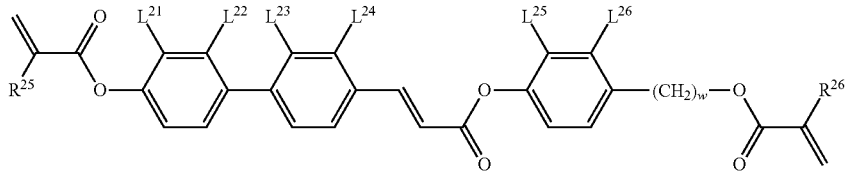

(M-12)

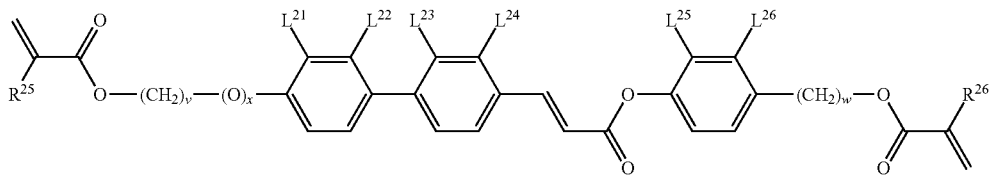

When the second component of the polymerizable composition is a polymerizable compound having a liquid crystal phase, an optical anisotropic body is formed by polymerizing the composition while controlling alignment of liquid crystal molecules. The optical anisotropic body can be used for a phase difference membrane, a polarizing device, a circularly polarizing device, an elliptically polarizing device, an antireflection film, a selective reflection film, a color compensation film, a viewing angle compensation film and so forth. An additives such as a polymerization initiator may be added to the polymerizable composition for the purpose of adjusting physical properties of the optical anisotropic body.

The polymerizable composition may also contain the liquid crystal composition as the second component. When the liquid crystal display device for the mode such as the PS-TN mode, the PS-IPS mode, the PS-FFS mode, the PSA-VA mode and the PSA-OCB mode is an objective application, the polymerizable composition preferably contains compound (1) as component A, and further contains a compound selected from components B, C and D shown below. Component B includes compounds (2) to (4). Component C includes compounds (5) to (7). Component D includes compound (8). When such a polymerizable composition is prepared, components B, C and D are preferably selected by taking the positive or negative dielectric anisotropy, magnitude of the dielectric anisotropy, and so forth into account. The polymerizable composition in which the components are appropriately selected has a high maximum temperature, a low minimum temperature, small viscosity, suitable optical anisotropy (more specifically, large optical anisotropy or small optical anisotropy), large positive or negative dielectric anisotropy, and a suitable elastic constant (more specifically, a large elastic constant or a small elastic constant).

The polymerizable composition is prepared by adding compound (1) to the liquid crystal composition. The additive may be added to the composition when necessary. In such a composition, an amount of addition of compound (1), more specifically, component A is in the range of 0.01% by weight to 20% by weight based on the weight of the liquid crystal composition. A further preferred adding amount is the range of 0.0133% by weight to 10% by weight. Most preferred adding amount is the range of 0.05% by weight to 5% by weight. At least one of any other polymerizable compounds different from compound (1) may be further added. In the above case, a total amount of addition of compound (1) and any other polymerizable compound is preferably in the range described above. The physical properties of the polymer to be formed can be adjusted by appropriately selecting any other polymerizable compound. Specific examples of any other polymerizable compound include acrylate and methacrylate as described above. The examples also include compounds (M-1) to (M-12).

Component B includes a compound in which two terminal groups are alkyl or the like. Preferred examples of component B include compounds (2-1) to (2-11), compounds (3-1) to (3-19) or compounds (4-1) to (4-7). In the compound of component B, $R^{11}$ and $R^{12}$ are independently alkyl having 1 to 10 carbons or alkenyl having 2 to 10 carbons, and in the alkyl or the alkenyl, at least one —$CH_2$— may be replaced by —O—, and at least one hydrogen may be replaced by fluorine.

(2-1)

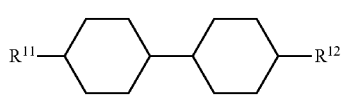

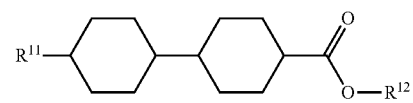 (2-2)
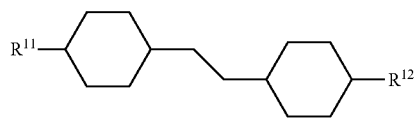 (2-3)
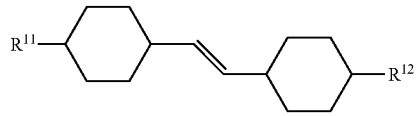 (2-4)
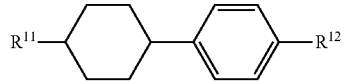 (2-5)
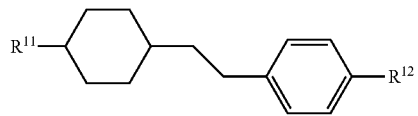 (2-6)
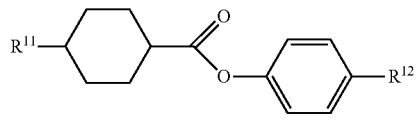 (2-7)
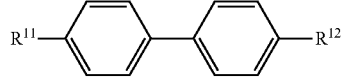 (2-8)
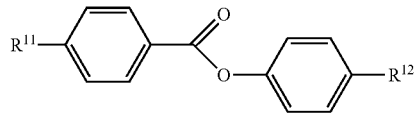 (2-9)
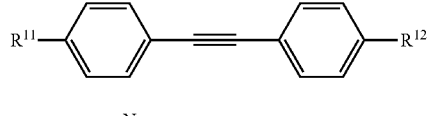 (2-10)
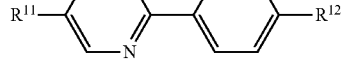 (2-11)
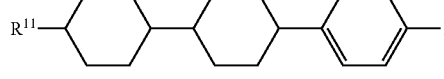 (3-1)
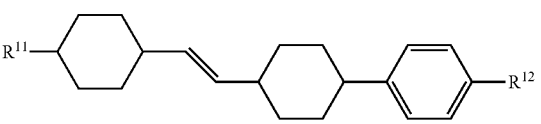 (3-2)
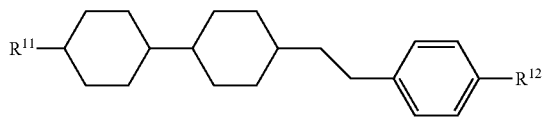 (3-3)
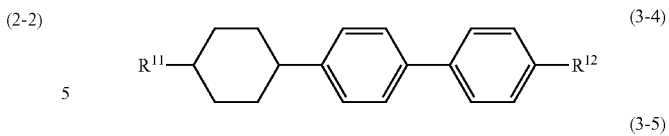 (3-4)
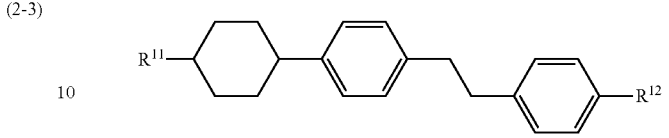 (3-5)
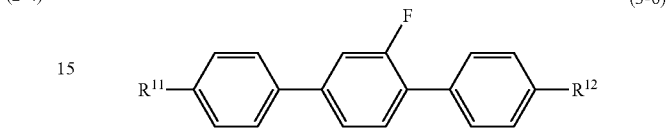 (3-6)
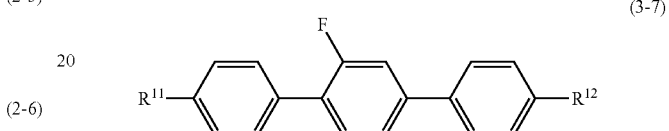 (3-7)
 (3-8)
 (3-9)
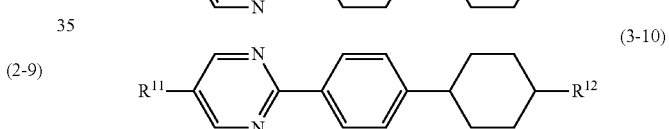 (3-10)
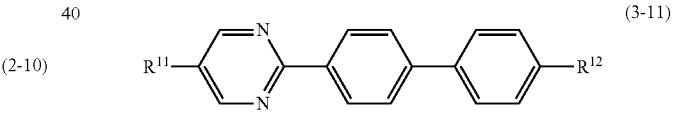 (3-11)
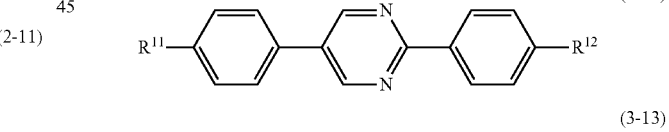 (3-12)
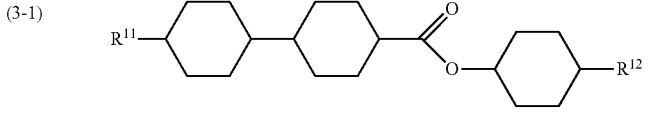 (3-13)
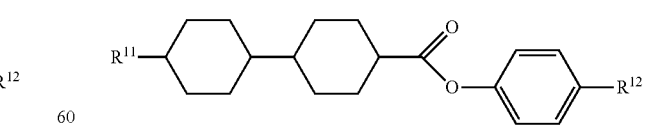 (3-14)
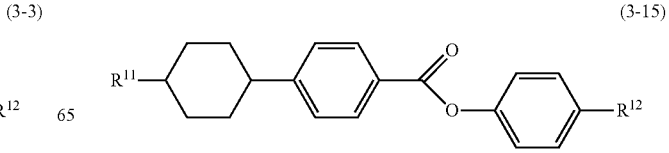 (3-15)

-continued

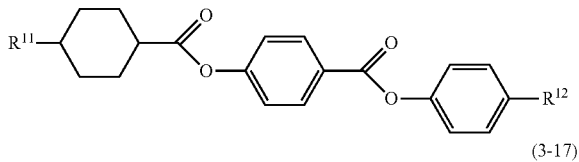
(3-16)

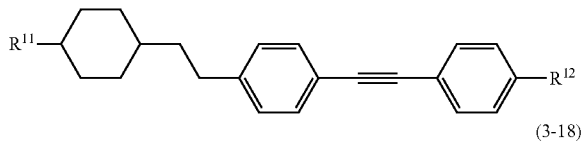
(3-17)

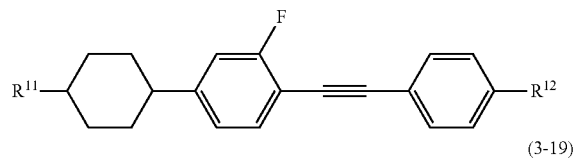
(3-18)

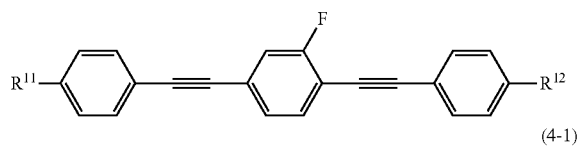
(3-19)

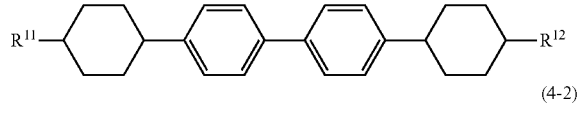
(4-1)

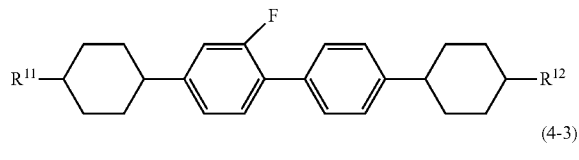
(4-2)

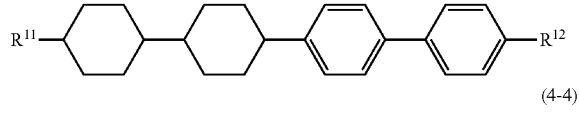
(4-3)

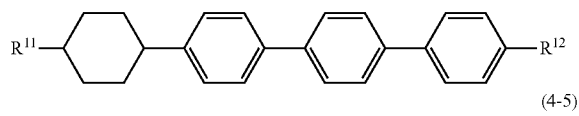
(4-4)

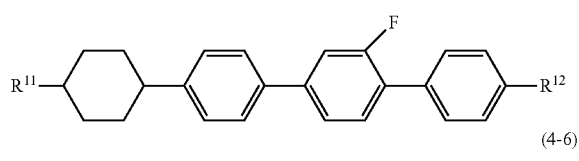
(4-5)

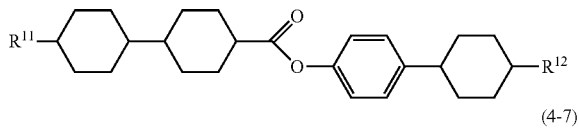
(4-6)

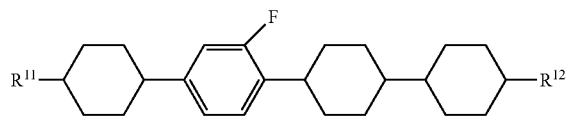
(4-7)

Component B has a small absolute value of the dielectric anisotropy, and therefore is a compound close to neutrality. Compound (2) is effective mainly in adjusting the viscosity or effective in adjusting the optical anisotropy. Compounds (3) and (4) are effective in extending the temperature range of the nematic phase by increasing the maximum temperature, or effective in adjusting the optical anisotropy.

As a content of component B is increased, the dielectric anisotropy of the composition is decreased, but the viscosity is decreased. Thus, as long as a desired value of a threshold voltage of the device is met, the content is preferably as large as possible. Accordingly, when the composition for the mode such as the PS-IPS mode and the PSA-VA mode is prepared, the content of component B is preferably 30% by weight or more, and further preferably 40% by weight or more, based on the weight of the liquid crystal composition.

Component C is a compound having a halogen-containing group or a fluorine-containing group at a right terminal. Preferred examples of component C include compounds (5-1) to (5-16), compounds (6-1) to (6-113) and compounds (7-1) to (7-57). In the compound of component C, $R^{13}$ is alkyl having 1 to 10 carbons or alkenyl having 2 to 10 carbons, and in the alkyl and the alkenyl, at least one piece of —$CH_2$— may be replaced by —O—, and at least one hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

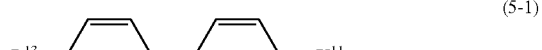
(5-1)

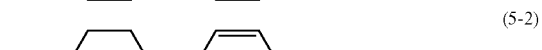
(5-2)

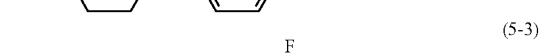
(5-3)

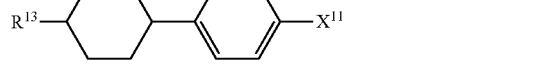
(5-4)

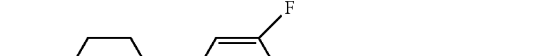
(5-5)

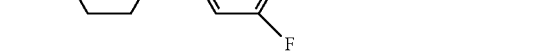
(5-6)

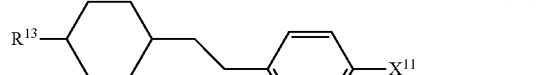
(5-7)

(5-8)

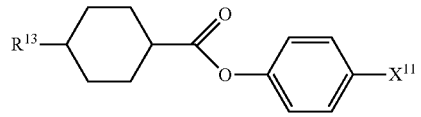

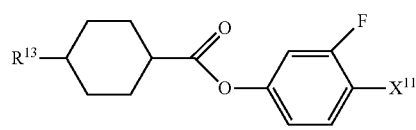 (5-9)
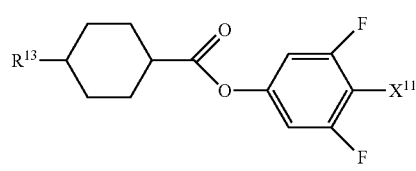 (5-10)
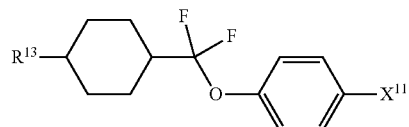 (5-11)
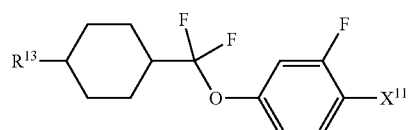 (5-12)
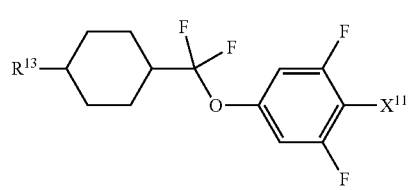 (5-13)
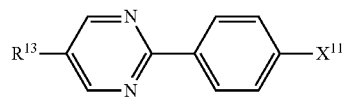 (5-14)
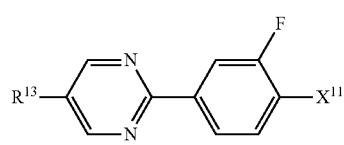 (5-15)
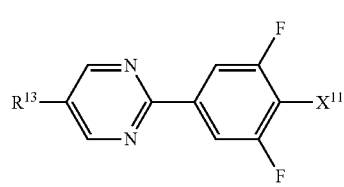 (5-16)
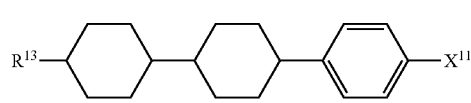 (6-1)
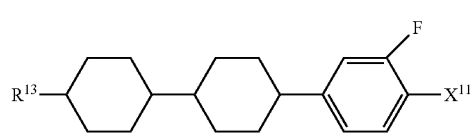 (6-2)
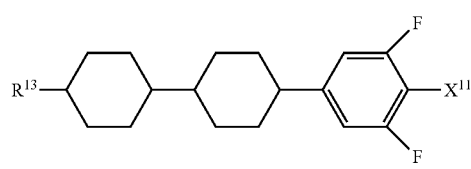 (6-3)
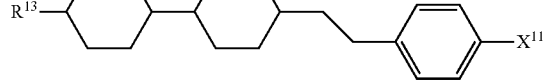 (6-4)
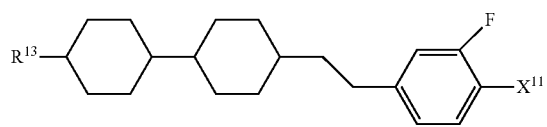 (6-5)
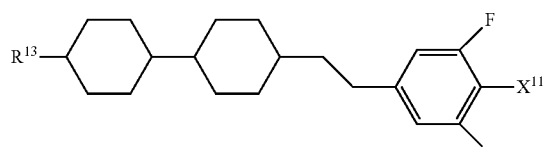 (6-6)
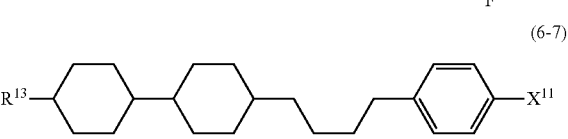 (6-7)
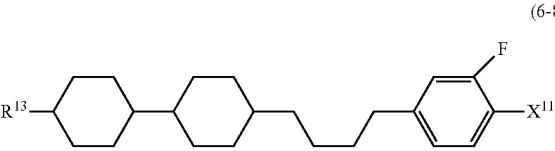 (6-8)
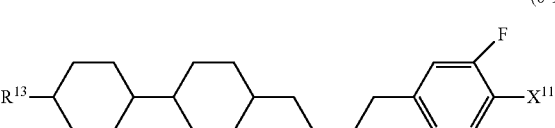 (6-9)
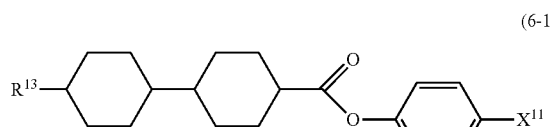 (6-10)
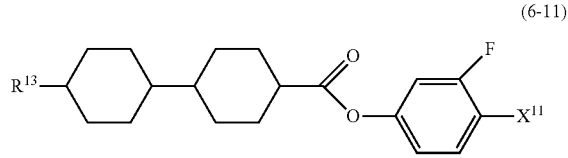 (6-11)
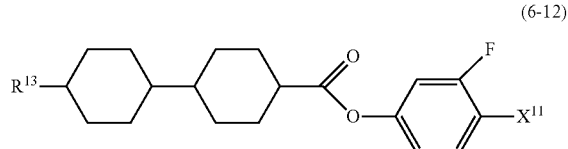 (6-12)
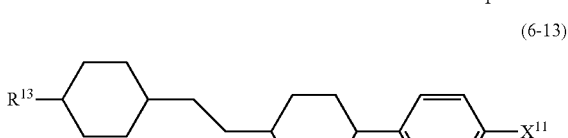 (6-13)

(6-14) 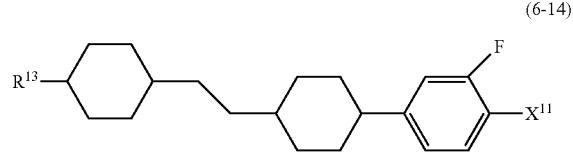
(6-15) 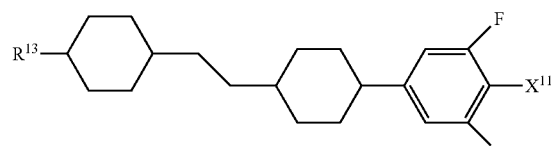
(6-16) 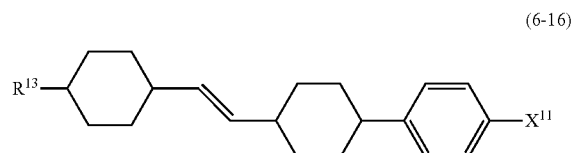
(6-17) 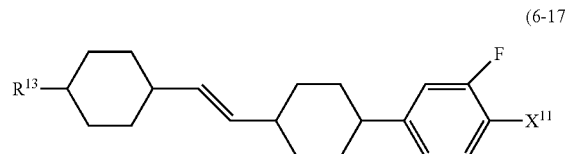
(6-18) 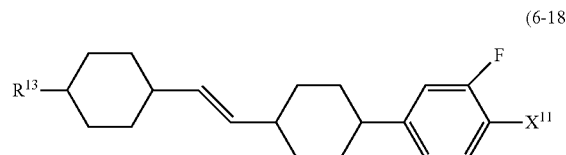
(6-19) 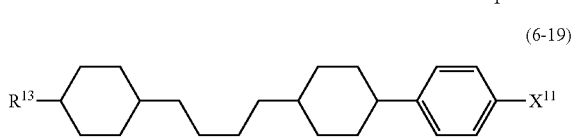
(6-20) 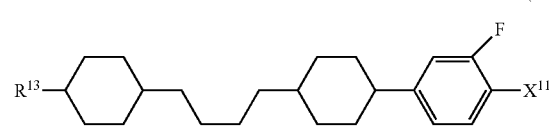
(6-21) 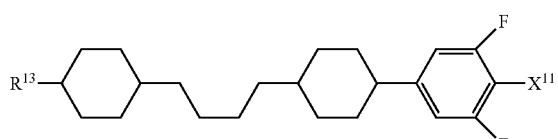
(6-22) 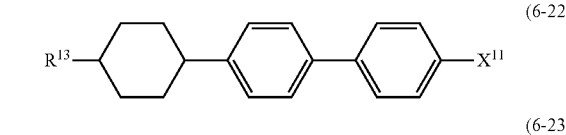
(6-23) 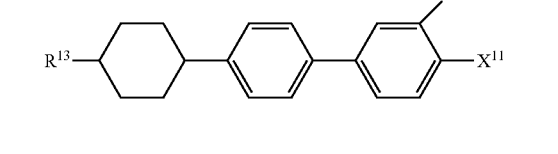
(6-24) 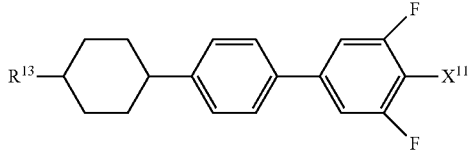
(6-25) 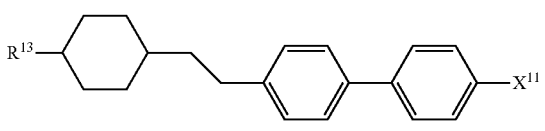
(6-26) 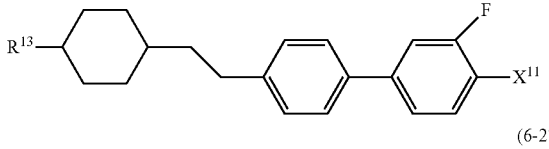
(6-27) 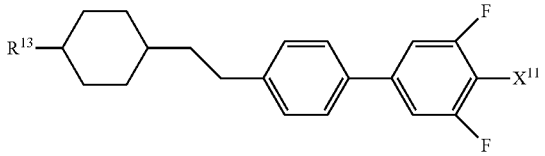
(6-28) 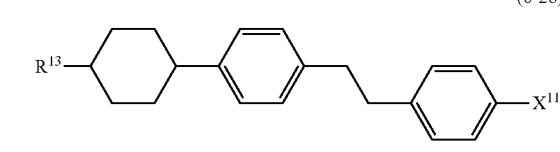
(6-29) 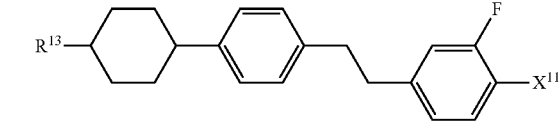
(6-30) 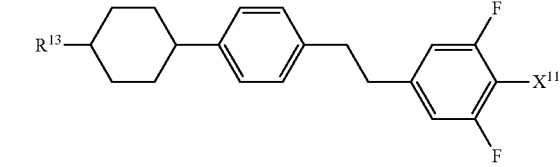
(6-31) 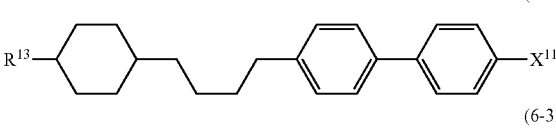
(6-32) 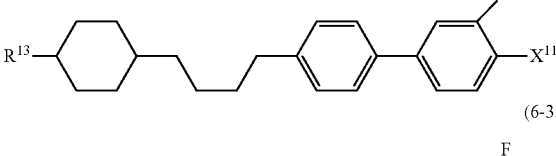
(6-33) 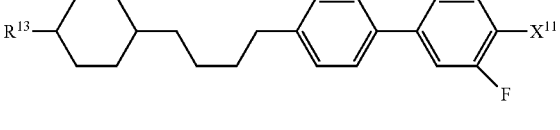

(6-34) 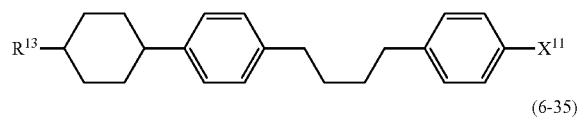
(6-35) 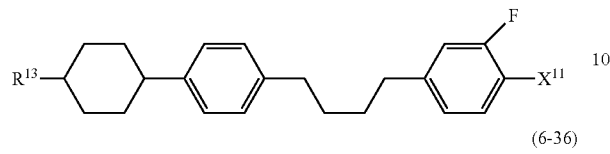
(6-36) 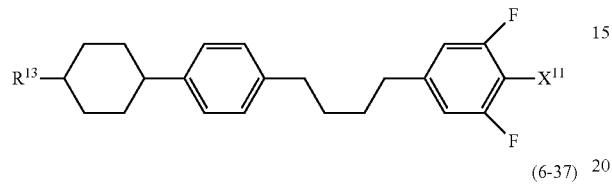
(6-37) 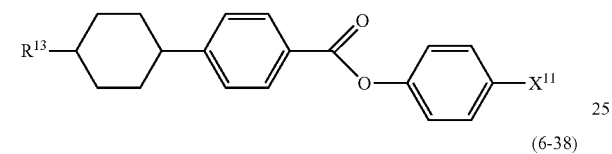
(6-38) 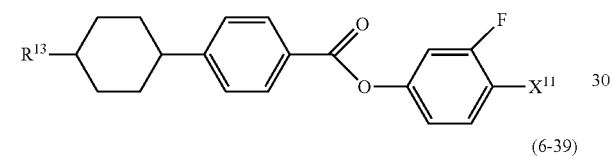
(6-39) 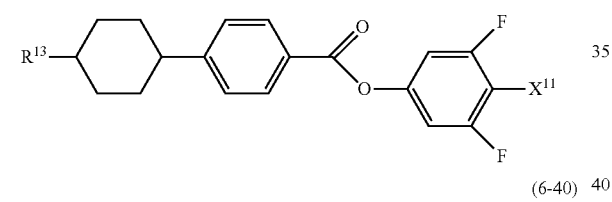
(6-40) 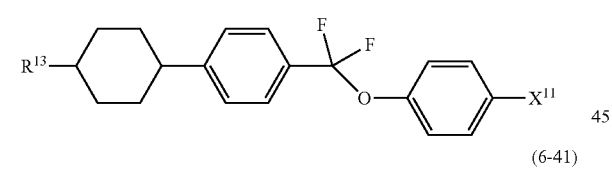
(6-41) 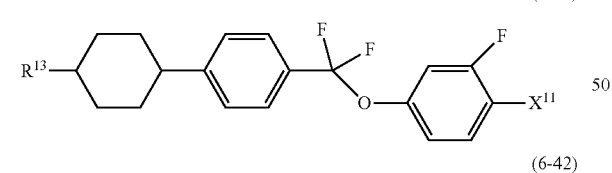
(6-42) 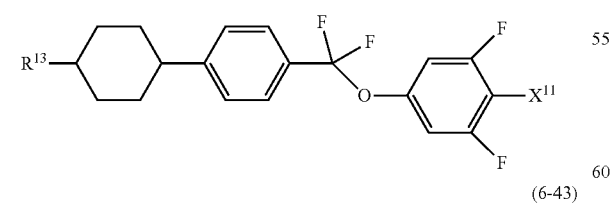
(6-43) 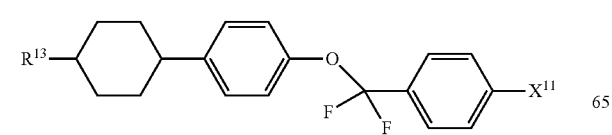
(6-44) 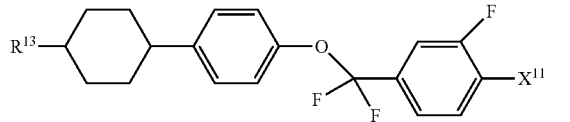
(6-45) 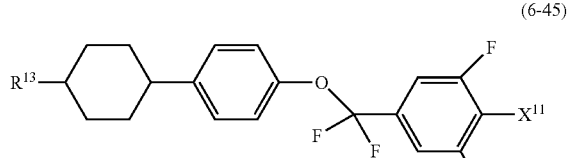
(6-46) 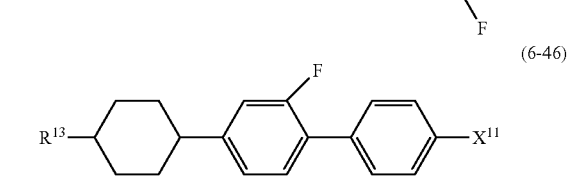
(6-47) 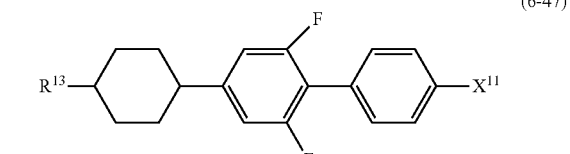
(6-48) 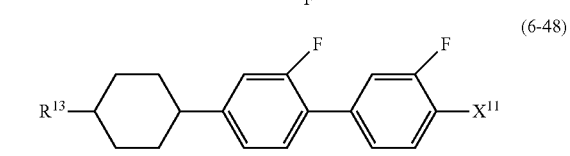
(6-49) 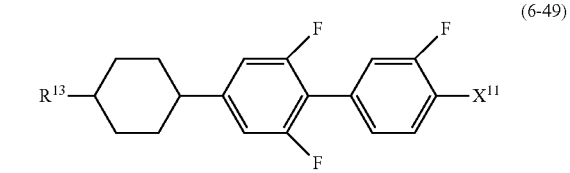
(6-50) 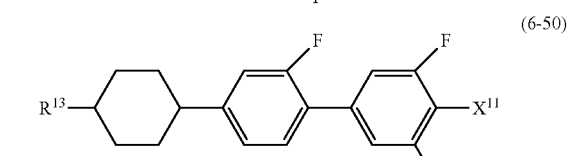
(6-51) 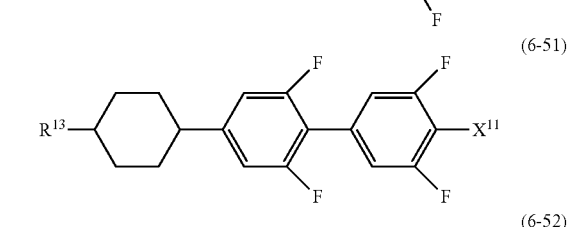
(6-52) 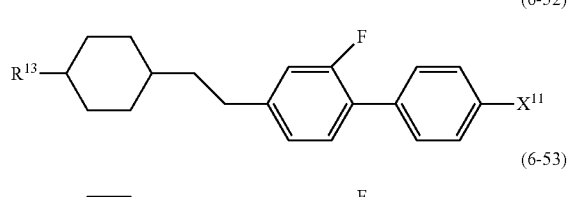
(6-53) 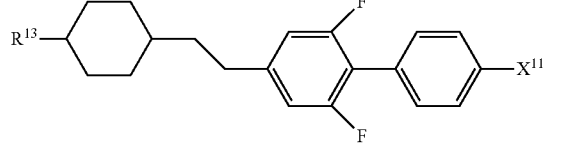

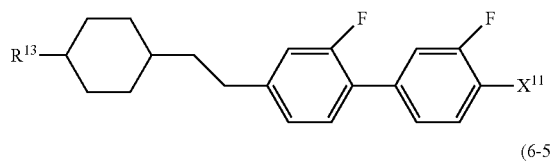
(6-54)
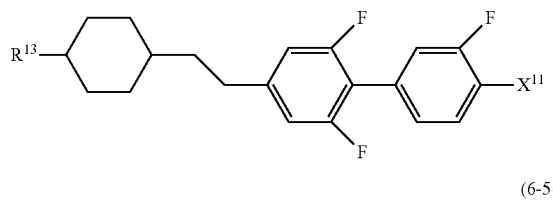
(6-55)
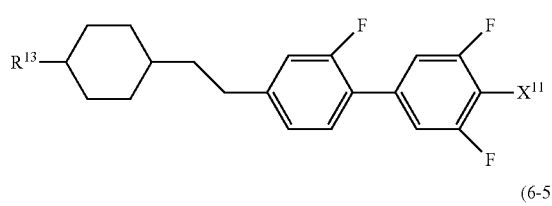
(6-56)
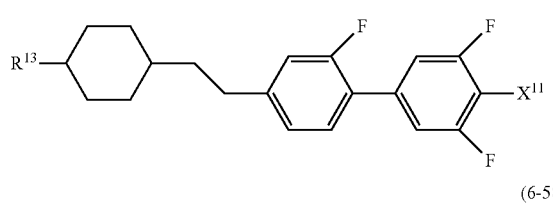
(6-57)
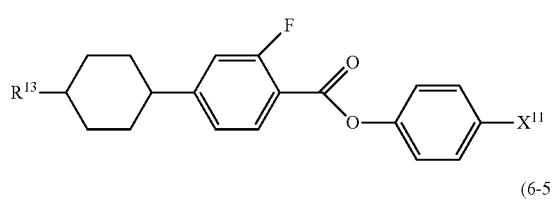
(6-58)
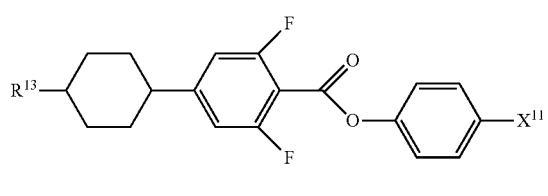
(6-59)
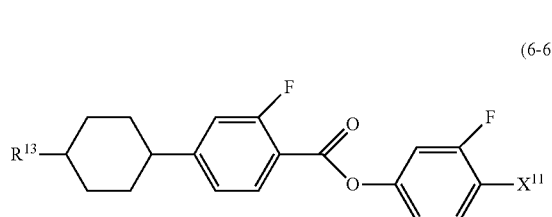
(6-60)
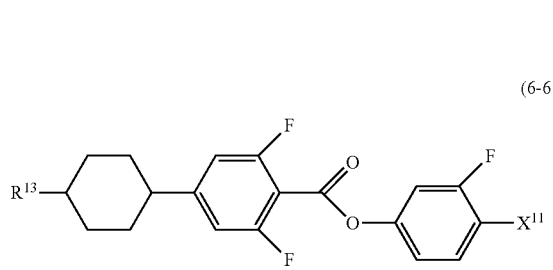
(6-61)
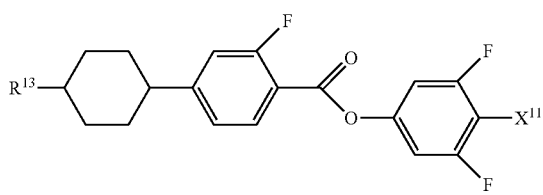
(6-62)
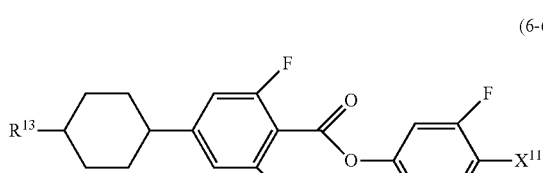
(6-63)
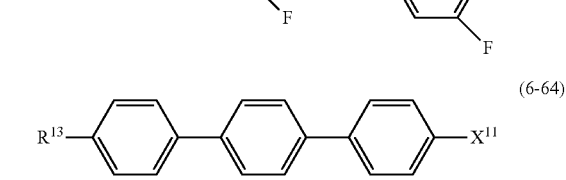
(6-64)
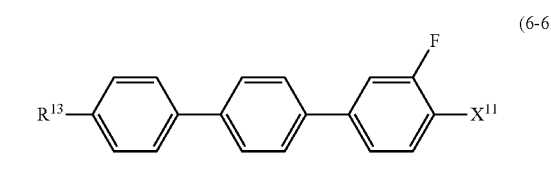
(6-65)
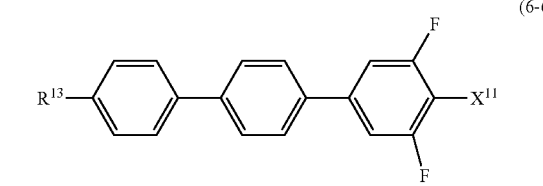
(6-66)
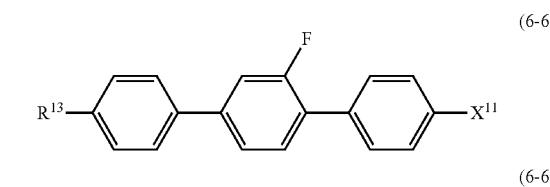
(6-67)
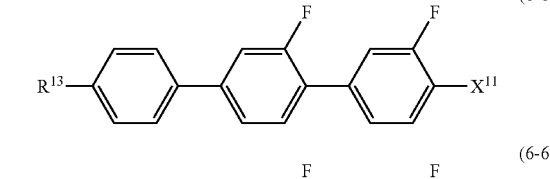
(6-68)
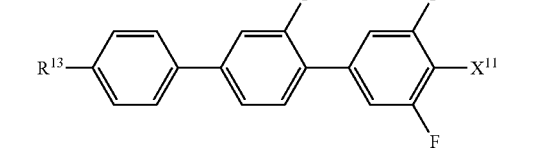
(6-69)
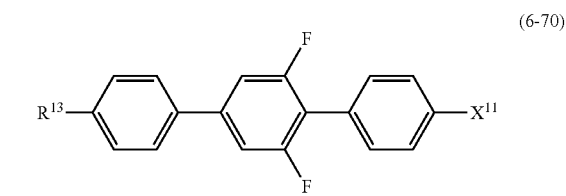
(6-70)

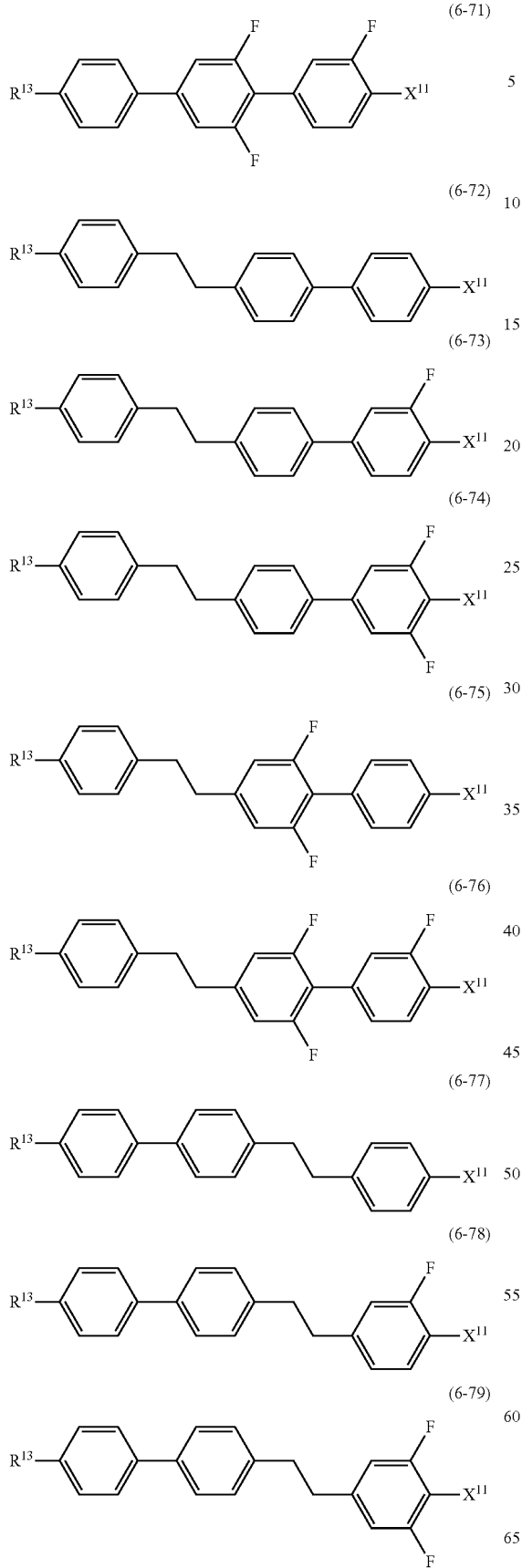
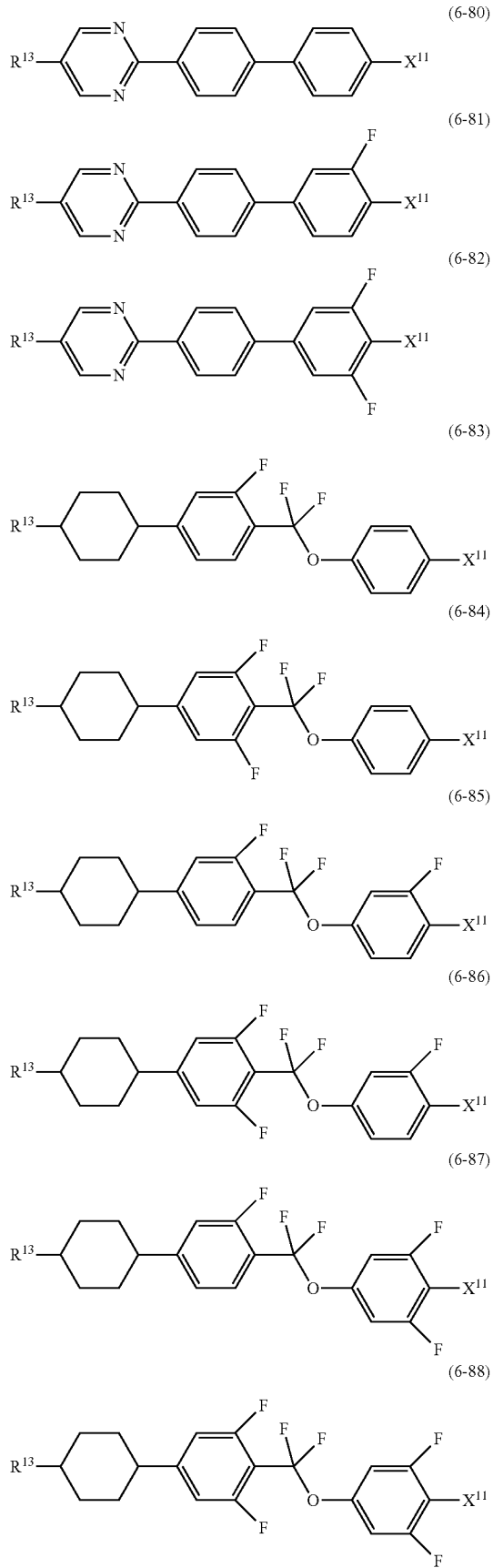

(6-89) 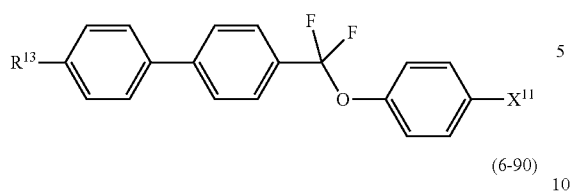
(6-90) 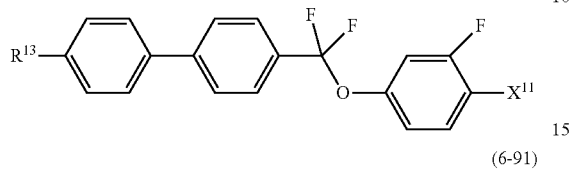
(6-91) 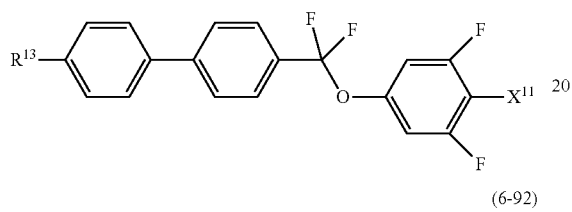
(6-92) 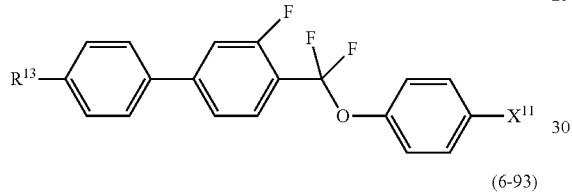
(6-93) 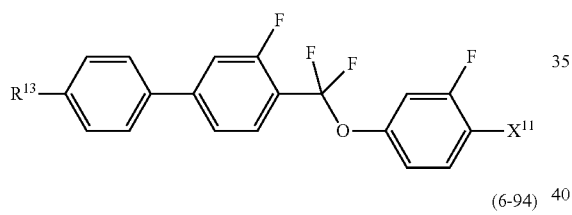
(6-94) 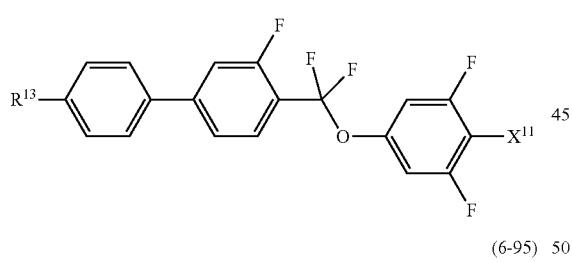
(6-95) 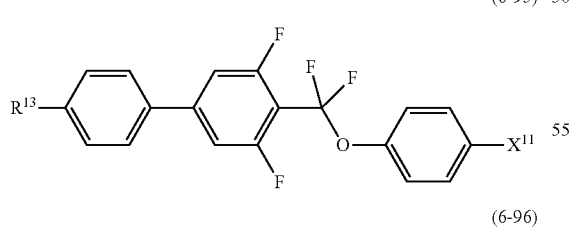
(6-96) 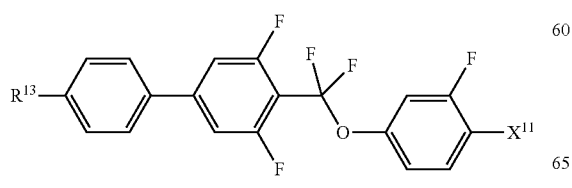
(6-97) 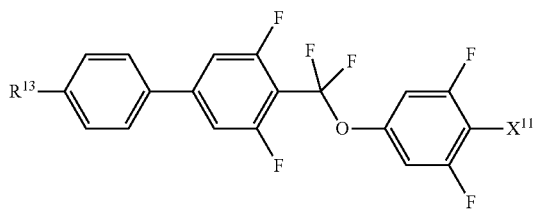
(6-98) 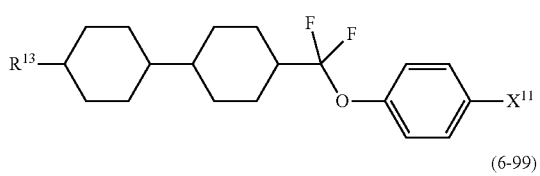
(6-99) 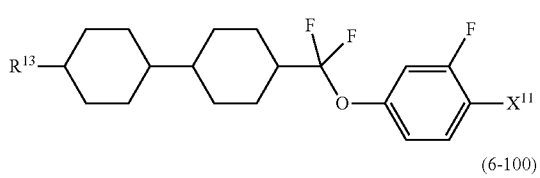
(6-100) 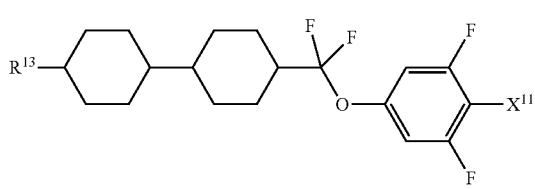
(6-101) 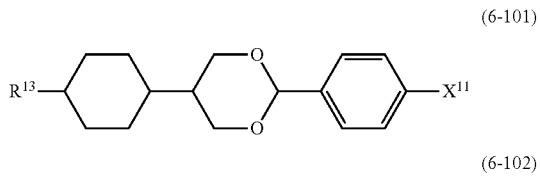
(6-102) 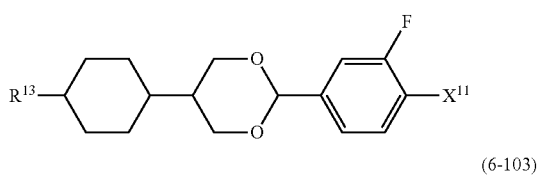
(6-103) 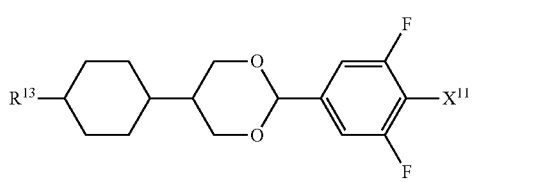
(6-104) 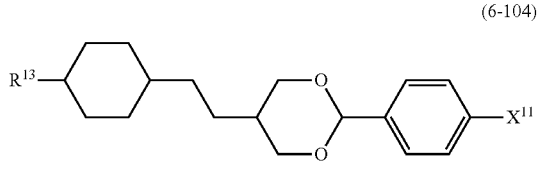
(6-105) 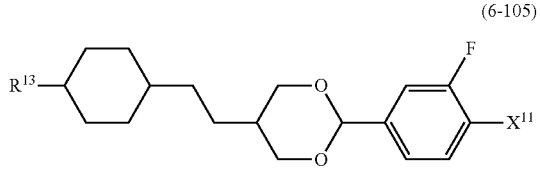

(6-106)
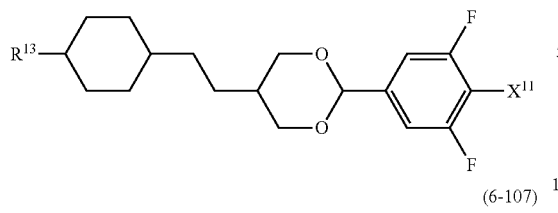
(6-107)
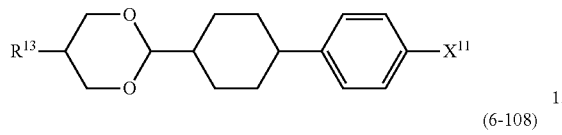
(6-108)
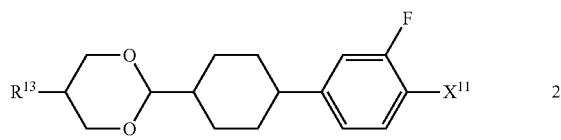
(6-109)
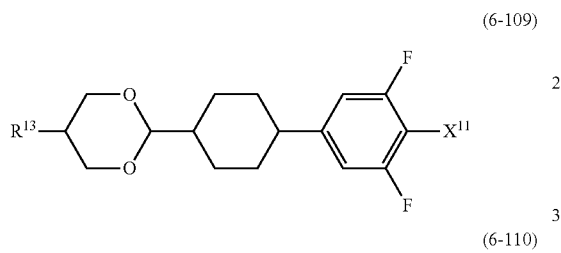
(6-110)
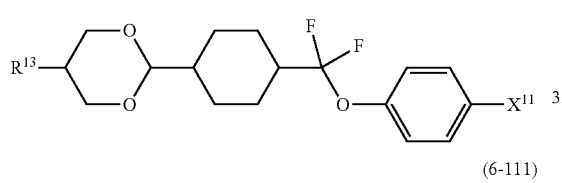
(6-111)
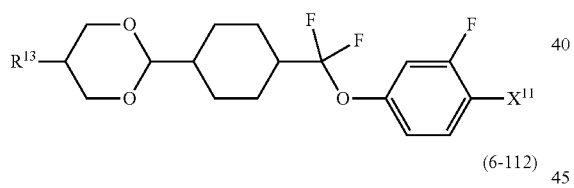
(6-112)
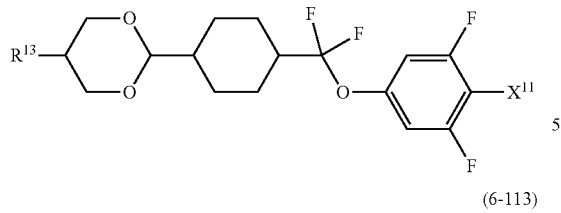
(6-113)
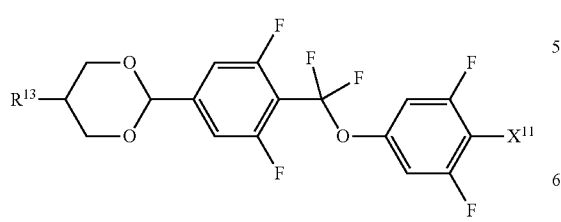
(7-1)
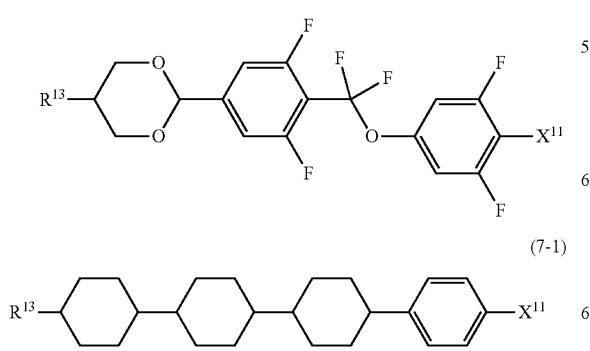
(7-2)
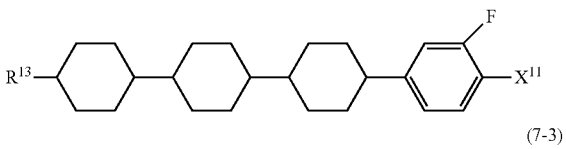
(7-3)
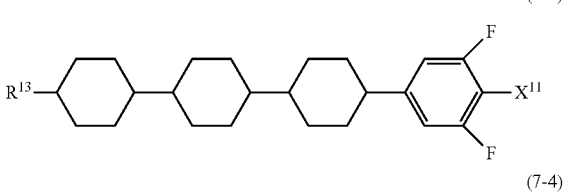
(7-4)
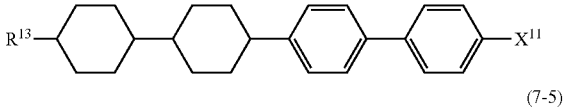
(7-5)
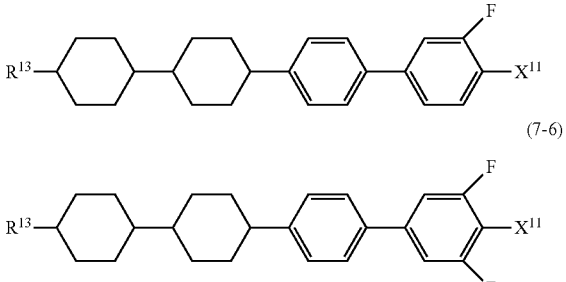
(7-6)
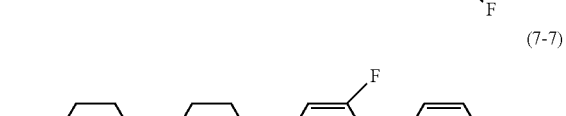
(7-7)
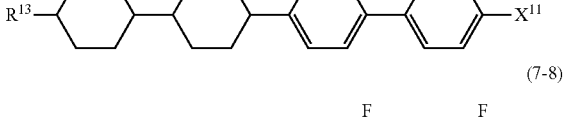
(7-8)
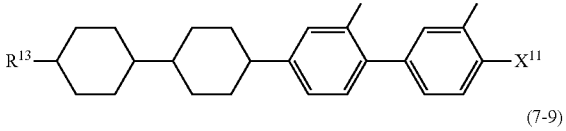
(7-9)
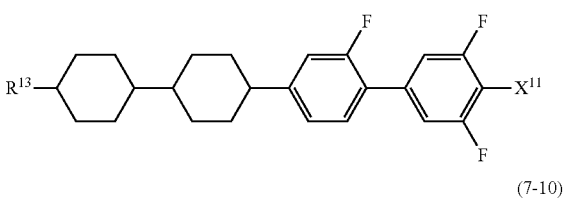
(7-10)
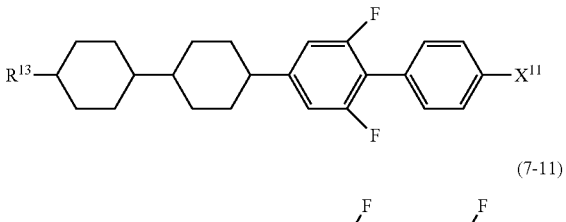
(7-11)
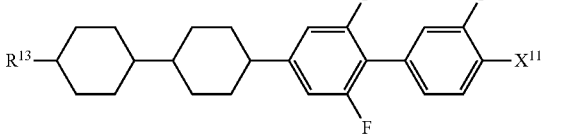

(7-12) 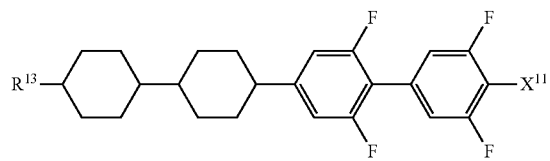
(7-13) 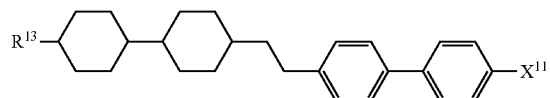
(7-14) 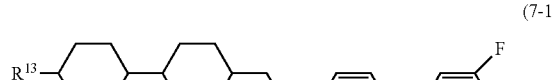
(7-15) 
(7-16) 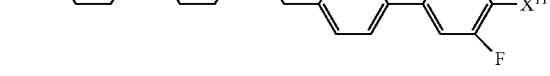
(7-17) 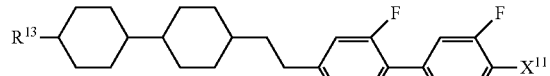
(7-18) 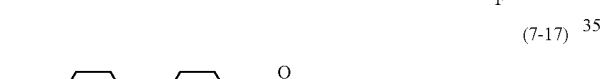
(7-19) 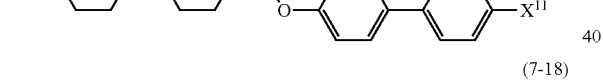
(7-20) 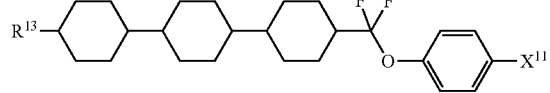
(7-21) 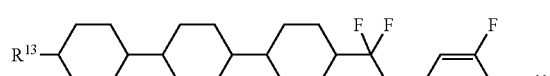
(7-22) 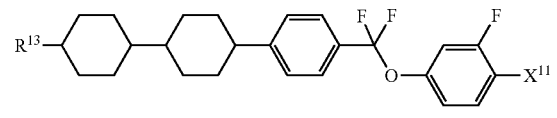
(7-23) 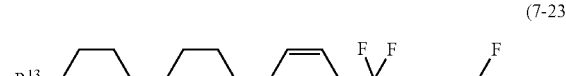
(7-24) 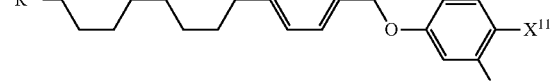
(7-25) 
(7-26) 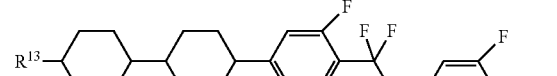
(7-27) 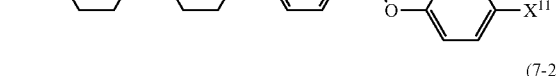
(7-28) 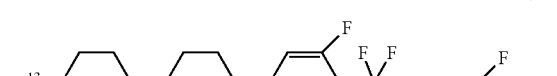
(7-29) 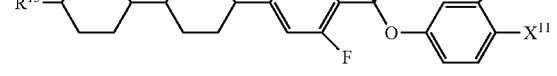
(7-30) 

(7-48)
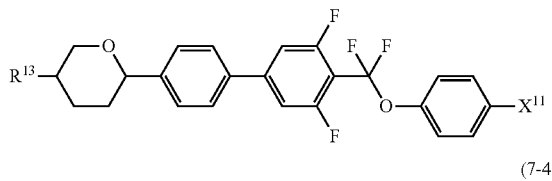

(7-49)
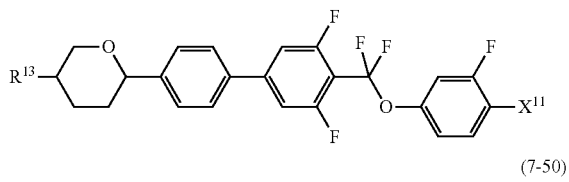

(7-50)
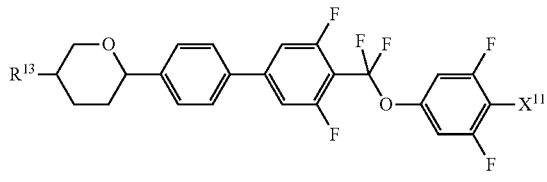

(7-51)
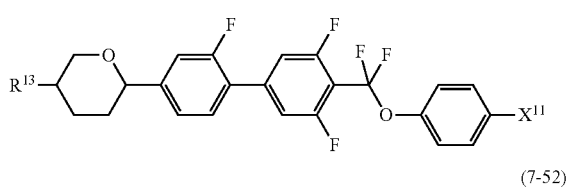

(7-52)
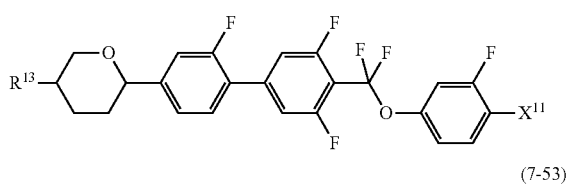

(7-53)
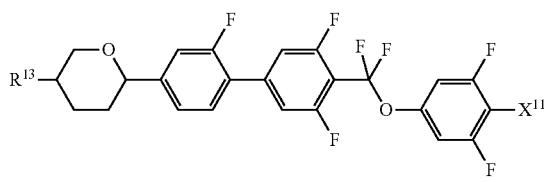

(7-54)
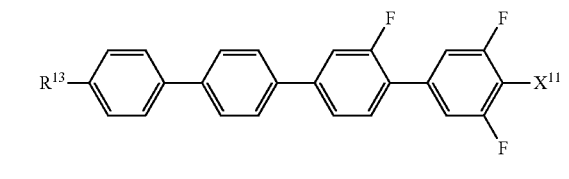

(7-55)
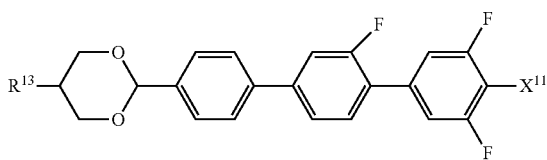

(7-56)
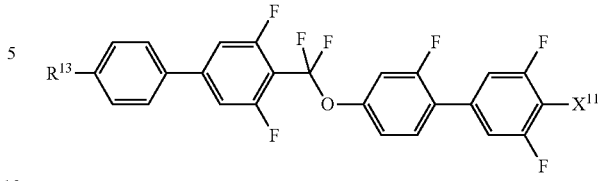

(7-57)
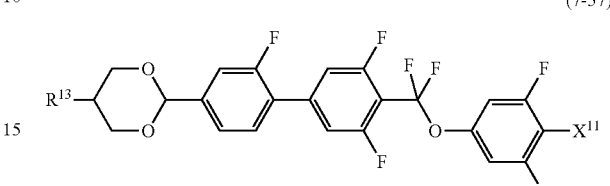

Component C has the positive dielectric anisotropy, and superb stability to heat, light and so forth, and therefore is used when the composition for the mode such as the PS-IPS mode, the PS-FFS mode and the PSA-OCB mode is prepared. A content of component C is suitably in the range of 1% by weight to 99% by weight, preferably in the range of 10% by weight to 97% by weight, and further preferably in the range of 40% by weight to 95% by weight, based on the weight of the liquid crystal composition. When component C is added to a composition having the negative dielectric anisotropy, the content of component C is preferably 30% by weight or less based on the weight of the liquid crystal composition. Addition of component C allows adjustment of the elastic constant of the composition and adjustment of a voltage-transmittance curve of the device.

Component D is compound (8) in which a right-terminal group is —C≡N or —C≡C—C≡N. Preferred examples of component D include compounds (8-1) to (8-64). In the compound of component D, $R^{14}$ is alkyl having 1 to 10 carbons or alkenyl having 2 to 10 carbons, and in the alkyl and the alkenyl, at least one piece of —CH$_2$— may be replaced by —O—, and at least one hydrogen may be replaced by fluorine; and $X^{12}$ is —C≡N or —C≡C—C≡N.

(8-1)
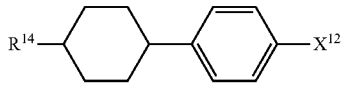

(8-2)
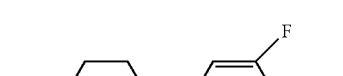

(8-3)
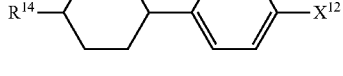

(8-4)
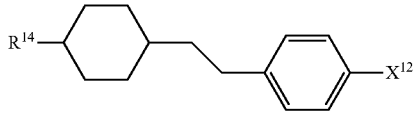

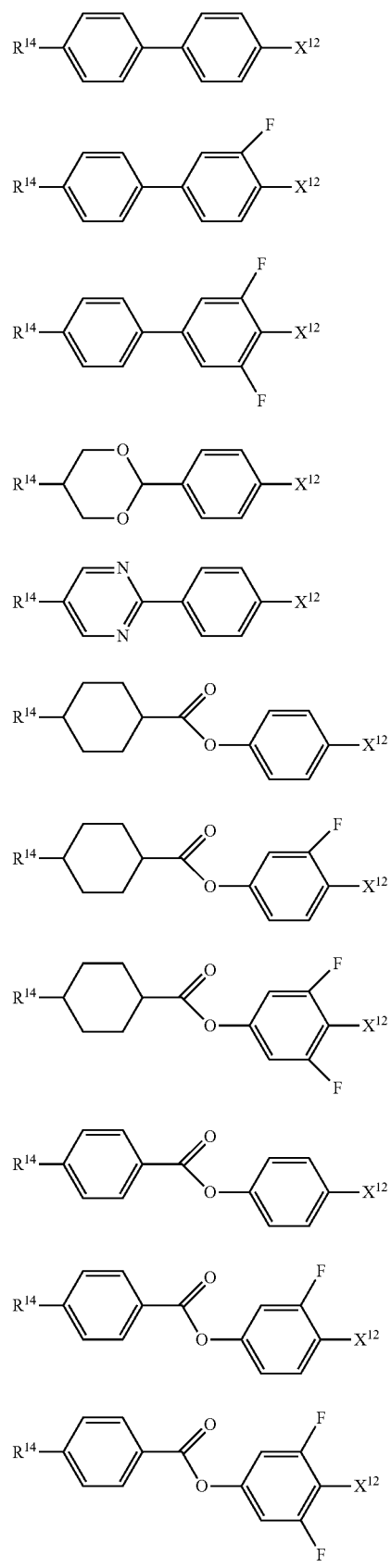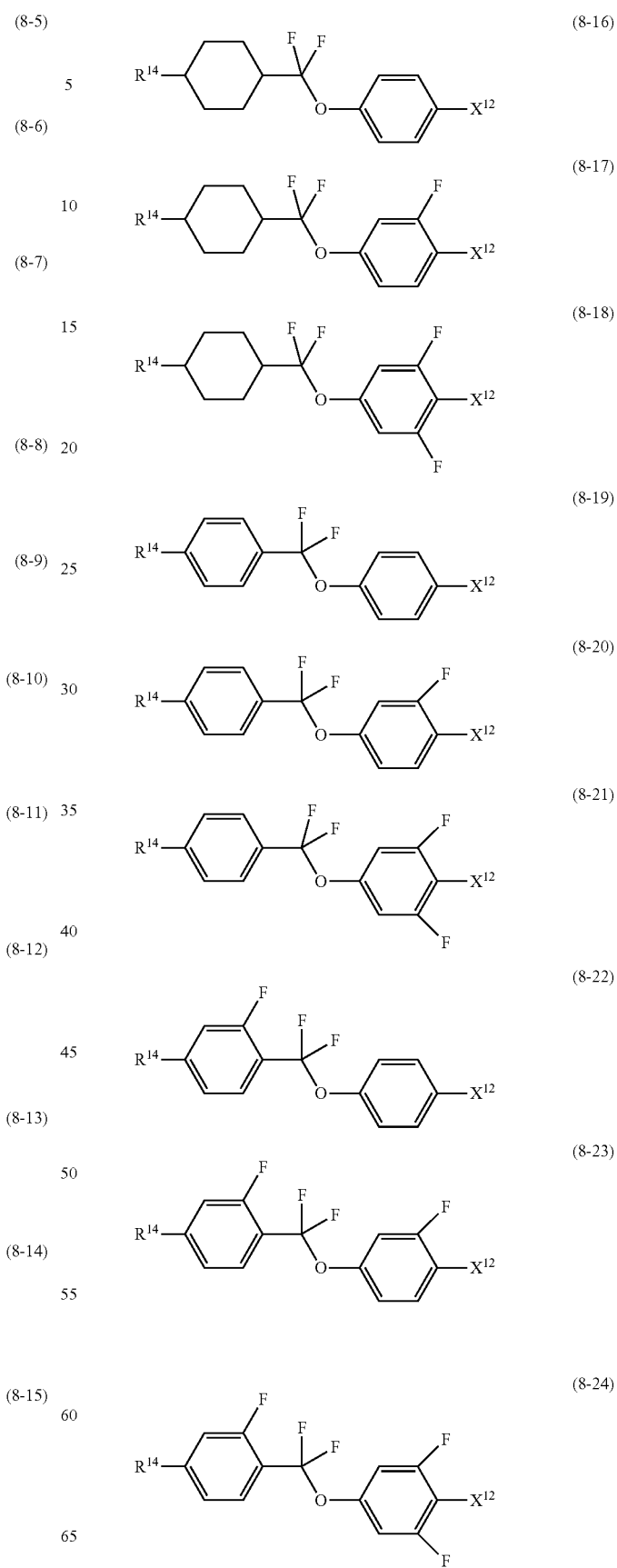

-continued
(8-25)
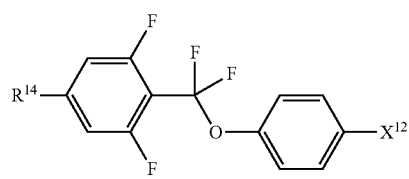
(8-26)
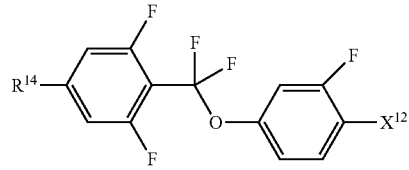
(8-27)
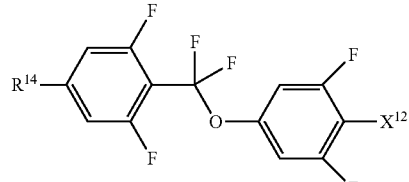
(8-28)
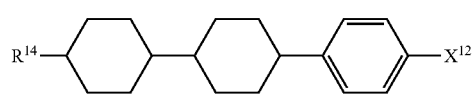
(8-29)
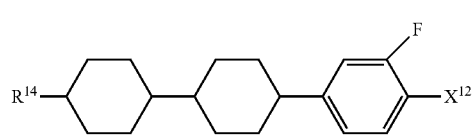
(8-30)
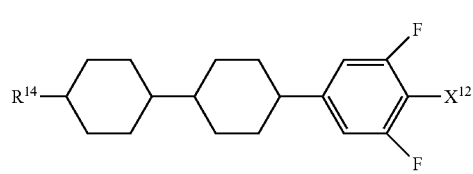
(8-31)
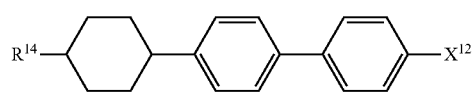
(8-32)
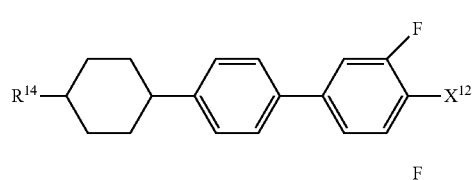
(8-33)
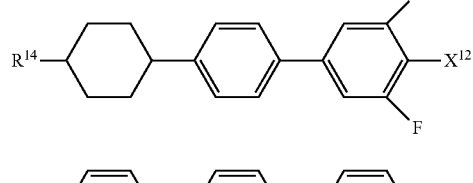
(8-34)
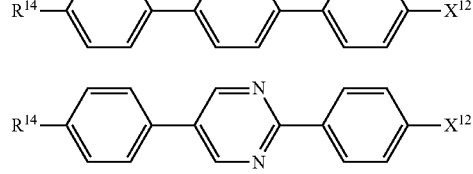
(8-35)
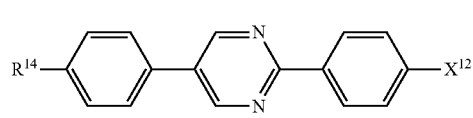
-continued
(8-36)
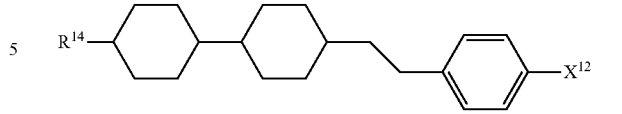
(8-37)
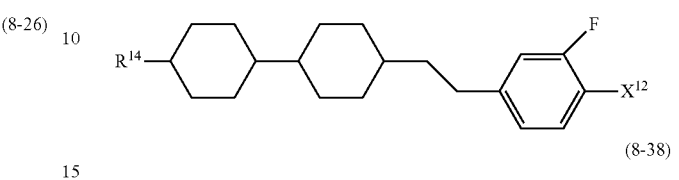
(8-38)
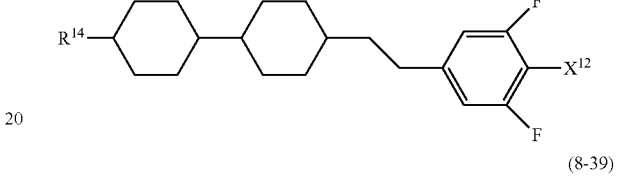
(8-39)
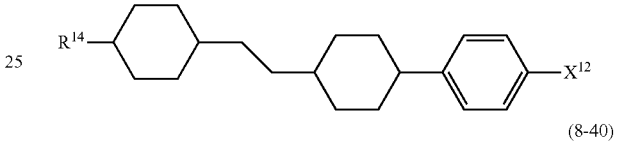
(8-40)
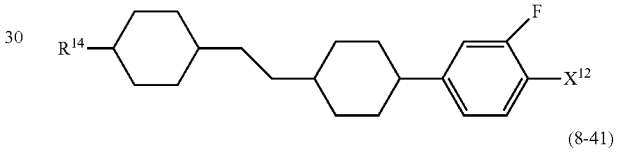
(8-41)
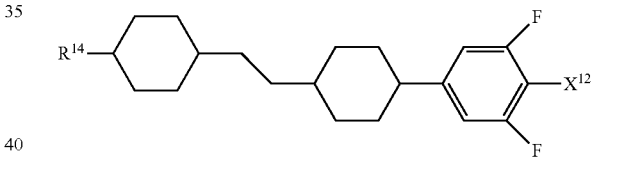
(8-42)
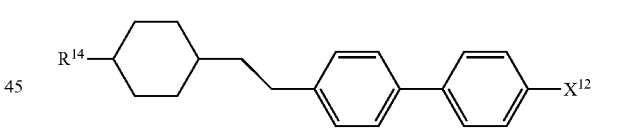
(8-43)
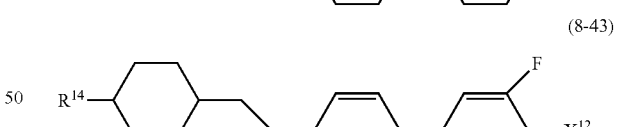
(8-44)
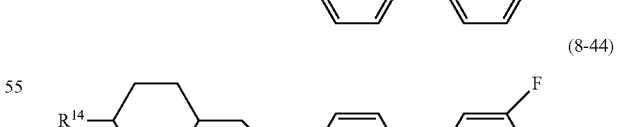
(8-45)
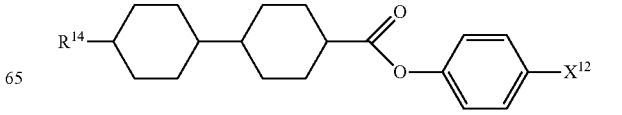

(8-46) 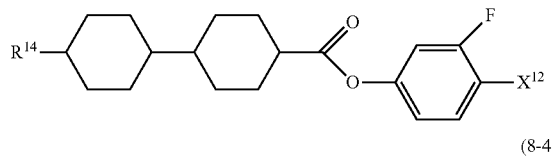
(8-47) 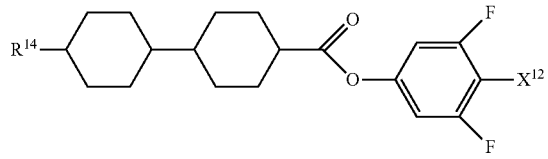
(8-48) 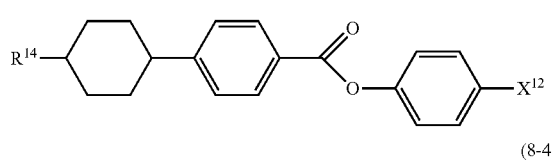
(8-49) 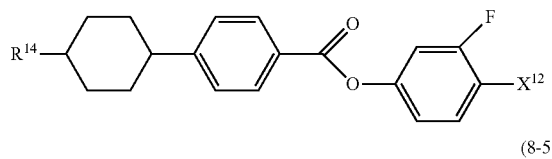
(8-50) 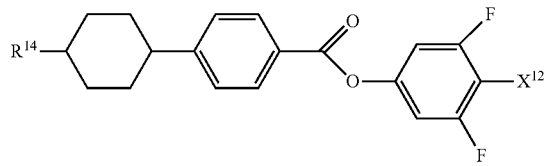
(8-51) 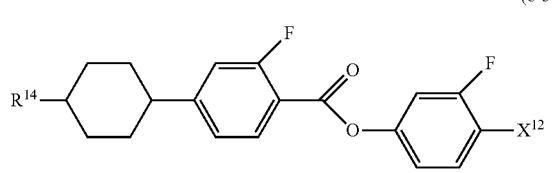
(8-52) 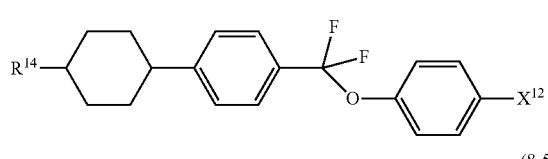
(8-53) 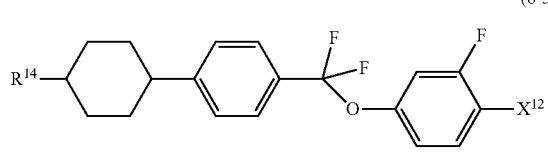
(8-54) 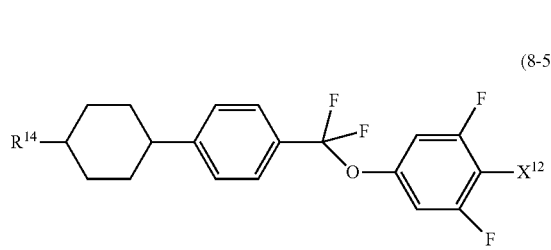
(8-55) 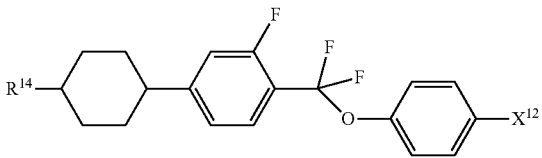
(8-56) 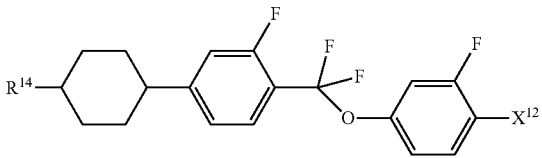
(8-57) 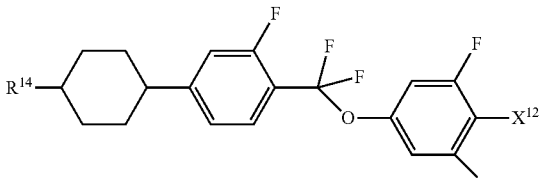
(8-58) 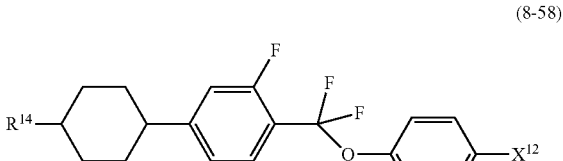
(8-59) 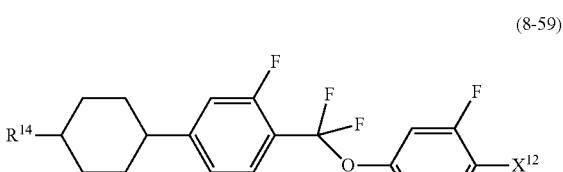
(8-60) 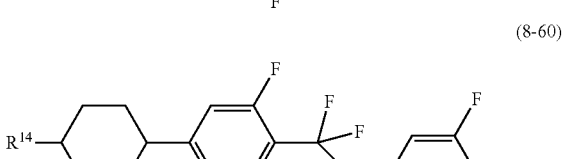
(8-61) 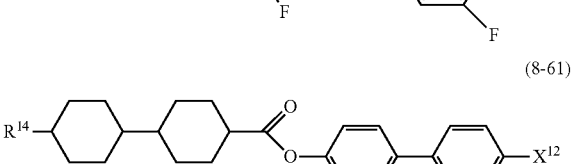
(8-62) 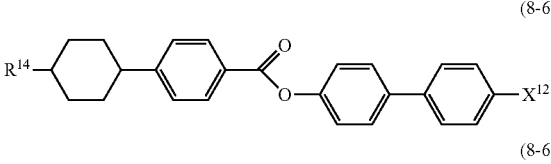
(8-63) 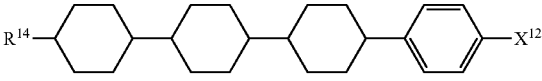

-continued (8-64)

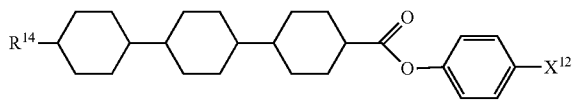

Component D has the positive dielectric anisotropy and a value thereof is large, and therefore is mainly used when the composition for the mode such as the PS-TN is prepared. The dielectric anisotropy of the composition can be increased by adding component D thereto. Component D is effective in extending the temperature range of the liquid crystal phase, adjusting the viscosity or adjusting the optical anisotropy. Component D is also useful for adjustment of the voltage-transmittance curve of the device.

When the composition for the mode such as the PS-TN mode is prepared, a content of component D is suitably in the range of 1% by weight to 99% by weight, preferably in the range of 10% by weight to 97% by weight, and further preferably in the range of 40% by weight to 95% by weight, based on the weight of the liquid crystal composition. When component D is added to the composition having the negative dielectric anisotropy, the content of component D is preferably 30% by weight or less based on the weight of the liquid crystal composition. Addition of component D allows adjustment of the elastic constant of the composition and adjustment of the voltage-transmittance curve of the device.

The polymerizable composition is prepared according to a method of dissolving a required component at a higher temperature than room temperature, for instance. According to an application, an additive may be added to the composition. Specific examples of the additive include the optically active compound, the antioxidant, the ultraviolet light absorber, the light stabilizer, the heat stabilizer, the antifoaming agent, the polymerization initiator and the polymerization inhibitor. Such additives are well known to those skilled in the art, and described in literature.

The optically active compound is effective in inducing helical structure in liquid crystal molecules to give a required twist angle, and thereby preventing a reverse twist. A helical pitch can be adjusted by adding the optically active compound thereto. Two or more optically active compounds may be added for the purpose of adjusting temperature dependence of the helical pitch. Preferred examples of the optically active compound include compounds (Op-1) to (Op-18) described below. In compound (Op-18), ring J is 1,4-cycloxylene or 1,4-phenylene, and $R^{28}$ is alkyl having 1 to 10 carbons.

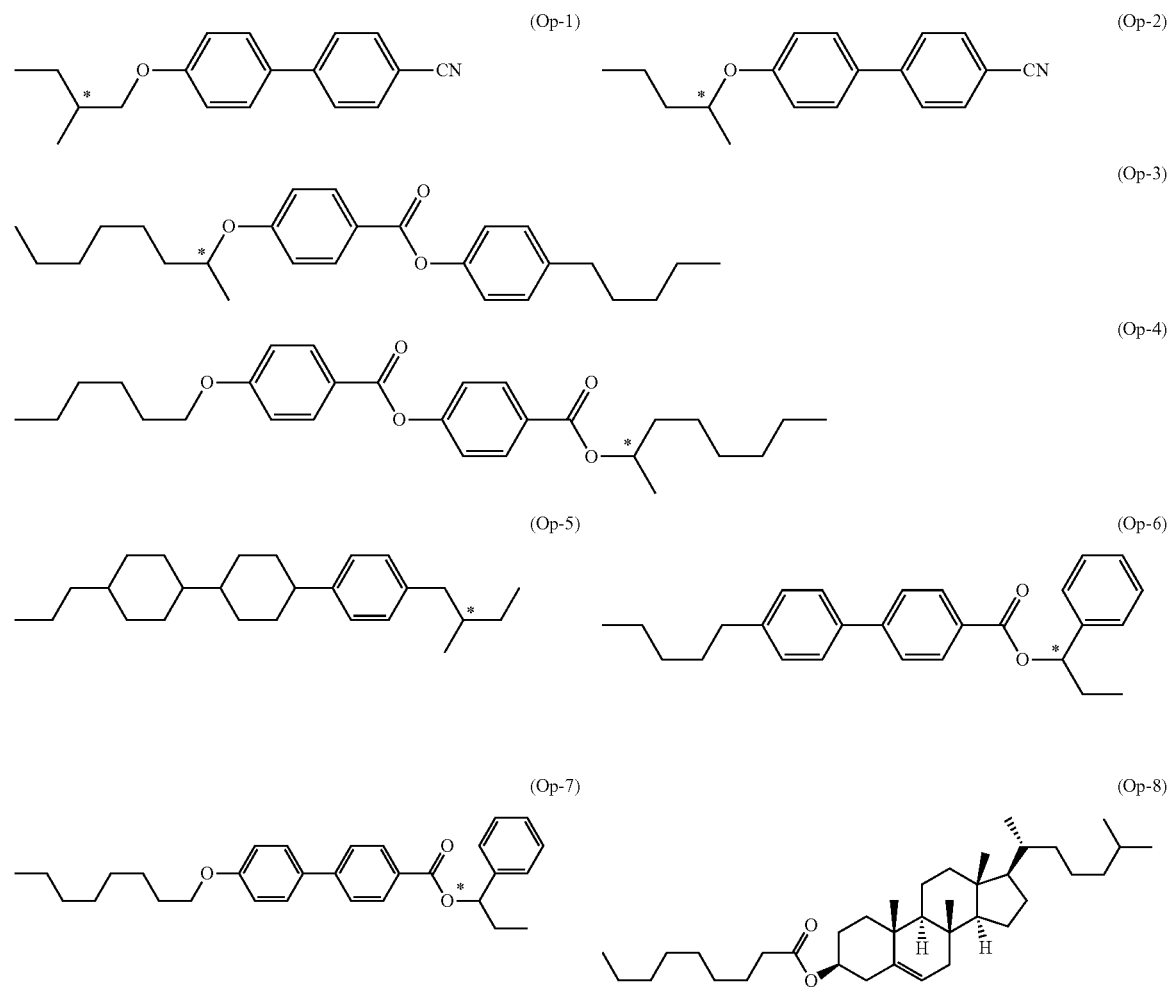

(Op-9)
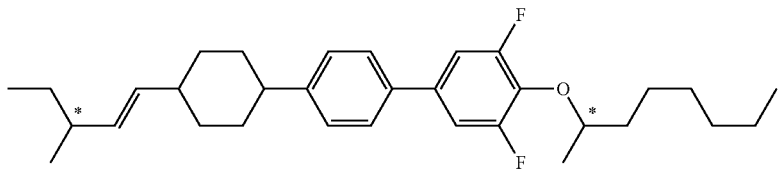
(Op-10)
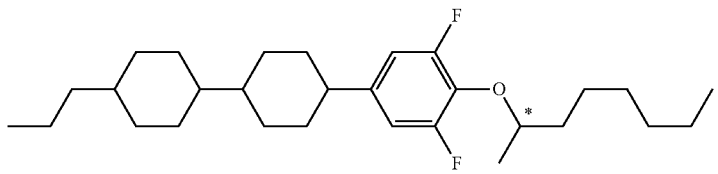
(Op-11)
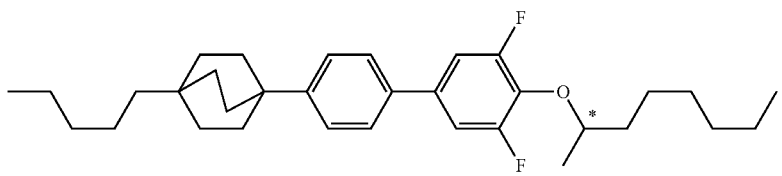
(Op-12)
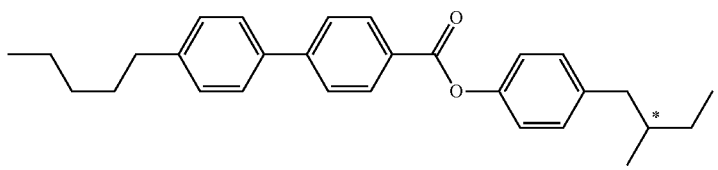
(Op-13)
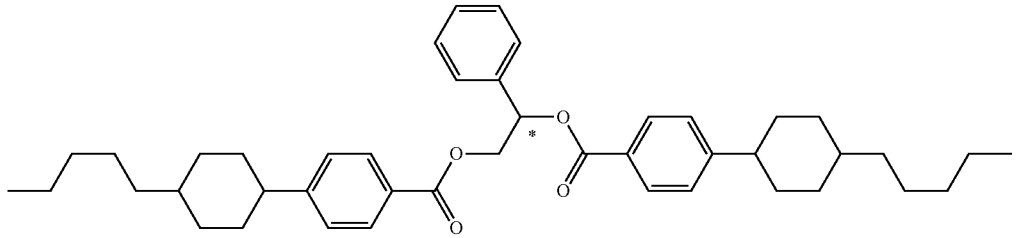
(Op-14)
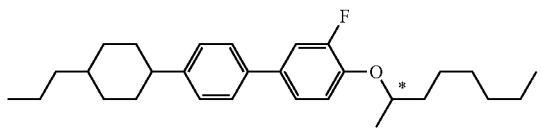
(Op-15)
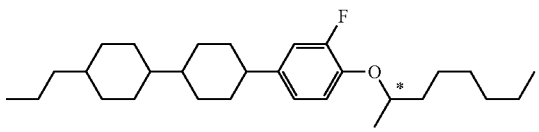
(Op-16)
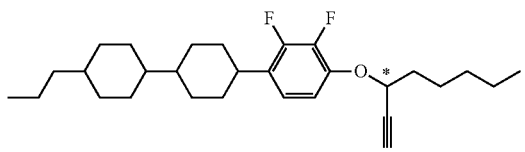
(Op-17)
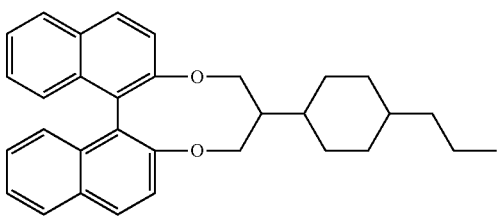

(Op-18)

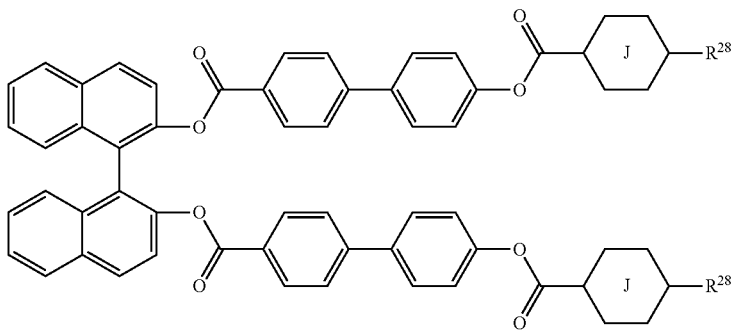

The antioxidant is effective for maintaining the large voltage holding ratio. Preferred examples of the antioxidant include compounds (AO-1) and (AO-2) described below; IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease in the maximum temperature. Preferred examples of the ultraviolet light absorber include a benzophenone derivative, a benzoate derivative and a triazole derivative. Specific examples include compounds (AO-3) to (AO-4) described below; TINUVIN 329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Preferred examples of the light stabilizers include compounds (AO-5) and (AO-6) described below; TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). The antifoaming agent is effective for preventing foam formation. Preferred examples of the antifoaming agent include dimethyl silicone oil and methylphenyl silicone oil.

(AO-1)

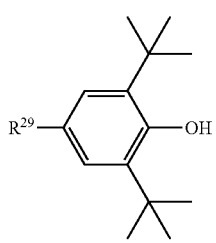

(AO-2)

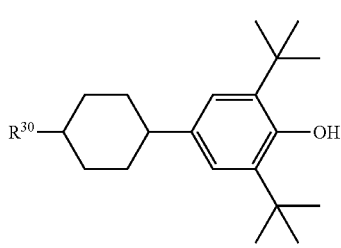

-continued (AO-3)

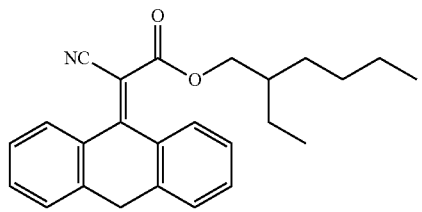

(AO-4)

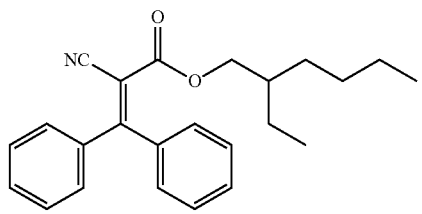

(AO-5)

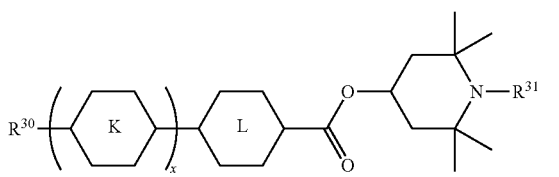

(AO-6)

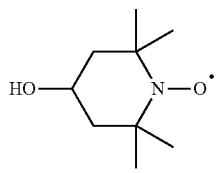

In compound (AO-1), $R^{29}$ is alkyl having 1 to 20 carbons, alkoxy having 1 to 20 carbons, —COOR$^{32}$ or —CH$_2$CH$_2$COOR$^{32}$, in which $R^{32}$ is alkyl having 1 to 20 carbons. In compounds (AO-2) and (AO-5), $R^{30}$ is alkyl having 1 to 20 carbons. In compound (AO-5), $R^{31}$ is hydrogen, methyl or O. (oxygen radical), and ring K and ring L are 1,4-cyclohexylene or 1,4-phenylene, and x is 0, 1 or 2.

4. Liquid Crystal Composite

Compound (1) has the suitable polymerization reactivity, the high conversion and the high solubility in the liquid crystal composition. The liquid crystal composite is formed by polymerizing the polymerizable composition containing compound (1) and the liquid crystal composition. Compound (1) forms a polymer in the liquid crystal composition by polymerization. The polymer is effective in stabilizing initial alignment of the liquid crystal molecules. In addition, a pretilt can also be generated when polymerization is carried out while an electric field is applied thereto. Polymerization occurs by heat, light or the like. Preferred reaction is photopolymerization. Polymerization may be carried out while the electric field or a magnetic field is applied thereto.

The polymerization reactivity and the conversion of compound (1) can be adjusted. Compound (1) is suitable for radical polymerization. Compound (1) can be rapidly polymerized by adding the polymerization initiator. An amount of remaining compound (1) can be decreased by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate, and a mixture of benzophenone and methyltriethanolamine.

After the photoradical polymerization initiator is added to the polymerizable composition, polymerization can be carried out by irradiation with ultraviolet light. However, an unreacted polymerization initiator or a decomposition product of the polymerization initiator may cause poor display such as image persistence in the device. In order to prevent such an event, photopolymerization may be carried out with no addition of the polymerization initiator. A preferred wavelength of irradiation light is in the range of 150 nanometers to 500 nanometers. A further preferred wavelength is in the range of 250 nanometers to 450 nanometers, and the most preferred wavelength is in the range of 300 nanometers to 400 nanometers.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-tert-butylcatechol, 4-methoxyphenol and phenothiazine.

5. Liquid Crystal Display Device

An effect of the polymer in the liquid crystal display device is construed as described below. The polymerizable composition is a mixture of the liquid crystal compound, the polymerizable compound and so forth. When the composition is injected into a liquid crystal cell, the composition exhibits various initial alignment states depending on respective characteristics of the cell used and the composition used. The composition is irradiated with ultraviolet light in the above state to polymerize the polymerizable compound. On the occasion, an electric field may be applied to the cell. As a result, a network of the polymer is formed in the polymerizable composition. The liquid crystal molecules are stabilized in a state before irradiation with ultraviolet light by an effect of the network. In addition, although the initial alignment is random alignment, ordered alignment such as homogeneous alignment and homeotropic alignment can also be formed by irradiation with ultraviolet light. Thus, the liquid crystal display device stabilized in various alignment states can be obtained by polymerizing the polymerizable composition by irradiation with ultraviolet light.

The polymerizable composition is preferably polymerized in the display device. One example is as described below. A display device having two glass substrates provided with a transparent electrode on at least one of the substrates is arranged. A polymerizable composition containing compound (1), a liquid crystal composition, an additive and so forth as a component is prepared. The composition is injected into the device. Compound (1) is polymerized by irradiating the display device with ultraviolet light. A liquid crystal composite is formed by the polymerization. A liquid crystal display device having the liquid crystal composite can be easily prepared according to the above method. In the method, rubbing treatment of an alignment film may be omitted, and no alignment film may be provided.

When an amount of addition of the polymerizable compound is in the range of 0.1% by weight to 2% by weight based on the weight of the liquid crystal composition, the liquid crystal display device having the PSA mode is prepared. The device having the PSA mode can be driven by a drive system such as an active matrix (AM) and a passive matrix (PM). Such a device can be applied to any type of a reflective type, a transmissive type and a transflective type. A device having a polymer dispersed mode can also be prepared by increasing the amount of addition of the polymerizable compound.

EXAMPLES

The invention will be described in greater detail by way of Examples. The invention is not limited by the Examples. The invention includes a mixture of a composition in Example 1 and a composition in Example 2. The invention also contains a composition prepared by mixing at least two of compositions in Examples. The thus prepared compound was identified by methods such as an NMR analysis. Physical properties of the compound, the composition and a device were measured by methods described below.

1. Example of Compound (1)

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra, s, d, t, q, quin, sex, m and br stand for a singlet, a doublet, a triplet, a quartet, a quintet, a sextet, a multiplet and a broad, respectively.

HPLC analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile and prepared to be a 0.1 weight % solution, and then 1 microliter of the solution was injected into a sample chamber. As a recorder, C-R7Aplus made by Shimadzu Corporation was used.

Ultraviolet-visible spectrophotometry: For measurement, PharmaSpec UV-1700 made by Shimadzu Corporation was used. A detection wavelength was adjusted in the range of 190 nanometers to 700 nanometers. A sample was dissolved in acetonitrile, and prepared to be a solution of 0.01 millimole per liter, and measurement was carried out by putting the solution in a quartz cell (optical path length: 1 cm).

Sample for measurement: Upon measuring a phase structure and a transition temperature (a clearing point, a melting point, a polymerization starting temperature or the like), a compound itself was used as a sample. Upon measuring physical properties such as a maximum temperature, viscosity, optical anisotropy and dielectric anisotropy of a liquid crystal compound, a mixture of the compound and a base liquid crystal was used as a sample. When physical properties of a liquid crystal composition were measured, the composition itself was used as a sample.

As a base liquid crystal, base liquid crystal (A) or base liquid crystal (B) described below or the like was used. A proportion of each component of base liquid crystals (A) and (B) was expressed in terms of % by weight.

Base liquid crystal (A):

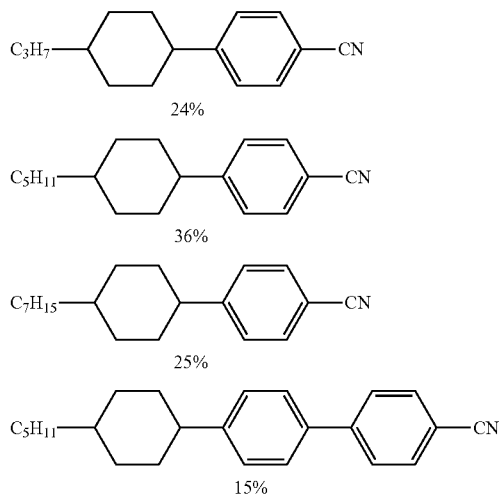

Base liquid crystal (B):

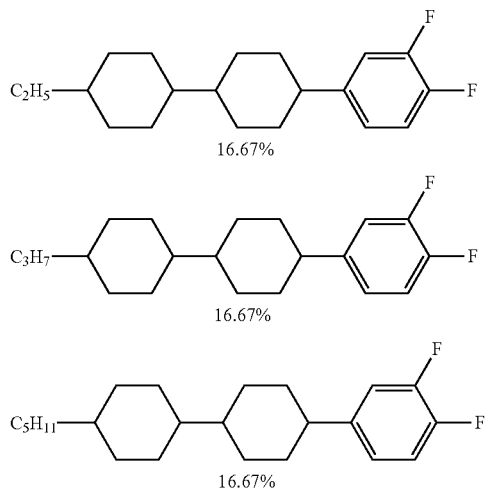

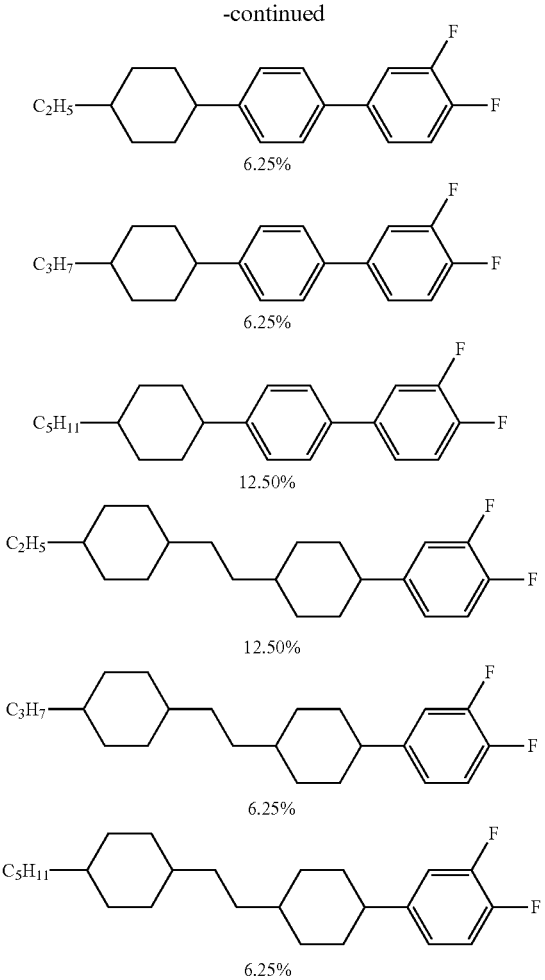

Measuring method: Measurement of physical properties was carried out by the methods described below. Most of the methods are described in the Standard of Japan Electronics and Information Technology Industries Association (hereinafter, abbreviated as JEITA) discussed and established in JEITA (JEITA ED-2521B). A modification of the methods was also used. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition Temperature (° C.)

For measurement, a scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as a smectic phase and a nematic phase may be occasionally abbreviated as "minimum temperature of the liquid crystal phase." Temperature at which the compound undergoes transition from the liquid crystal phase to liquid may be occasionally abbreviated as "clearing point."

The crystals were expressed as C. When kinds of the crystals were distinguishable, each of the crystals was expressed as $C_1$ or $C_2$. The smectic phase and the nematic phase were expressed as S and N, respectively. When a smectic A phase, a smectic B phase, a smectic C phase or a smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of a Nematic Phase ($T_{NI}$ or NI; ° C.)

A sample was placed on a hot plate of a melting point apparatus equipped with a polarizing microscope, and was heated at a rate of 1° C. per minute. Temperature when part of the sample began to change from the nematic phase to an isotropic liquid was measured. A maximum temperature of the nematic phase may be occasionally abbreviated as "maximum temperature." When the sample was a mixture of the liquid crystal compound and the base liquid crystal, the maximum temperature was expressed as a symbol $T_{NI}$. When the sample was a mixture of the liquid crystal compound and a compound such as component B, compound C and compound D, the maximum temperature was expressed using a symbol NI.

(4) Minimum Temperature of a Nematic Phase ($T_C$; ° C.)

Samples each having a nematic phase were put in glass vials and kept in freezers at temperatures of 0° C., −10° C., −20° C., −30° C. and −40° C. for 10 days, and then liquid crystal phases were observed. For example, when the sample was maintained in the nematic phase at −20° C. and changed to crystals or a smectic phase at −30° C., $T_C$ of the sample was expressed as $T_C \leq -20°$ C. A minimum temperature of the nematic phase may be occasionally abbreviated as "minimum temperature."

(5) Viscosity (Bulk Viscosity; η; Measured at 20° C.; mPa·s)

Viscosity was measured by using an E type rotational viscometer made by TOKYO KEIKI INC.

(6) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of the optical anisotropy (Δn) was calculated from an equation: Δn=n∥−n⊥.

(7) Specific Resistance (ρ; Measured at 25° C.; Ωcm)

Into a vessel equipped with electrodes, 1.0 milliliter of a sample was injected. A direct current voltage (10 V) was applied to the vessel, and a direct current after 10 seconds was measured. Specific resistance was calculated from the following equation: (specific resistance)={(voltage)×(electric capacity of a vessel)}/((direct current)×(dielectric constant of vacuum)).

(8) Voltage Holding Ratio (VHR-1; Measured at 25° C.; %)

A TN device used for measurement had a polyimide alignment film, and a distance (cell gap) between two glass substrates was 5 micrometers. A sample was put in the device, and the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(9) Voltage Holding Ratio (VHR-2; Measured at 80° C.; %)

A voltage holding ratio was measured according to the method described above except that a sample was measured at 80° C. in place of 25° C. The thus obtained value was expressed by a symbol of VHR-2.

(10) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. A voltage was applied stepwise to the device in the range of 16 V to 19.5 V at an increment of 0.5 V. After a period of 0.2 second with no voltage application, a voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values according to calculating equation (8) on page 40 of the paper presented by M. Imai et al. A value of dielectric anisotropy required for the calculation was determined using the device by which the rotational viscosity was measured and by a method described below.

(11) Dielectric Anisotropy (Δε; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ε∥) in a major axis direction of the liquid crystal molecules was measured. Sine waves (0.5 V, 1 kHz) were applied to the device, and after 2 seconds, a dielectric constant (ε⊥) in a minor axis direction of the liquid crystal molecules was measured. A value of dielectric anisotropy was calculated from an equation: Δε=ε∥−ε⊥.

(12) Elastic Constant (K; Measured at 25° C.; pN)

For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity and an applied voltage were measured. The measured values of the electrostatic capacity (C) and the applied voltage (V) were fitted to equation (2.98) and equation (2.101) on page 75 of "Liquid Crystal Device Handbook" (Ekisho Debaisu Handobukku, in Japanese; Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K is expressed using a mean value of the thus determined $K_{11}$, $K_{22}$ and $K_{33}$.

(13) Threshold Voltage (Vth; Measured at 25° C.; V)

For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of a voltage at 90% transmittance.

(14) Response Time (τ; Measured at 25° C.; ms)

For measurement, an LCD-5100 luminance meter made by Otsuka Electronics Co., Ltd. was used. A light source was a halogen lamp. A low-pass filter was set to 5 kHz. A sample was put in a normally white mode TN device in which a distance (cell gap) between two glass substrates was 5.0 micrometers and a twist angle was 80 degrees. Rectangular waves (60 Hz, 5 V, 0.5 second) were applied to the device. On the occasion, the device was irradiated with light from a direction perpendicular to the device, and an amount of light transmitted through the device was measured. The maximum amount of light corresponds to 100% transmittance and the minimum amount of light corresponds to 0% transmittance. A rise time (τr; ms) was expressed in terms of a time required for a change from 90% transmittance to 10% transmittance. A fall time (τf; ms) was expressed in terms of a time required for a change from 10% transmittance to 90% transmittance. A response time was represented by a sum of the rise time and the fall time thus obtained.

(15) Compatibility at Room Temperature

Samples in which the base liquid crystal and the compound were mixed to be 20% by weight, 15% by weight, 10% by weight, 5% by weight, 3% by weight and 1% by weight in a proportion of compounds were prepared. After the samples were left to stand for one day, whether or not crystals or a smectic phase precipitated was observed.

Synthetic Example 1

Synthesis of compound (No. 9)

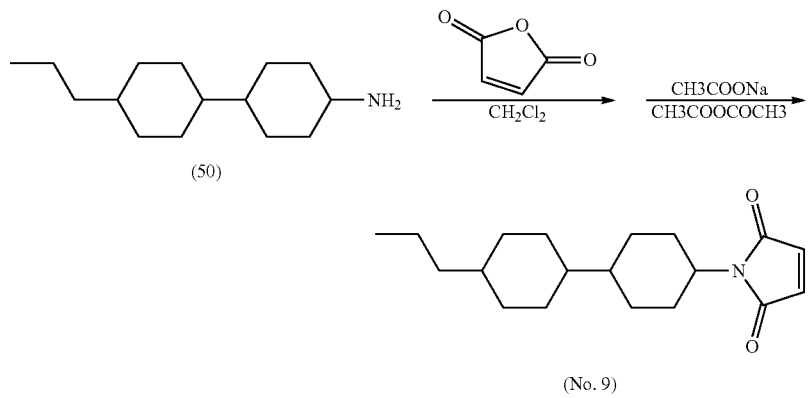

Compound (50), (6.19 g, 27.7 mmol), maleic anhydride (2.71 g, 27.7 mmol) and dichloromethane (30 mL) were put in a vessel, and the resulting mixture was refluxed for 1 hour. The mixture was concentrated, and acetic anhydride (30 mL) and sodium acetate (1.59 g, 19.4 mL) were added thereto, and the resulting mixture was refluxed for 3 hours. The reaction mixture was cooled to room temperature, and slowly poured into water, and the resulting mixture was subjected to extraction with ethyl acetate. Combined organic layers were washed with water and saturated brine, and dried over anhydrous magnesium sulfate, and concentrated under reduced pressure. The resulting residue was purified with silica gel chromatography (toluene) to obtain compound (No. 9) (4.0 g).

$^1$H-NMR (CDCl$_3$; δ ppm): 6.61 (s, 2H), 3.88 (quint, 1H), 2.08 (q, 2H), 1.90-1.60 (m, 8H), 1.39 (sex, 2H), 1.20-0.80 (m, 11H) and 0.87 (t, 3H).

Physical properties of compound (No. 9) were as described below.

Transition temperature: C 132.2 C 171 I; $T_{NI}$=91.7° C.; η=100.1 mPa·s; Δn=0.104; Δε=8.57; compatibility at room temperature: 3% by weight.

Compounds (No. 1) to (No. 84) described below can be prepared in a manner similar to the method described in Synthetic Example 1.

| | No. |
|---|---|
| 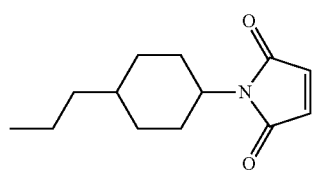 [SMILES: CCCC1CCC(N2C(=O)C=CC2=O)CC1] | 1 |
| 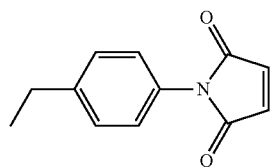 | 2 |
| 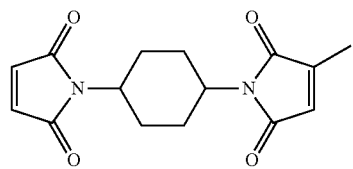 [SMILES: CC1=CC(=O)N(C2CCC(N3C(=O)C=CC3=O)CC2)C1=O] | 3 |
| 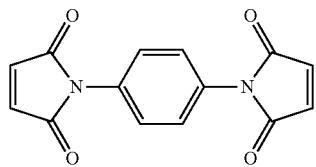 [SMILES: O=C1C=CC(=O)N1c1ccc(N2C(=O)C=CC2=O)cc1] | 4 |
| 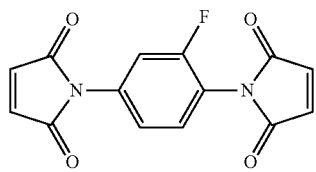 [SMILES: O=C1C=CC(=O)N1c1ccc(N2C(=O)C=CC2=O)c(F)c1] | 5 |
| 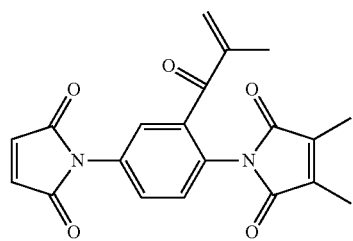 [SMILES: C=C(C)C(=O)c1cc(N2C(=O)C=CC2=O)ccc1N1C(=O)C(C)=C(C)C1=O] | 6 |
| 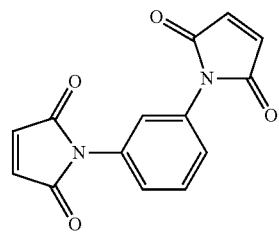 [SMILES: O=C1C=CC(=O)N1c1cccc(N2C(=O)C=CC2=O)c1] | 7 |

-continued
| | No. |
|---|---|
| 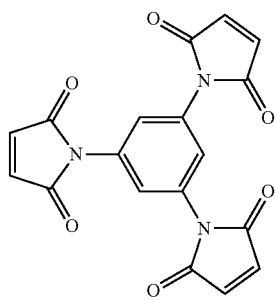 [SMILES: O=C1C=CC(=O)N1c1cc(N2C(=O)C=CC2=O)cc(N2C(=O)C=CC2=O)c1] | 8 |
| 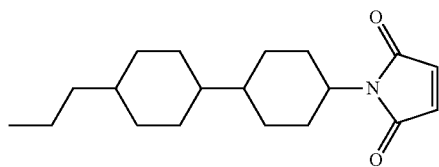 [SMILES: CCCC(C)CCC(CC)C1CCC(N2C(=O)C=CC2=O)CC1] | 9 |
| 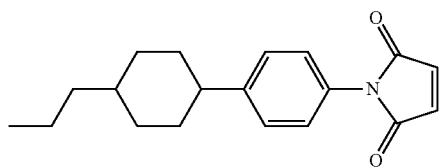 [SMILES: CCCC(C)CCC(CC)c1ccc(N2C(=O)C=CC2=O)cc1] | 10 |
| 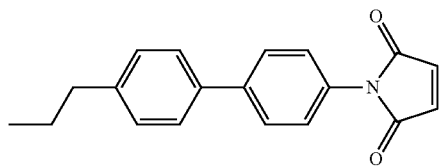 [SMILES: CCCc1ccc(-c2ccc(N3C(=O)C=CC3=O)cc2)cc1] | 11 |
| 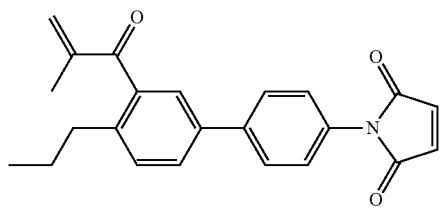 [SMILES: C=C/C(=C\C(C(=O)C(=C)C)=C(/C)CCC)c1ccc(N2C(=O)C=CC2=O)cc1] | 12 |
| 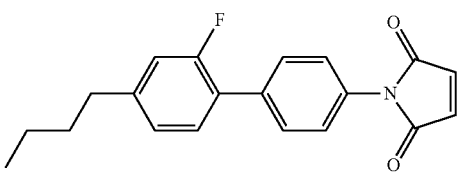 [SMILES: CCCCc1ccc(-c2ccc(N3C(=O)C=CC3=O)cc2)c(F)c1] | 13 |
| 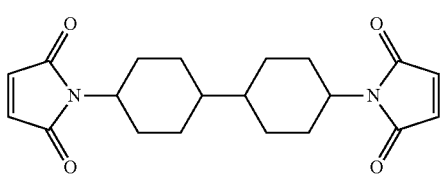 [SMILES: CC1CC(N2C(=O)C=CC2=O)CCC1C1CCC(N2C(=O)C=CC2=O)CC1] | 14 |
| 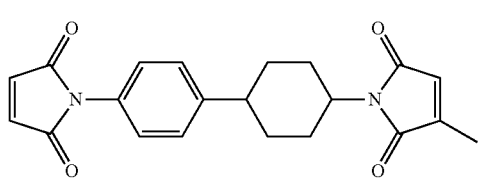 [SMILES: CC1=CC(=O)N(C2CCC(c3ccc(N4C(=O)C=CC4=O)cc3C)CC2)C1=O] | 15 |

| | No. |
|---|---|
| 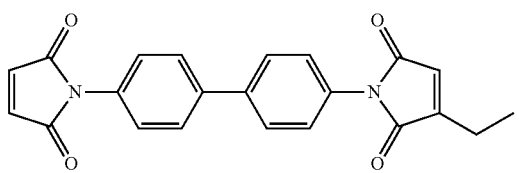 [SMILES: CCC1=CC(=O)N(c2ccc(-c3ccc(N4C(=O)C=CC4=O)cc3C)cc2)C1=O] | 16 |
| 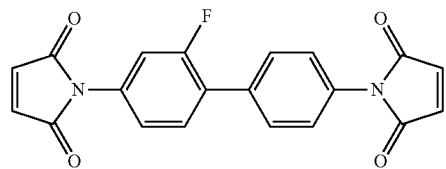 [SMILES: Cc1cc(N2C(=O)C=CC2=O)cc(F)c1-c1ccc(N2C(=O)C=CC2=O)cc1] | 17 |
| 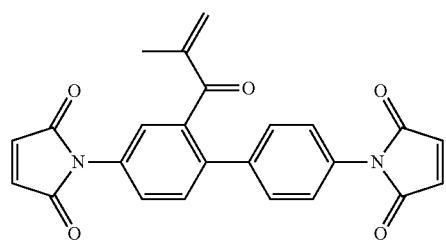 [SMILES: C=C(C)C(=O)c1cc(N2C(=O)C=CC2=O)cc(C)c1-c1ccc(N2C(=O)C=CC2=O)cc1] | 18 |
| 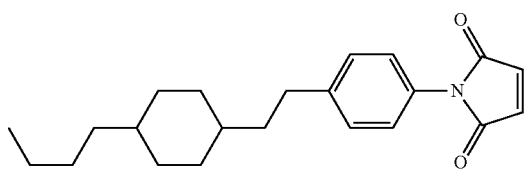 [SMILES: CCCCC1CCC(CCc2ccc(N3C(=O)C=CC3=O)cc2)CC1] | 19 |
| 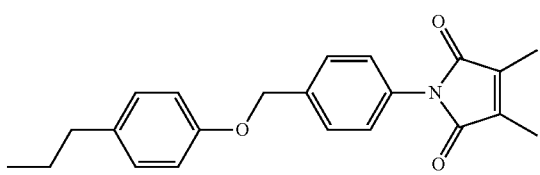 [SMILES: CCCc1ccc(OCc2ccc(N3C(=O)C(C)=C(C)C3=O)cc2)cc1] | 20 |
| 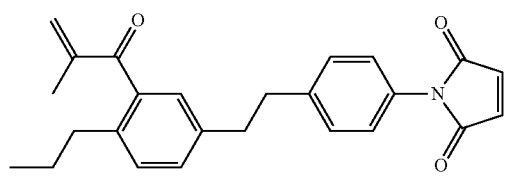 [SMILES: C=C(C)C(=O)c1cc(CCc2ccc(N3C(=O)C=CC3=O)cc2)ccc1CCC] | 21 |
| 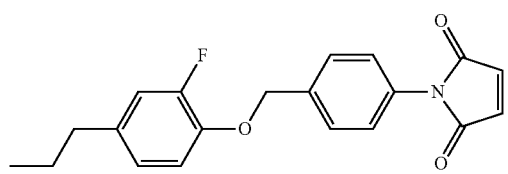 [SMILES: CCCc1ccc(OCc2ccc(N3C(=O)C=CC3=O)cc2)c(F)c1] | 22 |
| 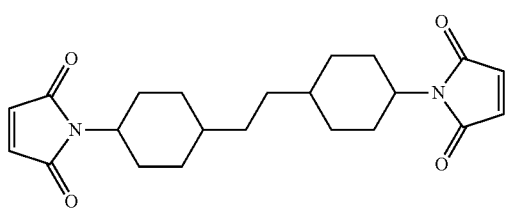 [SMILES: O=C1C=CC(=O)N1C1CCC(CCC2CCC(N3C(=O)C=CC3=O)CC2)CC1] | 23 |

-continued
| No. |
|---|
| 24 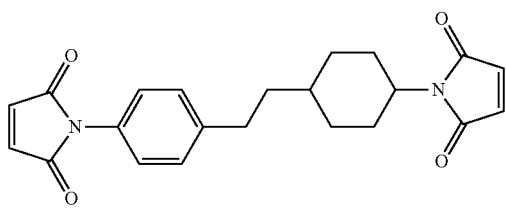 [SMILES: O=C1C=CC(=O)N1c1ccc(CCC2CCC(N3C(=O)C=CC3=O)CC2)cc1] |
| 25 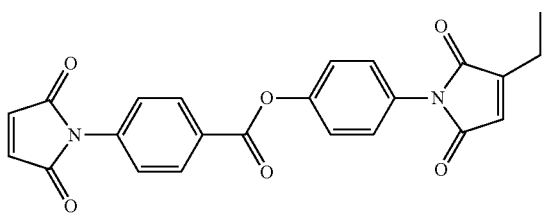 [SMILES: CCC1=CC(=O)N(c2ccc(OC(=O)c3ccc(N4C(=O)C=CC4=O)cc3)cc2)C1=O] |
| 26 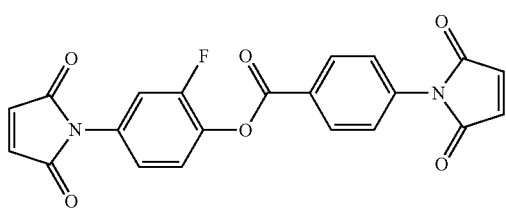 [SMILES: O=C(Oc1ccc(N2C(=O)C=CC2=O)cc1F)c1ccc(N2C(=O)C=CC2=O)cc1] |
| 27 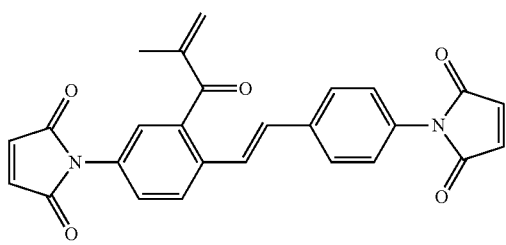 [SMILES: C=C(C)C(=O)c1cc(N2C(=O)C=CC2=O)ccc1/C=C/c1ccc(N2C(=O)C=CC2=O)cc1] |
| 28 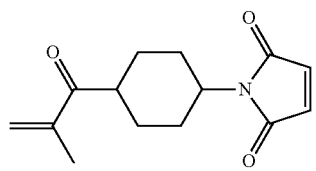 [SMILES: C=C(C)C(=O)C1CCC(N2C(=O)C=CC2=O)CC1] |
| 29 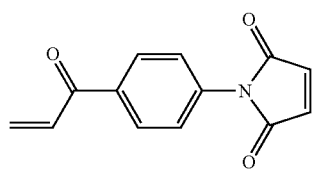 [SMILES: C=CC(=O)c1ccc(N2C(=O)C=CC2=O)cc1] |
| 30 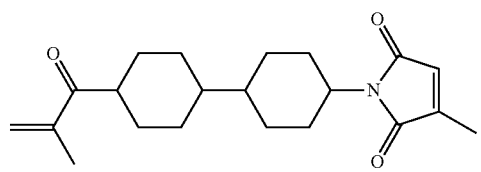 [SMILES: C=C(C)C(=O)C1CCC(C2CCC(N3C(=O)C=C(C)C3=O)CC2)CC1] |
| 31 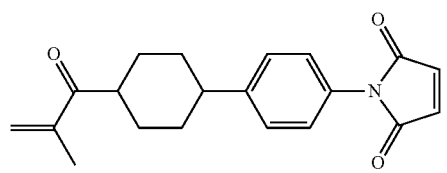 [SMILES: C=C(C)C(=O)C1CCC(c2ccc(N3C(=O)C=CC3=O)cc2)CC1] |

-continued
| No. |
|---|
| 32 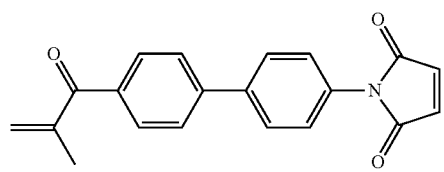 [SMILES: C=C(C)C(=O)c1ccc(-c2ccc(N3C(=O)C=CC3=O)cc2)cc1] |
| 33 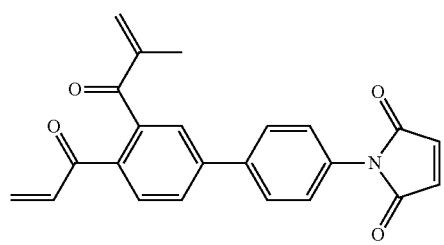 [SMILES: C=CC(=O)c1ccc(-c2ccc(N3C(=O)C=CC3=O)cc2)cc1C(=O)C(=C)C] |
| 34 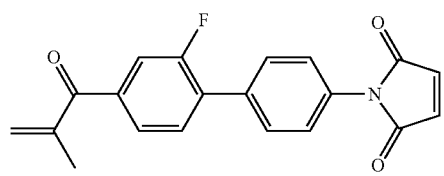 [SMILES: C=C(C)C(=O)c1ccc(-c2ccc(N3C(=O)C=CC3=O)cc2)c(F)c1] |
| 35 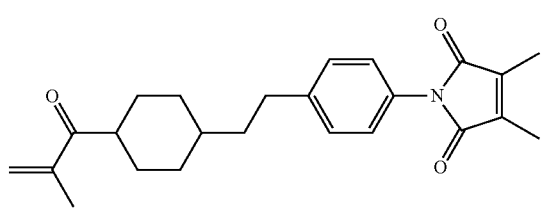 [SMILES: C=C(C)C(=O)C1CCC(CCc2ccc(N3C(=O)C(C)=C(C)C3=O)cc2)CC1] |
| 36 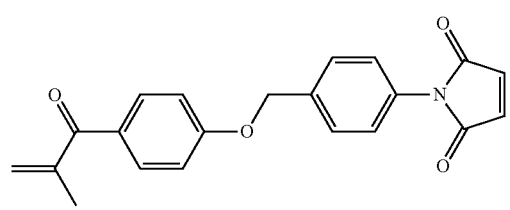 [SMILES: C=C(C)C(=O)c1ccc(OCc2ccc(N3C(=O)C=CC3=O)cc2)cc1] |
| 37 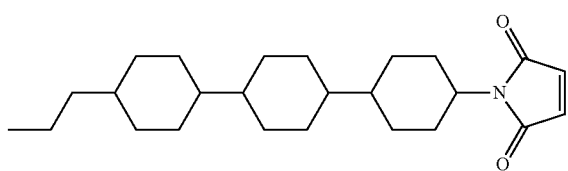 [SMILES: CCCC1CCC(C2CCC(C3CCC(N4C(=O)C=CC4=O)CC3)CC2)CC1] |
| 38 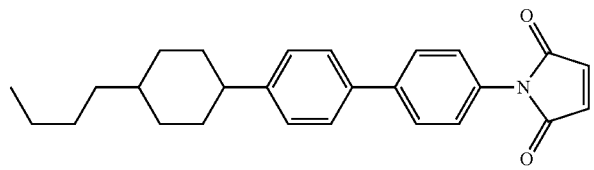 [SMILES: CCCCC1CCC(c2ccc(-c3ccc(N4C(=O)C=CC4=O)cc3)cc2)CC1] |
| 39 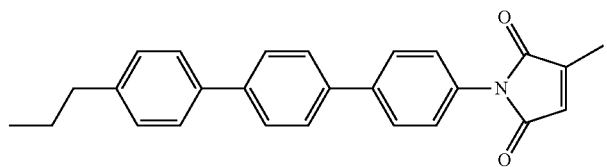 [SMILES: CCCc1ccc(-c2ccc(-c3ccc(N4C(=O)C=C(C)C4=O)cc3)cc2)cc1] |

|  | No. |
|---|---|
| 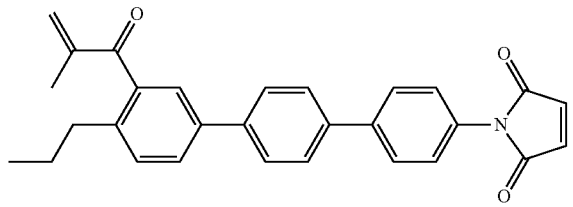 [SMILES: C=C(C)C(=O)c1cc(-c2ccc(-c3ccc(N4C(=O)C=CC4=O)cc3)cc2)ccc1CCC] | 40 |
| 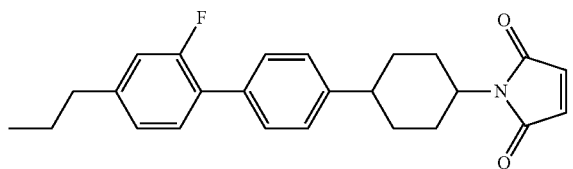 [SMILES: CCCc1ccc(-c2ccc(C3CCC(N4C(=O)C=CC4=O)CC3)cc2)c(F)c1] | 41 |
| 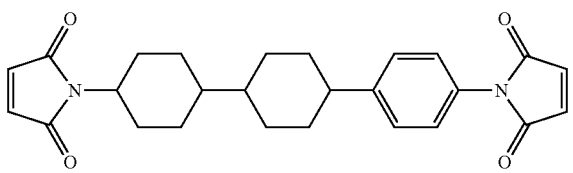 [SMILES: O=C1C=CC(=O)N1c1ccc(C2CCC(C3CCC(N4C(=O)C=CC4=O)CC3)CC2)cc1] | 42 |
| 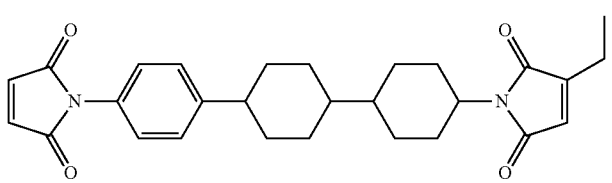 [SMILES: CCC1=CC(=O)N(C2CCC(C3CCC(c4ccc(N5C(=O)C=CC5=O)cc4)CC3)CC2)C1=O] | 43 |
| 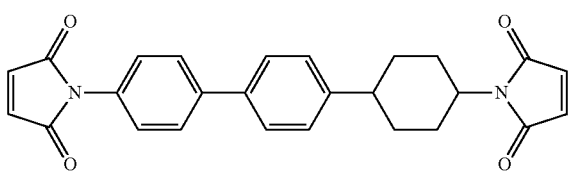 [SMILES: O=C1C=CC(=O)N1c1ccc(-c2ccc(C3CCC(N4C(=O)C=CC4=O)CC3)cc2)cc1] | 44 |
| 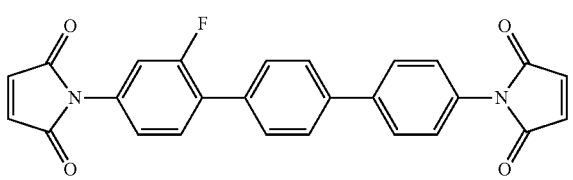 [SMILES: O=C1C=CC(=O)N1c1ccc(-c2ccc(-c3ccc(N4C(=O)C=CC4=O)cc3F)cc2)cc1] | 45 |
| 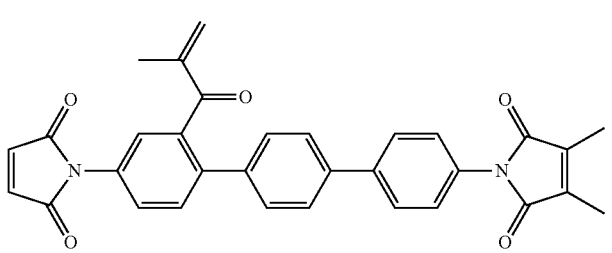 [SMILES: C=C(C)C(=O)c1cc(N2C(=O)C=CC2=O)ccc1-c1ccc(-c2ccc(N3C(=O)C(C)=C(C)C3=O)cc2)cc1] | 46 |
| 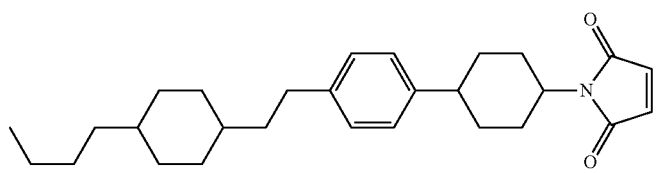 [SMILES: CCCCC1CCC(CCc2ccc(C3CCC(N4C(=O)C=CC4=O)CC3)cc2)CC1] | 47 |

| No. |
|---|
| 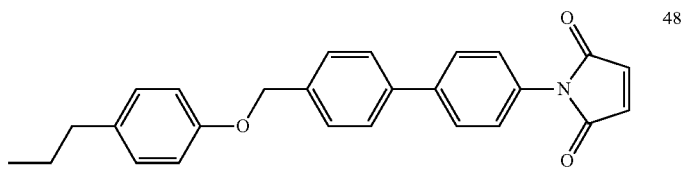 48 |
| 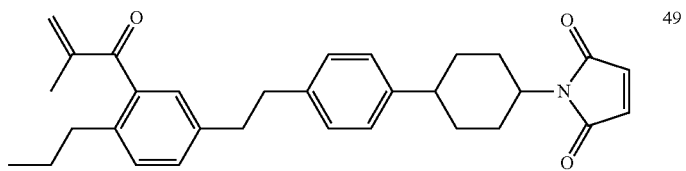 49 |
| 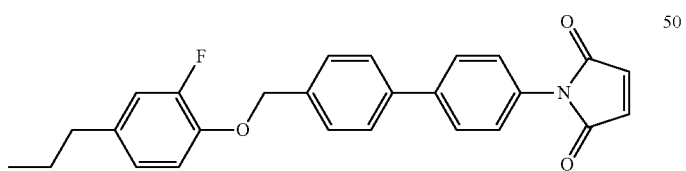 50 |
| 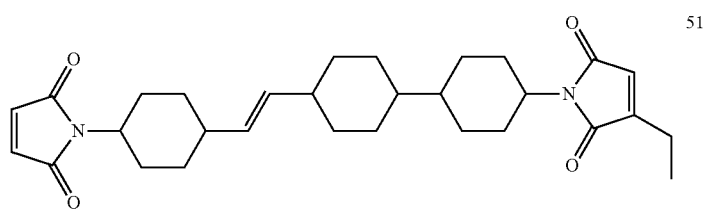 51 |
| 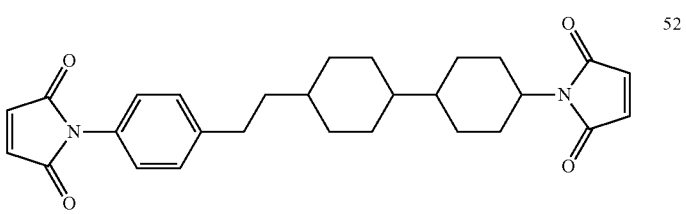 52 |
| 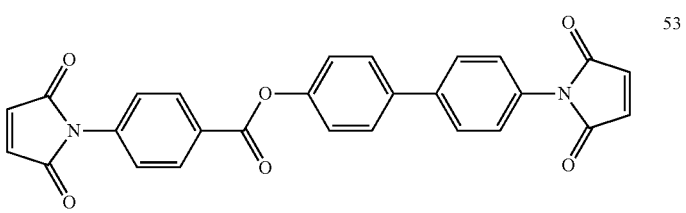 53 |
| 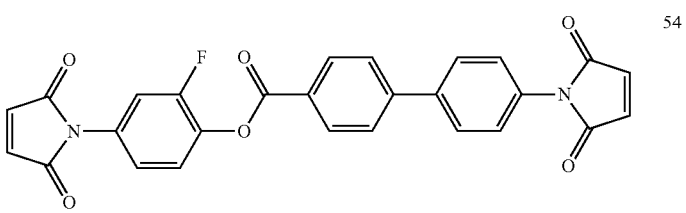 54 |

| No. |
|---|
| 55 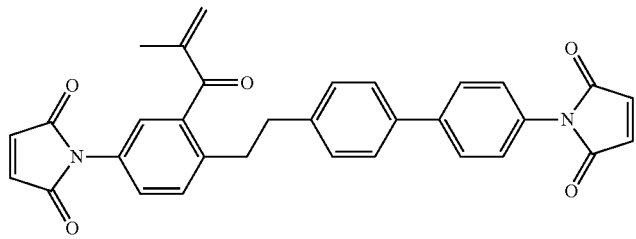 [SMILES: C=C(C)C(=O)c1cc(N2C(=O)C=CC2=O)ccc1CCc1ccc(-c2ccc(N3C(=O)C=CC3=O)cc2)cc1] |
| 56 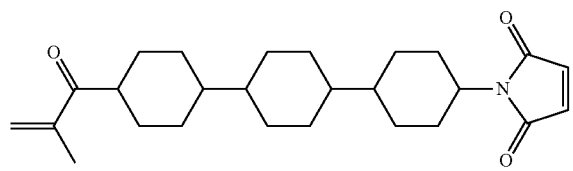 [SMILES: C=C(C)C(=O)C1CCC(C2CCC(C3CCC(N4C(=O)C=CC4=O)CC3)CC2)CC1] |
| 57 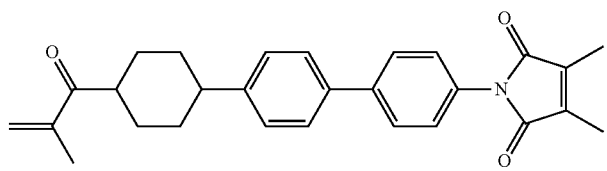 [SMILES: C=C(C)C(=O)C1CCC(c2ccc(-c3ccc(N4C(=O)C(C)=C(C)C4=O)cc3)cc2)CC1] |
| 58 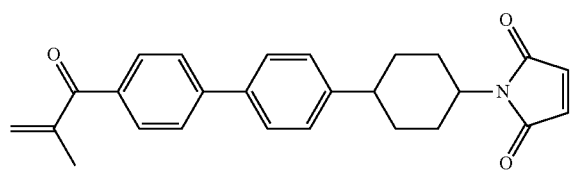 [SMILES: C=C(C)C(=O)c1ccc(-c2ccc(C3CCC(N4C(=O)C=CC4=O)CC3)cc2)cc1] |
| 59 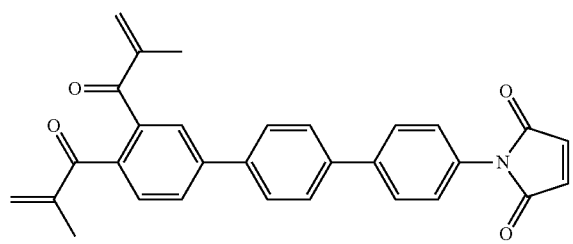 [SMILES: C=C(C)C(=O)c1ccc(-c2ccc(-c3ccc(N4C(=O)C=CC4=O)cc3)cc2)cc1C(=O)C(=C)C] |
| 60 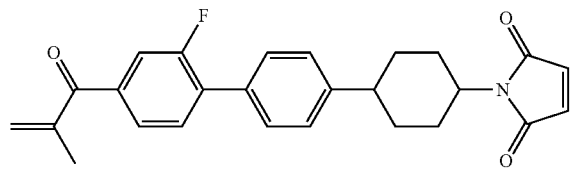 [SMILES: C=C(C)C(=O)c1ccc(-c2ccc(C3CCC(N4C(=O)C=CC4=O)CC3)cc2)c(F)c1] |
| 61 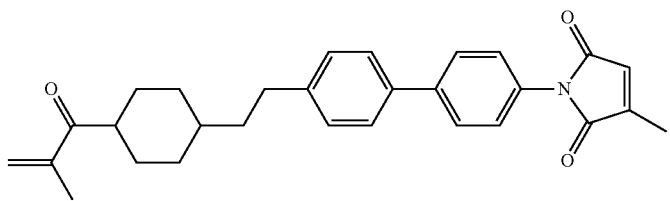 [SMILES: C=C(C)C(=O)C1CCC(CCc2ccc(-c3ccc(N4C(=O)C=C(C)C4=O)cc3)cc2)CC1] |

-continued
| No. |
|---|
| 62 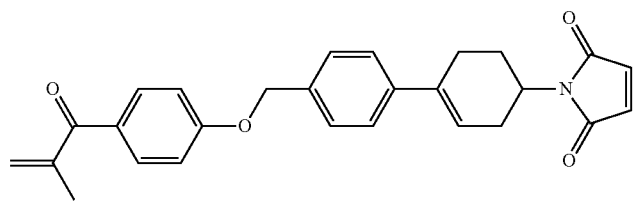 [SMILES: C=C(C)C(=O)c1ccc(OCc2ccc(C3=CCC(N4C(=O)C=CC4=O)CC3)cc2)cc1] |
| 63 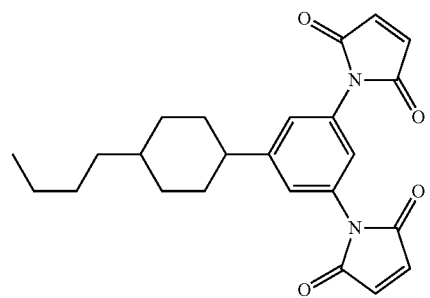 [SMILES: CCCCC1CCC(c2cc(N3C(=O)C=CC3=O)cc(N3C(=O)C=CC3=O)c2)CC1] |
| 64 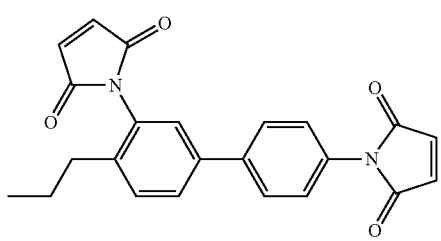 [SMILES: CCCc1ccc(-c2ccc(N3C(=O)C=CC3=O)cc2)cc1N1C(=O)C=CC1=O] |
| 65 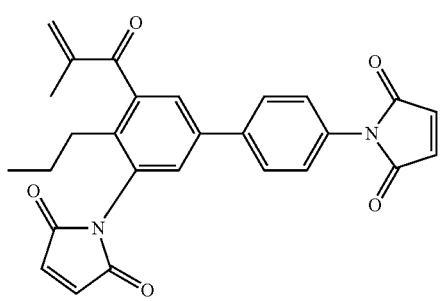 [SMILES: C=C(C)C(=O)c1cc(-c2ccc(N3C(=O)C=CC3=O)cc2)cc(N2C(=O)C=CC2=O)c1CCC] |
| 66 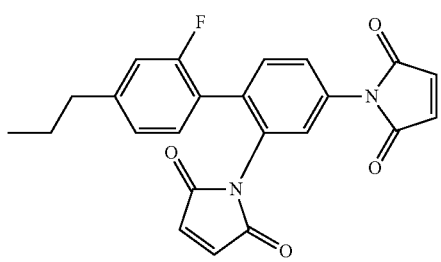 [SMILES: CCCc1ccc(-c2ccc(N3C(=O)C=CC3=O)cc2N2C(=O)C=CC2=O)c(F)c1] |
| 67 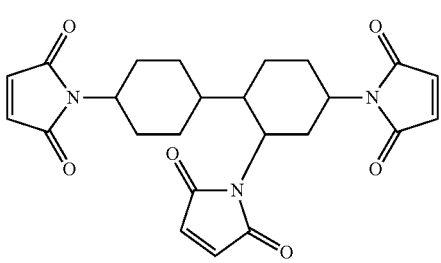 [SMILES: O=C1C=CC(=O)N1C1CCC(C2CCC(N3C(=O)C=CC3=O)CC2N2C(=O)C=CC2=O)CC1] |

| No. |
|---|
| 68 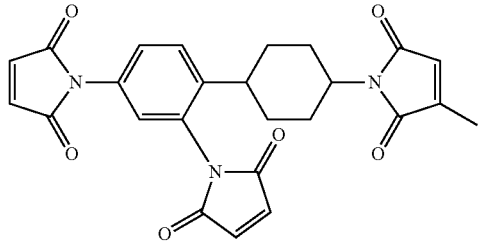 [SMILES: CC1=CC(=O)N(C2CCC(c3ccc(N4C(=O)C=CC4=O)cc3N3C(=O)C=CC3=O)CC2)C1=O] |
| 69 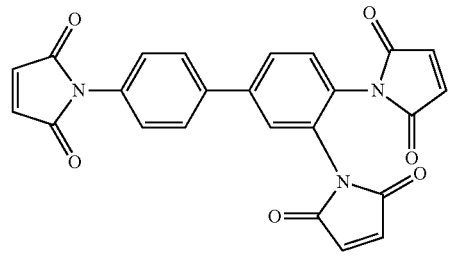 [SMILES: O=C1C=CC(=O)N1c1ccc(-c2ccc(N3C(=O)C=CC3=O)c(N3C(=O)C=CC3=O)c2)cc1] |
| 70 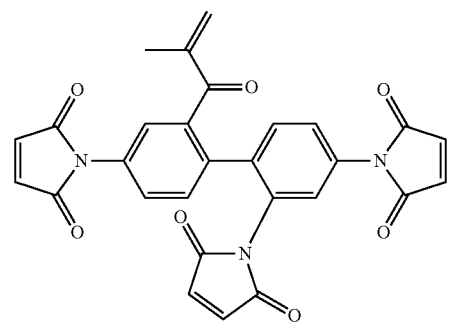 [SMILES: C=C(C)C(=O)c1cc(N2C(=O)C=CC2=O)ccc1-c1ccc(N2C(=O)C=CC2=O)cc1N1C(=O)C=CC1=O] |
| 71 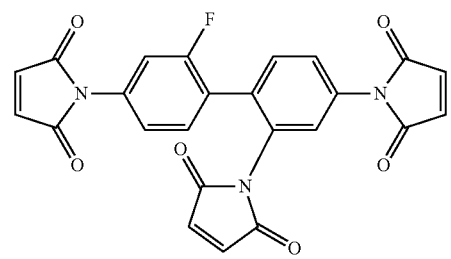 [SMILES: O=C1C=CC(=O)N1c1ccc(-c2ccc(N3C(=O)C=CC3=O)cc2N2C(=O)C=CC2=O)c(F)c1] |
| 72 |
| 73 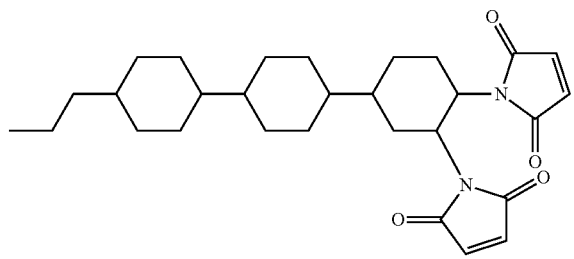 [SMILES: CCCC1CCC(C2CCC(C3CCC(N4C(=O)C=CC4=O)C(N4C(=O)C=CC4=O)C3)CC2)CC1] |

-continued
| No. |
|---|
| 74 |
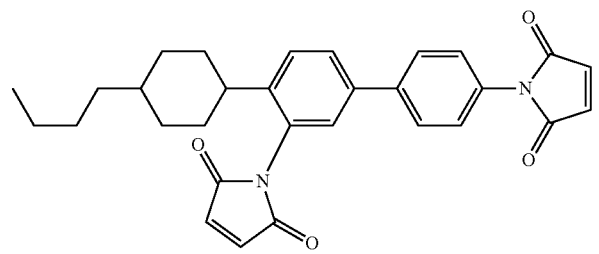 [SMILES: CCCCC1CCC(c2ccc(-c3ccc(N4C(=O)C=CC4=O)cc3)cc2N2C(=O)C=CC2=O)CC1]
| 75 |
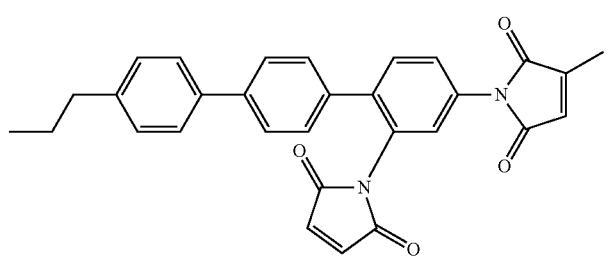 [SMILES: CCCc1ccc(-c2ccc(-c3ccc(N4C(=O)C=C(C)C4=O)cc3N3C(=O)C=CC3=O)cc2)cc1]
| 76 |
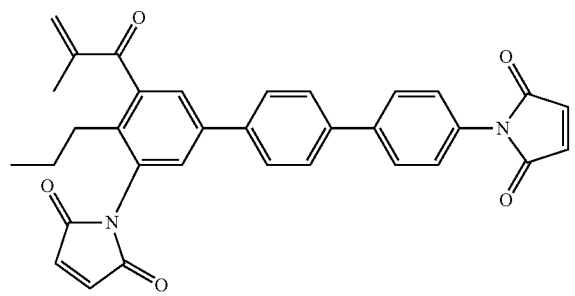 [SMILES: C=C(C)C(=O)c1cc(-c2ccc(-c3ccc(N4C(=O)C=CC4=O)cc3)cc2)cc(N2C(=O)C=CC2=O)c1CCC]
| 77 |
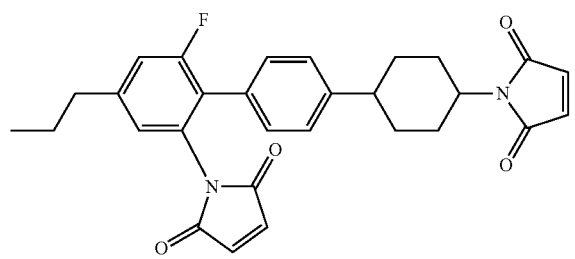 [SMILES: CCCc1cc(F)c(-c2ccc(C3CCC(N4C(=O)C=CC4=O)CC3)cc2)c(N2C(=O)C=CC2=O)c1]
| 78 |
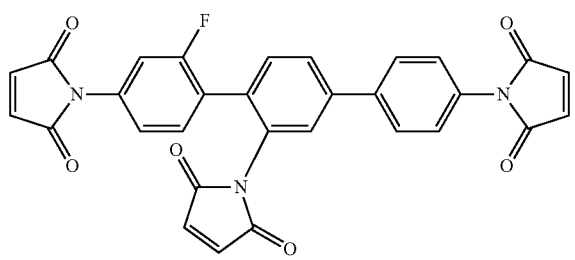 [SMILES: O=C1C=CC(=O)N1c1ccc(-c2ccc(-c3ccc(N4C(=O)C=CC4=O)cc3F)c(N3C(=O)C=CC3=O)c2)cc1]
| 79 |
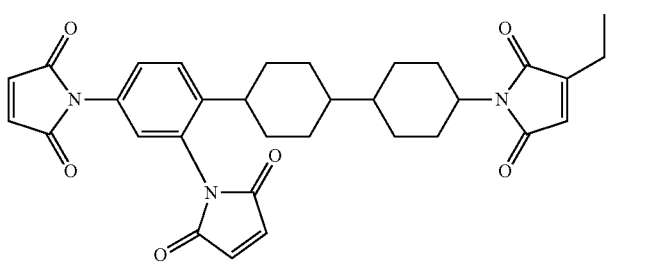 [SMILES: CCC1=CC(=O)N(C2CCC(C3CCC(c4ccc(N5C(=O)C=CC5=O)cc4N4C(=O)C=CC4=O)CC3)CC2)C1=O]

-continued

| | No. |
|---|---|
| 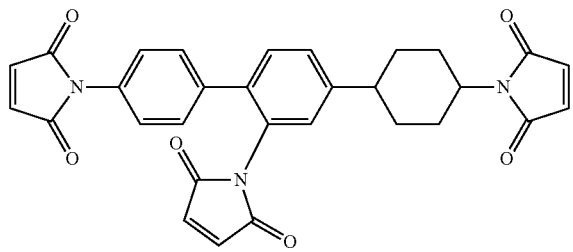 [SMILES: O=C1C=CC(=O)N1c1ccc(-c2ccc(C3CCC(N4C(=O)C=CC4=O)CC3)cc2N2C(=O)C=CC2=O)cc1] | 80 |
| 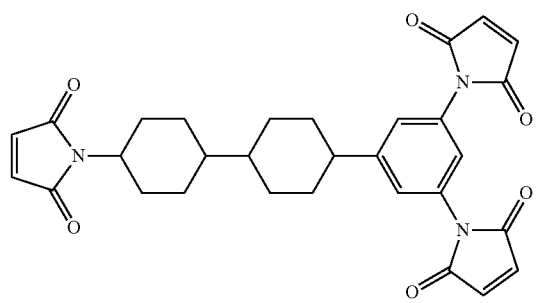 [SMILES: O=C1C=CC(=O)N1c1cc(C2CCC(C3CCC(N4C(=O)C=CC4=O)CC3)CC2)cc(N2C(=O)C=CC2=O)c1] | 81 |
| | 82 |
| 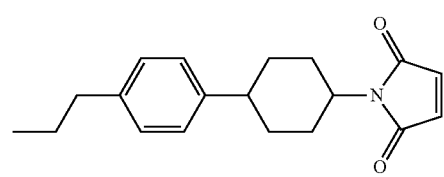 [SMILES: CCCc1ccc(C2CCC(N3C(=O)C=CC3=O)CC2)c(C)c1] | 83 |
| 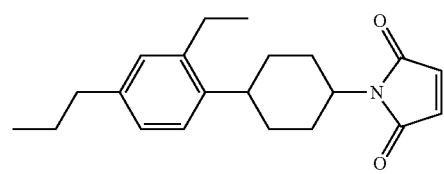 [SMILES: CCCc1cc(C)c(C2CCC(N3C(=O)C=CC3=O)CC2)c(CC)c1] | 84 |

Comparative Experiment 1

Compatibility at room temperature was measured on comparative compound (R-1) disclosed in JP 2004-131704 A (Patent literature No. 2). As a result, crystals precipitated at 1% by weight based on base liquid crystal (A). In compound (No. 9) of the present application, the crystals precipitated at 3% by weight, and therefore compound (9) may be reasonably referred to as having higher solubility in the liquid crystal composition.

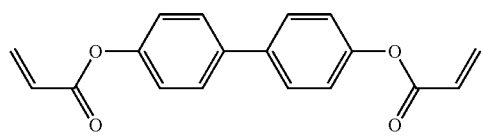

(R-1)

2. Example of Polymerizable Composition

The compounds described in Examples were described using symbols according to definitions in Table 1 below. In Table 1, a configuration of 1,4-cyclohexylene is trans. Parenthesized numbers described after the symbols in Examples represent formulas to which the compounds belong. A symbol (-) means any other liquid crystal compound. A content (percentage) of the liquid crystal compound is expressed in terms of weight percent (% by weight) based on the weight of the liquid crystal composition. Values of physical properties of the composition were summarized in a last part. The physical properties were measured according to the methods described above, and the measured values were directly described (without extrapolation).

TABLE 1

| Method of description of compounds using symbol $R-(A_1)-Z_1-\ldots-Z_n-(A_n)-R'$ | |
|---|---|
| 1) Left-terminal group R— | Symbol |
| $C_nH_{2n+1}-$ | n- |
| $C_nH_{2n+1}O-$ | nO— |
| $C_mH_{2m+1}OC_nH_{2n}-$ | mOn— |
| $CH_2=CH-$ | V— |
| $C_nH_{2n+1}-CH=CH-$ | nV— |
| $CH_2=CH-C_nH_{2n}-$ | Vn- |
| $C_mH_{2m+1}-CH=CH-C_nH_{2n}-$ | mVn- |
| $CF_2=CH-$ | VFF— |
| $CF_2=CH-C_nH_{2n}-$ | VFFn- |
| 2) Right-terminal group —R' | Symbol |
| $-C_nH_{2n+1}$ | -n |
| $-OC_nH_{2n+1}$ | —On |
| $-COOCH_3$ | —EMe |
| $-CH=CH_2$ | —V |
| $-CH=CH-C_nH_{2n+1}$ | —Vn |
| $-C_nH_{2n}-CH=CH_2$ | -nV |
| $-C_mH_{2m}-CH=CH-C_nH_{2n+1}$ | -mVn |
| $-CH=CF_2$ | —VFF |
| —F | —F |
| —Cl | —CL |
| $-OCF_3$ | —OCF3 |
| $-OCF_2H$ | —OCF2H |
| $-CF_3$ | —CF3 |
| $-OCH=CH-CF_3$ | —OVCF3 |
| $-C\equiv N$ | —C |
| 3) Bonding group —$Z_n$— | Symbol |
| $-C_nH_{2n}-$ | n |
| —COO— | E |
| —CH=CH— | V |
| $-CH_2O-$ | 1O |
| $-OCH_2-$ | O1 |
| $-CF_2O-$ | X |
| $-C\equiv C-$ | T |
| 4) Ring structure —$A_n$— | Symbol |
| 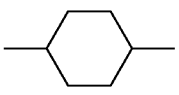 | H |
|  | B |
|  | B(F) |
| 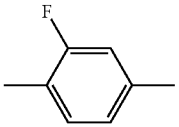 | B(2F) |
| 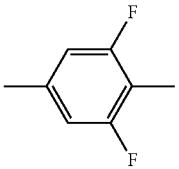 | B(F,F) |

TABLE 1-continued
Method of description of compounds using symbol
R—(A₁)—Z₁— . . . —Zₙ—(Aₙ)—R'
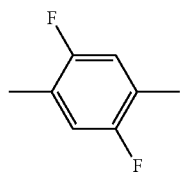 B(2F,5F)
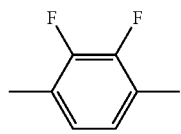 B(2F,3F)
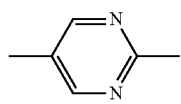 Py
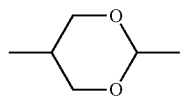 G
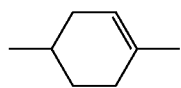 ch
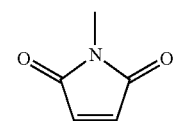 Mi
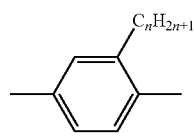 Bm(n)
5) Examples of description
Example 1. 3-HH-Mi
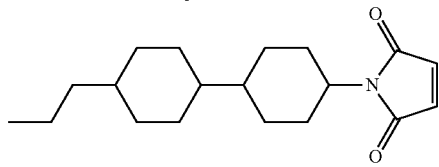
Example 2. 5-HHBB(F,F)-F
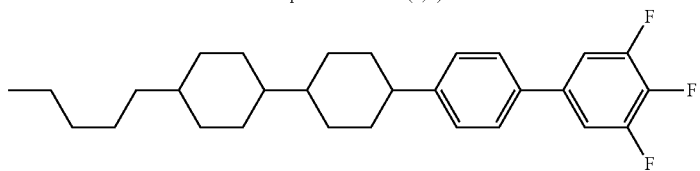
Example 3. 3-HB-O2
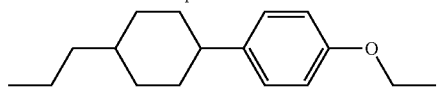
Example 4. 3-HBB(F,F)-F

TABLE 1-continued

Method of description of compounds using symbol
R—(A$_1$)—Z$_1$— . . . —Z$_n$—(A$_n$)—R'

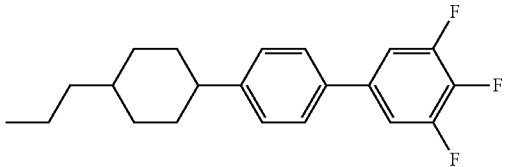 [SMILES: CCCC1CCC(c2ccc(-c3cc(F)c(F)c(F)c3)cc2)CC1]

Example 1

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 11% |
| 4-PyBB-F | (6-80) | 10% |
| 5-PyBB-F | (6-80) | 10% |
| 5-HBB(F)B-2 | (4-5) | 9% |
| 5-HBB(F)B-3 | (4-5) | 10% |

To the above composition, 3-BB-Mi (No. 11) was added at a proportion of 0.1% by weight.
NI=98.5° C.; η=39.6 mPa·s; Δn=0.190; Δε=8.1.

Example 2

| | | |
|---|---|---|
| 2-HB-C | (8-1) | 5% |
| 3-HB-C | (8-1) | 13% |
| 3-HB-O2 | (2-5) | 14% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 5% |
| 5-HHEB-F | (6-10) | 3% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

To the above composition, 3-BH-Mi (No. 81) was added at a proportion of 0.05% by weight.
NI=100.7° C.; η=17.9 mPa·s; Δn=0.101; Δε=4.8.

Example 3

| | | |
|---|---|---|
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 9% |
| 2-BBB(F)-F | (6-23) | 9% |
| 3-HBB(F)-F | (6-23) | 10% |
| 5-HBB(F)-F | (6-23) | 15% |
| 2-HBB-F | (6-22) | 4% |
| 3-HBB-F | (6-22) | 5% |
| 5-HBB-F | (6-22) | 3% |
| 3-HBB(F,F)-F | (6-24) | 5% |
| 5-HBB(F,F)-F | (6-24) | 10% |

To the above composition, 3-HB-Mi (No. 10) was added at a proportion of 0.1% by weight. In addition, compound (RM-1) described below was added at a proportion of 0.3% by weight.

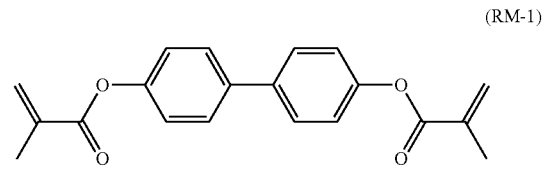 [SMILES: C=C(C)C(=O)Oc1ccc(-c2ccc(OC(=O)C(=C)C)cc2)cc1]

(RM-1)

NI=85.3° C.; η=24.9 mPa·s; Δn=0.116; Δε=5.8.

Example 4

| | | |
|---|---|---|
| 5-HB-CL | (5-2) | 16% |
| 3-HH-4 | (2-1) | 11% |
| 3-HH-5 | (2-1) | 4% |
| 3-HHB-F | (6-1) | 3% |
| 3-HHB-CL | (6-1) | 3% |
| 4-HHB-CL | (6-1) | 4% |
| 3-HHB(F)-F | (6-2) | 9% |
| 4-HHB(F)-F | (6-2) | 10% |
| 5-HHB(F)-F | (6-2) | 9% |
| 7-HHB(F)-F | (6-2) | 8% |
| 5-HBB(F)-F | (6-23) | 4% |
| 1O1-HBBH-5 | (4-1) | 3% |
| 3-HHBB(F,F)-F | (7-6) | 3% |
| 4-HHBB(F,F)-F | (7-6) | 3% |
| 5-HHBB(F,F)-F | (7-6) | 3% |
| 3-HH2BB(F,F)-F | (7-15) | 4% |
| 4-HH2BB(F,F)-F | (7-15) | 3% |

To the above composition, 3-HH-Mi (No. 9) was added at a proportion of 0.05% by weight.
NI=116.7° C.; η=20.6 mPa·s; Δn=0.093; Δε=4.0.

Example 5

| | | |
|---|---|---|
| 3-HHB(F,F)-F | (6-3) | 9% |
| 3-H2HB(F,F)-F | (6-15) | 9% |
| 4-H2HB(F,F)-F | (6-15) | 8% |
| 5-H2HB(F,F)-F | (6-15) | 7% |
| 3-HBB(F,F)-F | (6-24) | 21% |
| 5-HBB(F,F)-F | (6-24) | 18% |
| 3-H2BB(F,F)-F | (6-27) | 12% |
| 5-HHB(F,F)-F | (7-6) | 3% |
| 5-HHEBB(F,F)-F | (7-17) | 2% |
| 3-HH2BB(F,F)-F | (7-15) | 3% |
| 1O1-HBBH-4 | (4-1) | 5% |
| 1O1-HBBH-5 | (4-1) | 3% |

To the above composition, 3-BB-Mi (No. 11) was added at a proportion of 0.3% by weight.
NI=97.2° C.; η=34.9 mPa·s; Δn=0.116; Δε=9.1.

Example 6

| | | |
|---|---|---|
| 5-HB-F | (5-2) | 12% |
| 6-HB-F | (5-2) | 9% |
| 7-HB-F | (5-2) | 7% |
| 2-HHB-OCF3 | (6-1) | 5% |
| 3-HHB-OCF3 | (6-1) | 7% |
| 4-HHB-OCF3 | (6-1) | 7% |
| 5-HHB-OCF3 | (6-1) | 5% |
| 3-HH2B-OCF3 | (6-4) | 7% |
| 5-HH2B-OCF3 | (6-4) | 4% |
| 3-HHB(F,F)-OCF2H | (6-3) | 4% |
| 3-HHB(F,F)-OCF3 | (6-3) | 5% |
| 3-HH2B(F)-F | (6-5) | 3% |
| 3-HBB(F)-F | (6-23) | 11% |
| 5-HBB(F)-F | (6-23) | 8% |
| 5-HBBH-3 | (4-1) | 3% |
| 3-HB(F)BH-3 | (4-2) | 3% |

To the above composition, 3-HB-Mi (No. 10) was added at a proportion of 0.2% by weight.
NI=85.9° C.; η=14.7 mPa·s; Δn=0.092; Δε=4.4.

Example 7

| | | |
|---|---|---|
| 5-HB-CL | (5-2) | 9% |
| 3-HH-4 | (2-1) | 9% |
| 3-HHB-1 | (3-1) | 4% |
| 3-HHB(F,F)-F | (6-3) | 8% |
| 3-HBB(F,F)-F | (6-24) | 19% |
| 5-HBB(F,F)-F | (6-24) | 13% |
| 3-HHEB(F,F)-F | (6-12) | 9% |
| 4-HHEB(F,F)-F | (6-12) | 5% |
| 5-HHEB(F,F)-F | (6-12) | 4% |
| 2-HBEB(F,F)-F | (6-39) | 5% |
| 3-HBEB(F,F)-F | (6-39) | 4% |
| 5-HBEB(F,F)-F | (6-39) | 5% |
| 3-HHBB(F,F)-F | (7-6) | 6% |

To the above composition, 3-Bm(2)H-Mi (No. 82) was added at a proportion of 0.3% by weight. In addition, compound (RM-2) described below was added at a proportion of 0.3% by weight.

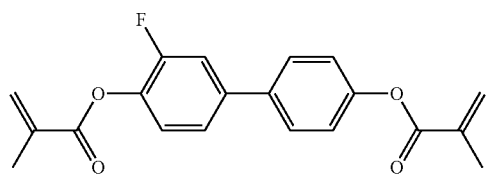
(RM-2)

NI=81.5° C.; η=23.6 mPa·s; Δn=0.102; Δε=9.1.

Example 8

| | | |
|---|---|---|
| 2-HB-C | (8-1) | 5% |
| 3-HB-C | (8-1) | 15% |
| 3-HB-O2 | (2-5) | 12% |
| 2-BTB-1 | (2-10) | 3% |
| 3-HHB-F | (6-1) | 4% |
| 3-HHB-1 | (3-1) | 4% |
| 3-HHB-O1 | (3-1) | 6% |
| 3-HHB-3 | (3-1) | 14% |
| 3-HHEB-F | (6-10) | 5% |
| 5-HHEB-F | (6-10) | 5% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |

To the above composition, Mi-H2H-Mi (No. 23) was added at a proportion of 0.2% by weight.
NI=102.1° C.; η=20.2 mPa·s; Δn=0.102; Δε=5.1.

Example 9

| | | |
|---|---|---|
| 3-HB-CL | (5-2) | 6% |
| 5-HB-CL | (5-2) | 4% |
| 3-HHB-OCF3 | (6-1) | 5% |
| 3-H2HB-OCF3 | (6-13) | 5% |
| 5-H4HB-OCF3 | (6-19) | 15% |
| V-HHB(F)-F | (6-2) | 5% |
| 3-HHB(F)-F | (6-2) | 6% |
| 5-HHB(F)-F | (6-2) | 5% |
| 3-H4HB(F,F)-CF3 | (6-21) | 9% |
| 5-H4HB(F,F)-CF3 | (6-21) | 9% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 9% |
| 3-HBEB(F,F)-F | (6-39) | 5% |

To the above composition, 3-BH-Mi (No. 81) was added at a proportion of 0.15% by weight.
NI=70.1° C.; η=25.3 mPa·s; Δn=0.097; Δε=8.3.

Example 10

| | | |
|---|---|---|
| 5-HB-CL | (5-2) | 16% |
| 7-HB(F,F)-F | (5-4) | 4% |
| 3-HH-4 | (2-1) | 11% |
| 3-HH-5 | (2-1) | 5% |
| 3-HB-O2 | (2-5) | 14% |
| 3-HHB-1 | (3-1) | 7% |
| 3-HHB-O1 | (3-1) | 6% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 5% |

To the above composition, 3-Bm(2)H-Mi (No. 82) was added at a proportion of 0.05% by weight.
NI=71.0° C.; η=13.7 mPa·s; Δn=0.073; Δε=2.8.

Example 11

| | | |
|---|---|---|
| 5-HB-CL | (5-2) | 3% |
| 7-HB(F)-F | (5-3) | 7% |
| 3-HH-4 | (2-1) | 9% |
| 3-HH-EMe | (2-2) | 22% |
| 3-HHEB-F | (6-10) | 8% |
| 5-HHEB-F | (6-10) | 7% |

-continued

| | | |
|---|---|---|
| 3-HHEB(F,F)-F | (6-12) | 10% |
| 4-HHEB(F,F)-F | (6-12) | 6% |
| 4-HGB(F,F)-F | (6-103) | 6% |
| 5-HGB(F,F)-F | (6-103) | 6% |
| 2-H2GB(F,F)-F | (6-106) | 4% |
| 3-H2GB(F,F)-F | (6-106) | 6% |
| 5-GHB(F,F)-F | (6-109) | 6% |

To the above composition, Mi-H2H-Mi (No. 23) was added at a proportion of 0.25% by weight.
NI=78.7° C.; η=19.9 mPa·s; Δn=0.064; Δε=5.8.

Example 12

| | | |
|---|---|---|
| 1V2-BEB(F,F)-C | (8-15) | 7% |
| 3-HB-C | (8-1) | 18% |
| 2-BTB-1 | (2-10) | 10% |
| 5-HH-VFF | (2-1) | 30% |
| 3-HHB-1 | (3-1) | 5% |
| VFF-HHB-1 | (3-1) | 6% |
| VFF2-HHB-1 | (3-1) | 11% |
| 3-H2BTB-2 | (3-17) | 5% |
| 3-H2BTB-3 | (3-17) | 5% |
| 3-H2BTB-4 | (3-17) | 3% |

To the above composition, Mi-H2H-Mi (No. 23) was added at a proportion of 0.25% by weight.
NI=78.7° C.; η=19.9 mPa·s; Δn=0.064; Δε=5.8.

INDUSTRIAL APPLICABILITY

A liquid crystal display device having a mode such as a PSA mode can be prepared by polymerizing a polymerizable composition containing polymerizable compound (1) and a liquid crystal composition. The device has a wide temperature range in which the device can be used, a short response time, a large voltage holding ratio, a low threshold voltage, a large contrast ratio and a long service life. Accordingly, Compound (1) can be used in a liquid crystal projector, a liquid crystal television and so forth. Compound (1) can be used also as a raw material of an optical anisotropic body.

What is claimed is:
1. A polymerizable composition, containing at least one polymerizable compound represented by formula (1):

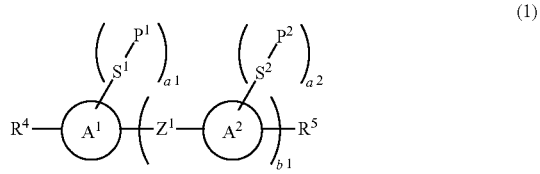

(1)

wherein, in formula (1),
P$^1$ and P$^2$ are independently a polymerizable group, wherein the polymerizable group comprises maleimide as a monovalent group represented by formula (A), acryloyloxy (P-1), vinyloxy (P-2) or oxiranyl (P-3);

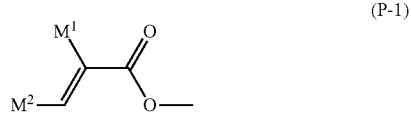

(P-1)

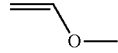

(P-2)

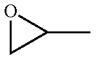

(P-3)

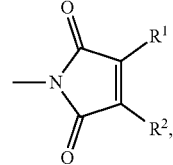

(A)

in (P-1), M$^1$ and M$^2$ are independently hydrogen, fluorine, methyl or trifluoromethyl,
in formula (A), R$^1$ and R$^2$ are independently hydrogen, halogen or alkyl having 1 to 20 carbons, and in the alkyl, at least one —CH$_2$— may be replaced by —O— or —S—, and at least one —(CH$_2$)$_2$— may be replaced by —CH=CH—, and in the alkyl having 1 to 20 carbons in which at least one —CH$_2$— may be replaced by —O— or —S—, and at least one —(CH$_2$)$_2$— may be replaced by —CH=CH—, at least one hydrogen may be replaced by halogen;
in formula (1), S$^1$ and S$^2$ are independently a single bond or alkylene having 1 to 10 carbons, and in the alkylene, at least one —CH$_2$— may be replaced by —O—, —CO—, —COO— or —OCO—, and at least one —CH$_2$—CH$_2$— may be replaced by —CH=CH— or —C≡C— and in the divalent groups, at least one hydrogen may be replaced by halogen or alkyl having 1 to 3 carbons;
R$^4$ and R$^5$ are independently hydrogen, halogen, —S$^1$—P$^1$, —S$^2$—P$^2$ or alkyl having 1 to 20 carbons, and in the alkyl, at least one —CH$_2$— may be replaced by —O— or —S—, and at least one —(CH$_2$)$_2$— may be replaced by —CH=CH—, and in the alkyl in which at least one —CH$_2$— may be replaced by —O— or —S—, and at least one —(CH$_2$)$_2$— may be replaced by —CH=CH—, at least one hydrogen may be replaced by halogen;
a1 and a2 are independently 0, 1, 2, 3 or 4;
a total number of —S$^1$—P$^1$ and —S$^2$—P$^2$ is 1 to 8, and at least one of —S$^1$—P$^1$ and —S$^2$—P$^2$ is the monovalent group represented by formula (A);
and
in formula (1),
ring A$^1$ and ring A$^2$ are independently a divalent group derived from alicyclic hydrocarbon having 3 to 18 carbons, aromatic hydrocarbon having 6 to 18 carbons or heteroaromatic hydrocarbon having 3 to 18 carbons, and in the divalent groups, at least one hydrogen may be replaced by halogen, alkyl having 1 to 12 carbons, alkoxy having 1 to 12 carbons, alkenyl having 1 to 12 carbons or alkenyloxy having 2 to 12 carbons, and in the monovalent hydrocarbon groups, at least one hydrogen may be replaced by halogen;
Z$^1$ is a single bond or alkylene having 1 to 10 carbons, and in the alkylene, at least one —CH$_2$— may be replaced by —O—, —CO—, —COO— or —OCO—, and at least one —CH$_2$—CH$_2$— may be replaced by —CH=CH—, —C(CH$_3$)=CH—, —CH=C(CH$_3$)—, —C(CH$_3$)=C(CH$_3$)— or —CH=CH—, and in divalent groups, at least one hydrogen may be replaced by halogen; and b1 is 0, 1, 2 or 3;

wherein, when a1=0, R$^4$ is hydrogen, —S$^1$—P$^1$ or alkyl having 2 to 20 carbons, with a proviso that R$^4$ is not the monovalent group represented by formula (A), wherein in the alkyl, at least one —CH$_2$— may be replaced by —O— or —S—, and at least one —(CH$_2$)$_2$— may be replaced by —CH=CH—, when a2=0, R$^5$ is not the monovalent group represented by formula (A), when b1=0 and a1 is 1 or 2, then R$^5$ is —S$^2$—P$^2$ and R$^4$ is not hydrogen, or R$^1$ or R$^2$ of the monovalent group represented by formula (A) in the polymerizable group P$^1$ or P$^2$ is not hydrogen, when b1=1, a1=0, a2=1, and R$^4$ is —S$^1$—P$^1$, then at least one of ring A$^1$ and ring A$^2$ is not an aromatic hydrocarbon having 6 to 18 carbons, or R$^5$ is not hydrogen, or R$^1$ or R$^2$ of the monovalent group represented by formula (A) in the polymerizable group P$^1$ is different from R$^1$ or R$^2$ of the monovalent group represented by formula (A) in the polymerizable group P$^2$;

when b1=1, a1=1, a2=0, and R$^5$ is —S$^2$—P$^2$, then at least one of ring A$^1$ and ring A$^2$ is not an aromatic hydrocarbon having 6 to 18 carbons, or R$^4$ is not hydrogen, or R$^1$ or R$^2$ of the monovalent group represented by formula (A) in the polymerizable group P$^1$ is different from R$^1$ or R$^2$ of the monovalent group represented by formula (A) in the polymerizable group P$^2$;

when b1=1, a1=1 and a2=1, then at least one of ring A$^1$ and ring A$^2$ is not an aromatic hydrocarbon having 6 to 18 carbons, or R$^4$ is different from R$^5$, or R$^1$ or R$^2$ of the monovalent group represented by formula (A) in the polymerizable group P$^1$ is different from R$^1$ or R$^2$ of the monovalent group represented by formula (A) in the polymerizable group P$^2$, when b1=2 or 3, a1=1, a2=0 and R$^5$ is —S$^2$—P$^2$, then at least one of ring A$^1$ and ring A$^2$ is not an aromatic hydrocarbon having 6 to 18 carbons, or R$^4$ is not hydrogen or —S$^1$—P$^1$ or R$^1$ or R$^2$ of the monovalent group represented by formula (A) in the polymerizable group P$^1$ is different from R$^1$ or R$^2$ of the monovalent group represented by formula (A) in the polymerizable group P$^2$, or Z$^1$ s are different from each other; and when b1=2 or 3 and a1=0, then a2≥1.

2. The polymerizable composition according to claim 1, wherein the at least one polymerizable compound is represented by any one of formula (1-1-1) to formula (1-1-3):

(1-1-1)

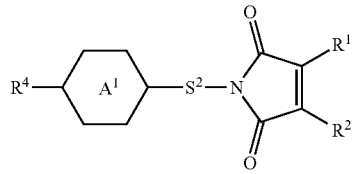

(1-1-2)

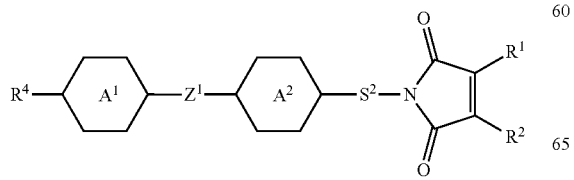

(1-1-3)

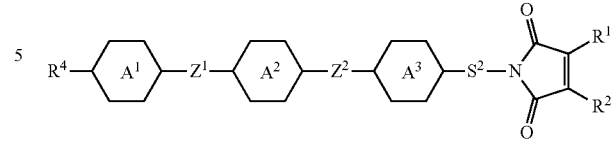

wherein, in formula (1-1-1) to formula (1-1-3),

R$^1$ and R$^2$ are independently hydrogen, halogen or alkyl having 1 to 20 carbons, and in the alkyl, at least one —CH$_2$— may be replaced by —O— or —S—, and at least one —(CH$_2$)$_2$— may be replaced by —CH=CH—, and in the alkyl in which at least one —CH$_2$— may be replaced by —O— or —S—, and at least one —(CH$_2$)$_2$— may be replaced by —CH=CH—, at least one hydrogen may be replaced by halogen;

R$^4$ is hydrogen, —S$^1$—P$^1$ or alkyl having 2 to 20 carbons, with a proviso that R$^4$ is not the monovalent group represented by formula (A), wherein in the alkyl, at least one —CH$_2$— may be replaced by —O— or —S—, and at least one —(CH$_2$)$_2$— may be replaced by —CH=CH—;

S$^1$ and S$^2$ are independently a single bond or alkylene having 1 to 10 carbons, and in the alkylene, at least one —CH$_2$— may be replaced by —O—, —CO—, —COO— or —OCO—, and at least one —CH$_2$—CH$_2$— may be replaced by —CH=CH— or —C≡C—, and in the divalent groups, at least one hydrogen may be replaced by halogen or alkyl having 1 to 3 carbons;

P$^1$ is a polymerizable group;

ring A$^1$, ring A$^2$ and ring A$^3$ are independently a divalent group derived from alicyclic hydrocarbon having 3 to 18 carbons, aromatic hydrocarbon having 6 to 18 carbons or heteroaromatic hydrocarbon having 3 to 18 carbons, and in the divalent groups, at least one hydrogen may be replaced by halogen, alkyl having 1 to 12 carbons, alkoxy having 1 to 12 carbons, alkenyl having 1 to 12 carbons or alkenyloxy having 2 to 12 carbons, and in the monovalent hydrocarbon groups, at least one hydrogen may be replaced by halogen; and Z$^1$ and Z$^2$ are independently a single bond or alkylene having 1 to 10 carbons, and in the alkylene, at least one —CH$_2$— may be replaced by —O—, —CO—, —COO— or —OCO—, and at least one —CH$_2$—CH$_2$— may be replaced by —CH=CH—, —C(CH$_3$)=CH—, —CH=C(CH$_3$)—, —C(CH$_3$)=C(CH$_3$)— or —CH=CH—, and in the divalent groups, at least one hydrogen may be replaced by halogen.

3. The polymerizable composition according to claim 1, wherein the at least one polymerizable compound is represented by any one of formula (1-1-4) to formula (1-1-6):

(1-1-4)

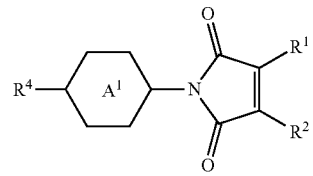

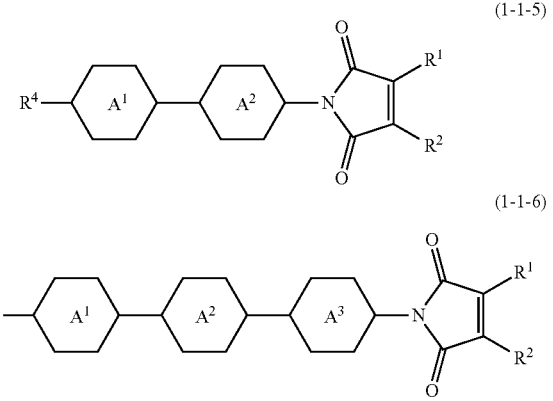

(1-1-5)

(1-1-6)

wherein, in formula (1-1-4) to formula (1-1-6),
  $R^1$ and $R^2$ are independently hydrogen, halogen or alkyl having 1 to 20 carbons, and in the alkyl, at least one —$CH_2$— may be replaced by —O— or —S—, and at least one —$(CH_2)_2$— may be replaced by —CH=CH—, and in the alkyl in which at least one —$CH_2$— may be replaced by —O— or —S—, and at least one —$(CH_2)_2$— may be replaced by —CH=CH—, at least one hydrogen may be replaced by halogen;
  $R^4$ is hydrogen, —$S^1$—$P^1$ or alkyl having 2 to 20 carbons, with a proviso that $R^4$ is not the monovalent group represented by formula (A), wherein in the alkyl, at least one —$CH_2$— may be replaced by —O— or —S—, and at least one —$(CH_2)_2$— may be replaced by —CH=CH—;
  $S^1$ is a single bond or alkylene having 1 to 10 carbons, and in the alkylene, at least one —$CH_2$— may be replaced by —O—, —CO—, —COO— or —OCO—, and at least one —$CH_2$—$CH_2$— may be replaced by —CH=CH— or —C≡C—, and in the divalent groups, at least one hydrogen may be replaced by halogen or alkyl having 1 to 3 carbons;
  $P^1$ is a polymerizable group; and
  ring $A^1$, ring $A^2$ and ring $A^3$ are independently a divalent group derived from alicyclic hydrocarbon having 3 to 18 carbons, aromatic hydrocarbon having 6 to 18 carbons or heteroaromatic hydrocarbon having 3 to 18 carbons, and in the divalent groups, at least one hydrogen may be replaced by halogen, alkyl having 1 to 12 carbons, alkoxy having 1 to 12 carbons, alkenyl having 1 to 12 carbons or alkenyloxy having 2 to 12 carbons, and in the monovalent hydrocarbon groups, at least one hydrogen may be replaced by halogen.

4. The polymerizable composition according to claim 1, wherein the at least one polymerizable compound is represented by formula (1-1-5):

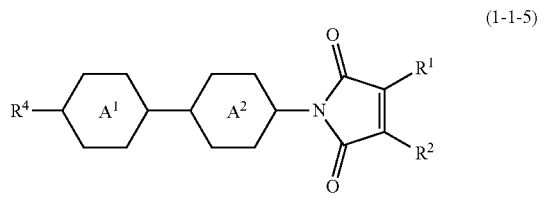

(1-1-5)

wherein, in formula (1-1-5),
  $R^1$ and $R^2$ are independently hydrogen, halogen or alkyl having 1 to 20 carbons, and in the alkyl, at least one —$CH_2$— may be replaced by —O— or —S—, and at least one —$(CH_2)_2$— may be replaced by —CH=CH—, and in the alkyl in which at least one —$CH_2$— may be replaced by —O— or —S—, and at least one —$(CH_2)_2$— may be replaced by —CH=CH—, at least one hydrogen may be replaced by halogen;
  $R^4$ is hydrogen, —$S^1$—$P^1$ or alkyl having 2 to 20 carbons, with a proviso that $R^4$ is not the monovalent group represented by formula (A), wherein in the alkyl, at least one —$CH_2$— may be replaced by —O— or —S—, and at least one —$(CH_2)_2$— may be replaced by —CH=CH—; and
  ring $A^1$ and ring $A^2$ are independently 1,4-cyclohexylene, 1,4-cyclohexenylene and 1,4-phenylene, and at least one hydrogen on the rings may be replaced by halogen.

5. The polymerizable composition according to claim 1, wherein the at least one polymerizable compound is represented by formula (1-1-7):

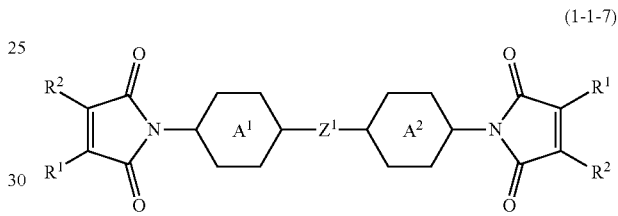

(1-1-7)

wherein, in formula (1-1-7),
  $R^1$ and $R^2$ are independently hydrogen, halogen or alkyl having 1 to 20 carbons, and in the alkyl, at least one —$CH_2$— may be replaced by —O— or —S—, and at least one —$(CH_2)_2$— may be replaced by —CH=CH—, and in the alkyl in which at least one —$CH_2$— may be replaced by —O— or —S—, and at least one —$(CH_2)_2$— may be replaced by —CH=CH—, at least one hydrogen may be replaced by halogen;
  ring $A^1$ and ring $A^2$ are independently 1,4-cyclohexylene and 1,4-phenylene, and at least one hydrogen on the rings may be replaced by halogen; and
  $Z^1$ is a single bond or alkylene having 1 to 10 carbons, and in the alkylene, at least one —$CH_2$— may be replaced by —O—, —CO—, —COO— or —OCO—, and at least one —$CH_2$—$CH_2$— may be replaced by —CH=CH—, —C($CH_3$)=CH—, —CH=C($CH_3$)—, —C($CH_3$)=C($CH_3$)— or —CH≡CH—, and in the divalent groups, at least one hydrogen may be replaced by halogen.

6. The polymerizable composition according to claim 1, further containing at least one compound selected from the group of compounds represented by formulas (2) to (4):

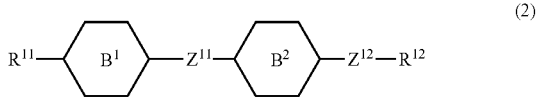

(2)

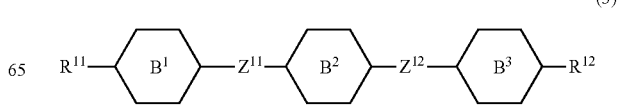

(3)

-continued

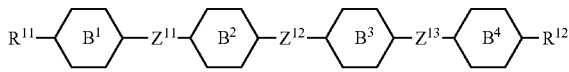
(4)

wherein, in formulas (2) to (4),
$R^{11}$ and $R^{12}$ are independently alkyl having 1 to 10 carbons or alkenyl having 2 to 10 carbons, and in the alkyl or the alkenyl, at least one —CH$_2$— may be replaced by —O—, and at least one hydrogen may be replaced by fluorine;
ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —CH$_2$CH$_2$—, —CH=CH—, —C≡C— or —COO—.

7. The polymerizable composition according to claim 1, further containing at least one compound selected from the group of compounds represented by formulas (5) to (7):

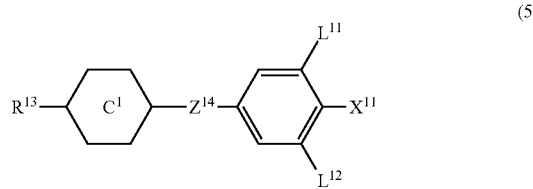
(5)

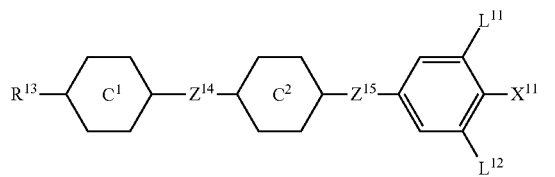
(6)

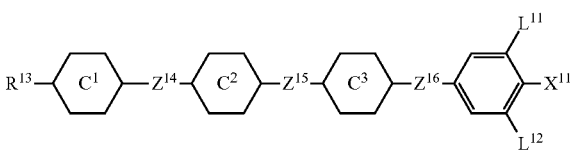
(7)

wherein, in formulas (5) to (7),
$R^{13}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
$Z^{14}$ and $Z^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and
$L^{11}$ and $L^{12}$ are independently hydrogen or fluorine.

8. The polymerizable composition according to claim 1, further containing at least one compound selected from the group of compounds represented by formula (8):

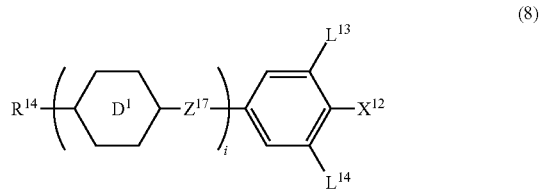
(8)

wherein, in formula (8),
$R^{14}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;
$X^{12}$ is —C≡N or —C≡C—C≡N;
ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
$Z^{17}$ is a single bond, —CH$_2$CH$_2$—, —C≡C—, —COO—, —CF$_2$O—, —OCF$_2$—, or —CH$_2$O—;
$L^{13}$ and $L^{14}$ are independently hydrogen or fluorine; and
i is 1, 2, 3 or 4.

9. A liquid crystal composite, formed by polymerization of the polymerizable composition according to claim 1.

10. An optical anisotropic body, formed by polymerization of the polymerizable composition according to claim 1.

11. A liquid crystal display device, including the polymerizable composition according to claim 1.

12. A method of using the polymerizable compound according to claim 1, comprising:
polymerizing the polymerizable composition containing the polymerizable compound and a liquid crystal composition to form a liquid crystal device.

13. A liquid crystal display device, including the liquid crystal composite according to claim 9.

* * * * *